United States Patent [19]

Bolger et al.

[11] Patent Number: 5,591,733

[45] Date of Patent: *Jan. 7, 1997

[54] METHODS, COMPOSITIONS, AND COMPOUNDS FOR ALLOSTERIC MODULATION OF THE GABA RECEPTOR BY MEMBERS OF THE ANDROSTANE AND PREGNANE SERIES

[75] Inventors: Michael B. Bolger, Los Alamitos; Kelvin W. Gee, Irvine; Nancy C. Lan, South Pasadena; Robert H. Purdy, La Jolla; Seid Mirsadeghi, Rolling Hills, all of Calif.; Syed Hasan Tahir, Edmonton, Canada; Delia Belelli, Kingsbarns by St. Andrews, Scotland

[73] Assignee: University of Southern California, Los Angeles, Calif.

[*] Notice: The portion of the term of this patent subsequent to Aug. 3, 2010, has been disclaimed.

[21] Appl. No.: 101,497

[22] Filed: Aug. 2, 1993

Related U.S. Application Data

[63] Continuation of Ser. No. 745,216, Aug. 13, 1991, Pat. No. 5,232,917, which is a continuation-in-part of Ser. No. 521,724, May 10, 1990, Pat. No. 5,120,723, which is a continuation-in-part of Ser. No. 379,047, Jul. 13, 1989, abandoned, which is a continuation-in-part of Ser. No. 89,362, Aug. 25, 1987, abandoned.

[51] Int. Cl.$^6$ .................. C07J 9/00; C07J 21/00; C07J 43/00; A61K 31/58; A61K 31/56
[52] U.S. Cl. .................. 514/172; 552/505; 552/540; 552/541; 552/542; 552/544; 552/546; 552/547; 514/169; 514/176; 514/177; 514/178; 514/179; 514/180; 514/181; 514/182; 540/36; 540/94; 540/95; 540/96; 540/97; 540/98; 540/99; 540/106; 540/107; 540/108; 540/109; 540/110; 540/111; 540/112; 540/114; 540/116; 540/120
[58] Field of Search .................. 540/94–99, 106–112, 540/36, 114, 116, 120; 514/169, 172, 176–182; 552/540, 541, 542, 544, 546, 547, 505

[56] References Cited

U.S. PATENT DOCUMENTS

| | | | |
|---|---|---|---|
| 2,306,635 | 12/1942 | Marker | 260/397.1 |
| 3,061,606 | 10/1962 | Gut et al. | 260/239.55 |
| 3,132,160 | 5/1964 | Wechter | 260/397.3 |
| 3,139,445 | 6/1964 | Wiechert et al. | 260/397.1 |
| 3,214,427 | 10/1965 | Ercoli et al. | 260/239.55 |
| 3,385,849 | 5/1968 | Krubiner et al. | 260/239.55 |
| 3,494,943 | 2/1970 | Krsek | 260/397.45 |
| 3,636,011 | 1/1972 | Phillipps et al. | 260/397.3 |
| 3,637,670 | 1/1972 | Fried | 260/239.55 |
| 3,647,829 | 3/1972 | Kruger | 260/397.4 |
| 3,665,021 | 5/1972 | Elks et al. | 260/397.45 |
| 3,726,864 | 4/1973 | Phillipps et al. | 260/239.55 |
| 3,763,195 | 10/1973 | Davis et al. | 260/397.45 |
| 3,816,624 | 6/1974 | Davis et al. | 424/243 |
| 3,822,297 | 7/1974 | Phillipps et al. | 260/397.45 |
| 3,822,298 | 7/1974 | Clayton et al. | 260/397.4 |
| 3,825,565 | 7/1974 | Gregory et al. | 260/397.4 |
| 3,869,451 | 3/1975 | Phillipps et al. | 260/239.5 |
| 3,875,148 | 4/1975 | Elks et al. | 260/239.5 |
| 3,882,151 | 5/1975 | Phillipps et al. | 260/397.45 |
| 3,900,561 | 8/1975 | Davis et al. | 424/238 |
| 3,943,124 | 3/1976 | Phillipps et al. | 260/239.55 R |
| 3,953,429 | 4/1976 | Cook et al. | 260/239.55 R |
| 3,959,260 | 5/1976 | Phillipps et al. | 260/239.5 |
| 3,969,345 | 7/1976 | Phillipps et al. | 260/239.5 |
| 3,983,111 | 9/1976 | Phillipps et al. | 260/239.5 |
| 3,989,686 | 11/1976 | Phillipps et al. | 260/239.55 R |
| 3,998,829 | 12/1976 | Phillipps et al. | 260/239.5 |
| 4,029,777 | 6/1977 | Engelfried et al. | 424/242 |
| 4,061,661 | 12/1977 | Kerb et al. | 260/397.45 |
| 4,192,871 | 3/1980 | Phillipps et al. | 424/241 |
| 4,197,296 | 4/1980 | Phillipps et al. | 424/241 |
| 4,213,978 | 7/1980 | Bodor et al. | 424/241 |
| 4,360,470 | 11/1982 | Batcho et al. | 260/397.1 |
| 4,424,218 | 1/1984 | Deraedt et al. | 424/238 |
| 5,120,723 | 6/1992 | Gee et al. | 514/176 |
| 5,208,227 | 5/1993 | Gee et al. | 514/172 |
| 5,232,917 | 8/1993 | Bolger et al. | 514/176 |
| 5,371,077 | 12/1994 | Schroepfer, Jr. et al. | 514/179 |

FOREIGN PATENT DOCUMENTS

| | | |
|---|---|---|
| 0030368 | 8/1981 | European Pat. Off. . |
| 1046039 | 12/1958 | Germany . |
| 2162555 | 6/1972 | Germany . |
| 2218413 | 11/1972 | Germany . |
| 2322532 | 11/1973 | Germany . |
| 2526373 | 12/1976 | Germany . |
| 1380248 | 1/1975 | United Kingdom . |
| 1380246 | 1/1975 | United Kingdom . |
| 1581235 | 12/1980 | United Kingdom . |
| 1581234 | 12/1980 | United Kingdom . |
| WO93/18053 | 9/1993 | WIPO . |

OTHER PUBLICATIONS

Aird, R. B. and Gordan, G. S., "Anticonvulsive Properties of Desoxycorticosterone," *J. Amer. Med. Assoc.* 145(10):715–719 (1951).

Arafat et al., "Sedative and hypnotic effects of oral administration of micronized progesterone may be mediated through its metabolites," *Am. J. Obstet. Gynecol.* 159(5):1203–1209 (1988).

Atkinson et al., "Action of Some Steroids on the Central Nervous System of the Mouse," *J. Med. Chem.* 8:426–432 (1965).

Backstrom et al., "Endocrinological Aspects of Cyclical Mood Changes During the Menstrual Cycle or the Premenstrual Syndrome," *J. Psychosom. Obstet. Gynaecol.* 2:8–20 (1983).

Backstrom et al., "Ovarian Steroid Hormones. Effects on Mood, Behaviour and Brain Excitability," *Acta Obstet. Gynecol. Scand. Suppl.* 130:19–24 (1985).

(List continued on next page.)

*Primary Examiner*—Cecilia Tsang
*Attorney, Agent, or Firm*—Sterne, Kessler, Goldstein & Fox P.L.L.C.

[57] ABSTRACT

Method, compositions, and compounds for modulating brain excitability to alleviate stress, anxiety, insomnia and seizure activity using certain steroid derivatives that act at a newly identified site on the gamma-aminobutyric acid receptor-chloride ionophore (GR) complex.

129 Claims, No Drawings

OTHER PUBLICATIONS

Barker et al., "Potentiation of Y–Aminobutyric–Acid–Activated Chloride Conductance by a Steroid Anaesthetic in Cultured Rat Spinal Neurones," *J. Physiol.* 386:485–501 (1987).

Barnes, D. M., "Steroids May Influence Changes in Mood," *Science* 232:1344–1345 (1986).

Barton et al., "Constitution of limonin and related bitter principles," *Chem. Abstracts* 55:11458d–11461c (1961).

Belelli et al., "Anticonvulsant Profile of the Progesterone Metabolite 5–α–pregnan–3–α–ol–20–one," *Eur. J. Pharmacol.* 166(2):325–329 (1989).

Blumstein et al., "Further Characterization of a Simple, Automated Exploratory Model for the Anxiolytic Effects of Benzodiazepines," *Pharmacol. Biochem. Behav.* 18:37–40 (1983).

Bodor, N., "Novel Approaches in Pro Drug Design," *Drugs of the Future* 6(3):165–182 (1981).

Bruhwyler, J., "Anxiolytic Potential of a Microgram Dose of Chlordiazepoxide in the Open–field Test," *Eur. J. Pharmacol.* 187:547–549 (1990).

Bruhwyler et al., "Anxiolytic Potential o Sulpiride, Clozapine and Derivatives in the Open–field Test," *Pharmacol. Biochem. Behav.* 36(1):57–61 (1990.

Bundgaard, H., *Design of Prodrugs*, H. Bundgaard, ed., Elsevier, N.Y. (1985).

Bush, I.E. and Mahesh, V.B., "Metabolism of 9α—Fluorocortisone and 9α—Fluorocortisol," *Biochem. J.* 69:9P–10P (1958).

Callachan et al, "Modulation of the $GABA_A$ receptor by progesterone metabolites," *Proc. R. Soc. Lond. B* 231:359–369 (1987).

Chemical Abstracts, STN File CA, Abstract for German Patent No. 2218413, Anner et al. "6α, 9α—Difluoro—16α—methyl—11β, 17α—dihydroxy—3β—acetoxy—20—oxopregn—4—ene" (Nov. 9, 1972).

Chemical Abstracts, STN File CA, Abstract for European Patent Appl. No. 0 030 368, Schulze et al., "11—Keto Steroids" (Aug. 17, 1981).

Chemical Abstracts, STN File CA, Abstract for German Patent No. 2162555, Cook et al., "3α–Hydroxy–5α–pregnan–20–one derivatives" (Jun. 22, 1972).

Chin et al., "Status epilepticus controlled by althesin infusion," *Anaesth. Intensive Care* 7(1):50–52 (1979).

Christmas et al., "A Comparison of the Effects of Some Benzodiazepines and Other Drugs on Aggressive and Exploratory Behaviour in Mice and Rats," *Neuropharmacology* 9:17–29 (1970).

Craig, C. R., "Anticonvulsant Activity of Steroids: Separability of Anticonvulsant from Hormonal Effects," *J. Pharmacol. Exp. Ther.* 153 (2):337–343 (1966).

Craig, C. R. and Deason, J. R., "Anticonvulsant Activity of Steroids, Specificity of Structure," *Arch. int. Pharmacodyn.* 172 (2):366–372 (1968).

Crawley, J. N., "Neuropharmacologic Specificity of a Simple Animal Model for the Behavioral Actions of Benzodiazepines," *Pharmacol. Biochem. Behav.* 15:695–699 (1981).

Crawley, J. N. and Davis, L. G., "Baseline Exploratory Activity Predicts Anxiolytic Responsiveness to Diazepam in Five Mouse Strains," *Brain Res. Bull.* 8:609–612 (1982).

Crawley, J. N. and Goodwin. F. K., "Preliminary Report of a Simple Animal Behavior Model for the Anxiolytic Effects of Benzodiazepines," *Pharmacol. Biochem. Behav.* 13 (2):167–170 (1980).

Crawley et al., "Absence of Intrinsic Antagonist Actions of Benzodiazepine Antagonists on an Exploratory Model of Anziety in the Mouse," *Neuropharmacology* 23:531–537 (1984).

Crawley et al., "Annxiolytic Activity of an Endogenous Adrenal Steroid," *Brain Res.* 398:382–385 (1986).

Czira, G. and Kecskes, L., "Identification and Quantitation of 3α, 21–dihydroxy–5α–pregn–9 (11)–en—20—one, An Artifact of Allotetrahydrocorticosterone in Acid—hydrolysed Urine of Children," *Proc. of the Symp. on the Analysis of Steroids*, S. Görög, ed., Szeged, Hungary, pp. 421–427 (Jun. 12–14, 1984).

Dalton, K., in: Premenstrual Syndrome and Progesterone Therapy, 2nd ed., Chicago, Chicago yearbook (1984).

Davies, C. and Steinberg, H., "A Biphasic Effect of Chlordiazepoxide on Animal Locomotor Activity," *Neurosci. Lett.* 46:347–351 (1984).

De Riu et al., "Anticonvulsant Activity of Althesin on Experimental Epilepsy," *Br. J. Anaesth.* 54:343–347 (1982).

Dennerstein et al., "Progesterone and the Premenstrual Syndrome: A Double Blind Crossover Trial," *British Med. J.* 290:1617–1621 (1985).

Eimasry, A. H. and Gisvold, O., "19—Norsteroids of Unnatural Configuration from Ergosterol," *J. Pharm. Sci.* 59 (4):449–458 (1970).

Eneroth et al., "Excretion and Anticonvulsant Activity of Steroid Hormones in an Infant with Infantile Spasm and Hypsarrhytmia Treated with Excessive Doses of ACTH", *J. Steroid Biochem.* 3:877–887 (1972).

Fieser, L. F. and Fieser, M., in: Steroids, Reinhold Publ. Corp., N.Y., pp. 566, 573, 575 and 614 (1959).

File, S. E., "The Use of Social Interaction as a Method for Detecting Anxiolytic Acitivty of Chlordiazepoxide–like Drugs," *J. Neurosci. Meth.* 2;219–238 (1980).

Gee, K. W. and Yamamura, H. I., "Benzodiazepines and Barbituates: Drugs for the Treatment of Anxiety Insomnia, and Seizure Disorders," in: Drugs in Central Nervous System Disrorders, D. C. Horwell, ed., pp. 123–147.

Gee et al., "GABA–Dependent Modulation of the $Cl^-$Ionophore by Steroids in Rat Brain," *Eur. J. Pharmacol.* 136:419–423 (1987).

Gee et al., "Modulation of the Chloride Ionophore by Benzodiazepine Receptor Ligands: Influence of Gamma–aminobutyric Acid and Ligand Efficacy," *Molec. Pharmacol.* 30:218–225 (1986).

Geller et al., "The Effects of Chlordiazepoxide and Chlorpromazine on a Punishment Discrimination" *Psychopharmacologia* 3:374–385 (1962).

Gyermek, L., "Neuropharmacology of a potent, naturally occurring steroid hypnotic agent," *Fed. Proc.* 26:324 (1967).

Gyermek, L., "Pregnanolone: A Highly Potent, Naturally Occurring Hypnotic—Anesthetic agent," *Proc. Soc. Exper. Biol. Med.* 125:1058–1062 (1967).

Gyermek, L. and Soyka, L. F., "Steroid Anesthetics," *Anesthesiology* 42 (3):331–343 (1975).

Gyermek et al., "Steroids. CCCX. Structure–activity Relationship of Some Steroidal Hypnotic Agents," *J. Med. Chem.* 11:117–125 (1968).

Halsey et al., "Pressure Reversal of the effects of alphazalone/alphadolone and methohexitone in tadpoles: evidence for different molecular sites for general anesthesia," *Br. J. Pharmacol.* 89 (2):299–305 (1986).

Harrison et al., "Structure—Activity Relationships for Steroid Interaction with the γ–Aminobutyric Acid$_A$ Receptor Complex," *J. Pharmacol. Exp. Ther.* 241:346–353 (1987).

Hewett et al., "Anticonvulsant and intraneuronal blocking activity in some synthetic amino–steroids," *J. Pharm. Pharmacol.* 16:765–767 (1964).

Høgskilde et al., "Anticonvulsive Properties of Pregnanolone Emulsion Compared with Althesin and Thiopentone in Mice," *Br. J. Anaesth.* 61:462–467 (1988).

Hughes et al., "Chlordiazepoxide Effects on Reactions to Novelty and Activity With and Without Prior Drug Experience," *Psychopharmacologia* 42:289–292 (1975).

Kaspar, E. and Wiechert, R., "The action of haloform on the steroid–carbonyl function," *Chem. Abstr.* 53:8201b–8202b (1959).

Kasper, E. and Wiechert, R., "Über die Einwirkung von Haloform auf Steroidcarbonylfunktionen," *Chem. Ber.* 91:2664–2670 (1958).

Laidlaw, J., "Catamenial Epilepsy," *The Lancet*, pp. 1235–1237 (Dec. 15, 1956).

Lambert et al., "Acctions of Synthetic and Endogenous Steroids on the GABA$_A$ Receptor," *Trends in Pharm. Sci.* 8:224–227 (1987).

Landgren et al., "The effect of progesterone and its metabolites on the interictal epileptiform discharge in the cat's cerebral cortex," *Acta Physiol. Scand.* 131:33–42 (1987).

Lawrence et al., "Benzodiazepine Anticonvulsant Action: Gamma–aminobutyric Acid—Dependent Modulation of the Chloride Ionophore," *Biochem. Biophys. Res. Comm.* 123:1130–1137 (1984).

Lewbart, M. L. and Schneider, J. J., "Preparation and Properties of Steroidal 17,20–and 20,21–Acetonides Epimeric at C–20," *J. Org. Che.* 34 (11): 3505–3512 (1969).

Lewbart, M. L. and Schneider, J. J., "Preparation of Six 20–Deoxy Steroids in the 3α–Hydroxy–5β–pregnane Series and Their Use in Optical Rotation Studies," *J. Org. Chem.* 33(5):1707–1715 (1968).

Lister, R. G., "Ethologically–based Animal Models of Anxiety Disorders," *Pharmacol. Ther.* 43:321–340 (1990).

Lloyd, K. G. and Morselli, P. L., "Psychopharmacology of GABAergic Drugs," in: Psychopharmacology: The Third Generation of Progress, H. Y. Meltzer, ed., Raven Press, N.Y., pp. 183–195 (1987).

Maddocks et al., "A Double—blind Placebo—controlled Trail of Progesterone Vaginal Suppositories in the Treatment of Premenstrual Syndrofme," *Am. J. Obstet. Gynecol.* 154:573–581 (1986).

Majewska et al., "Steroid Hormone Metabolites Are Barbiturate–Like Modulators of the GABA Receptor," *Science* 233:1004–1007 (1986).

Majewska et al., "Steroids and Brain Activity," *Biochem. Pharmacol.* 36(22):3781–3788 (1987).

Maksay et al., "Dissociation of [35S]t–butylbicyclophosphorothionate Binding Differentiates Convulsant and Depressant Drugs that Modulate GABAergic Transmission," *J. Neurochem.* 44:480–486 (1985).

Marker et al., "Sterols. IX. Isolation of epi–Pregnanol–3–one–20 from Human Pregnancy Urine," *J. Amer. Chem. Soc.* 59:616–618 (1937).

Marrian, G. F. and Gough, N., "The Isolation of Pregnane—3(α)—ol—20—one from the Hydrolysis Products of Sodium Pregnanediol Glucuronidate," *Biochem. J.* 40:376–380.

Marshall, C. W., "5–Pregnen–3β–ol–20–one 3–aminoalkanoates," *Chem. Abstracts* 59:12883 Abstract No. 12883c (1963).

Mattson et al., "Medroxyprogesterone Therapy for Catamenial Epilepsy," *Advances in Epileptology*, vol. 15, Porter et al., eds., Washington, D. C., Sep. 26–30, 1983, Raven Press, N. Y., pp. 279–282 (1984).

Mendelson et al., "Sleep induction by an adrenal steroid in the rat," *Psychopharmacology* 93:226–229 (1987).

Mok, W. M. and Krieger, N. R., "Evidence that 5α–pregnan–3α–ol–20–one is the metabolite responsible for progesterone anesthesia," *Brain Res.* 533:42–45 (1990).

Morel, F. and Bastide, F., "Relationship Between the Structure of Several Analogues of Oxytocin and Their 'Natriferic' Activity in Vitro," *Proc. Intl. Pharmacol. Meeting*, 2nd, Prague, Vol. 10, 1963, pp. 47–55 (1964).

Morrow et al., "Steroid hormone metabolites potentiate GABA receptor–mediated chloride ion flux with nanomolar potency," *Eur. J. Pharmacol.* 142:483–485 (1987).

Munari et al., "The Use of Althesin in Drug–Resistant Status Epilepticus," *Epilepsia* 20:475–483 (1979).

Notari, R. E., "Theory and Practice of Prodrug Kinetics," *Meth. Enzymol.* 112:309–323 (1985).

Oh'uchi et al., "On the Structure of the Hot Acid Hydrolysis Products of 3α, 20α–Disulpho–oxy–5α–pregnanem" *Chem. Pharm. Bull.* 26(7):2262–2265 (1978).

Pfaff, D. W. and McEwen, B. S., "Actions of Estrogens and Progestins on Nerve Cells," *Science* 219:808–814 (1983).

Phillipps, G. H., "Structure–Activity Relationships in Steroidal Anaesthetics," *J. Steroid Biochem.* 6:607–613 (1975).

Pulis et al., "Some 3–phenyl derivatives of pregnane–11, 20–dione," *Chem. Abstracts* 58:12623 Abstract No. 12623e (1964).

Purdy et al., "Synthesis, Metabolism, and Pharmacological Activity of 3 Alpha—Hydroxy Steroids which Potentiate GABA—receptor—mediated Chloride Ion Uptake in Rat Cerebral Cortical Synaptoneurosomes," *J. Med. Chem.* 33:1572–1581 (1990).

Raisinghani et al., "Uptake of Intravenously Administered Progesterone, Pregnanedione and Pregnanolone by the Rat Brain," *Acta Endocrinologica* 57:395–404 (1968).

Rosciszewska et al., "Ovarian Hormones, Anticonvulsant Drugs, and Seizures During the Menstraula Cycle in Woman with Epilepsy," *J. Neurol. Neurosurg. Psych.* 49:47–51 (1986).

Ross, S. B., "Pharmacological and toxicological exploitation of amine transporters," *TIPS* 8:227–231 (1987).

Roussel–UCLAF, "Antispasmodics," *Chem. Abstracts* 59:12877 Abstract No. 12877g (1963).

Sansone, M., "Effects of Repeated Administration of Chlordiazepoxide on Spontaneous Locomotor Activity in Mice," *Psychopharmacology* 66:109–110 (1979).

Selye, H., "The Antagonism Between Anesthetic Steroid Hormones and Pentamethylenetetrazol (Metrazol)," *J. Lab. Clin. Med.* 27:1051–1053 (1942).

Selye, H., "Correalations Between the Chemical Structure and the Pharmacological Actions of the Steroids," *Endocrinology* 30:437–453 (1942).

Squires et al., "[35S]t—Butylbicyclophosphorothionate Binds with High Affinity to Brain—specific Sites Coupled to Gamma—Aminobutyric Acid—A and Ion Recognition Sites," *Molec. Pharmacol.* 23:326–336 (1983).

Sugrue, M. F., M.Sc. Thesis (1963).

Swinyard, E. A. and Woodhead, J. H., "Experimental Detection, Quantification, and Evaluation of Anticonvulsants," in: Antileptic Drugs, Woodbury etal., eds., Raven Press, N.Y., pp. 111–126 (1982).

Syntex S. A., "3—Alkoxy—19—nor—2,5(10—androstadien—17—ones," *Chem. Abstracts* 56:8800 Abstract No. 8800c (1962).

Treit, D., "Animal Models for the Study of Anti—anxiety Agents: A Review," *Neurosci. Biobehav. Rev.* 9:203–222 (1985).

Vogel et al., "Attenuation of the Effect of Punishment by Throtropin–releasing Hormone: Comparisons with Chlordiazepoxide," *J. Pharmacol. Exp. Ther.* 212:153–161 (1980).

Vogel., "A Simple and Reliable Conflict Procedure for Testing Anti–anxiety Agents," *Psychopharmacologia* 21:1–7 (1971).

Wardley–Smith, B. and Little, H. J., "In Vivo Interactions Between the Benzodiazepine Antagonist Ro 15–1788 and the Steroid Anaesthetic Althesin in Rats," *Br. J. Anaesth.* 57:629–633 (1985).

Wardley–Smith et al., "Lack of Correlation Between the Anesthetic and Anti–Convulsant Potencies of Althesin, Ketamine and Methohexitone," *Br. J. Anaesthp.* 60:140–145 (1988).

Wechter, W. J., "3,11—Dioxygenated—17—deoxy—5β—androstanes," *Chem. Abstacts* 61:4433f–4434c (1964).

Werboff et al., "Audiogenic Seizures in Adult Male Castrated Rats Treated with Various Hormones," *Gen. Comparative Endocrinology* 3:389–397 (1963).

Wiebe et al., "Syntheis of the Allylic Gonadal Steroids, 3α–Hydroxy–4–androsten–17–one, and of 3α–Hydroxy–5α–pregnane–20–one," *Steroids* 45(1):39–51 (1985).

Wiechert et al., "Haloform adducts of 3—oxo steroids," *Chem. Abstracts* 55:3658h–3659g (1961).

Wood et al., "In Vitro Characterization of Benzodiazepine Receptor Agonists, Antagonists, Inverse Agonists and Agonist/Antagonists," *J. Pharmacol. Exp. Ther.* 231:572–576 (1984).

Woodbury, D. M., "Effect of Adrenocortical Steroids and Adrenocorticotrophic Hormone on Electroshock Seizure Threshold," *JPET* 105:27–36 (1952).

Woodbury, D. M., "Effect of Hormones on Brain Excitability and Electrolytes," *Recent Progress Horm. Res.* 10:65–107 (1954).

Worms et al., "Gamma—Aminobutyric Acid (GABA) Receptor Stimulation. I. Neuropharmacological profiles of Progabide (SL 76002) and SL 75102 with Emphasis on their Anticonvulsant Spectra," *J. Pharmacol. Exp. Ther.* 220:660–671 (1982).

Wovkulich et al., "Steroselective Introduction of Steroid Side Chains. Synthesis of Chenodeoxycholic Acid," *Helvetica Chimica Acta* 67:612–615 (1984).

Yoshizawa et al., "Confirmation of the Involvement of $C_{20}$—Carbonium Cation during the Hot Acid Hydrolysis of Pregnanediol Disulfate," *Chem. Pharm. Bull.* 30(12): 4325–4333 (1982).

Yoshizawa et al., "Mechanism of the D–Homoannulation of Pregnanediol Disulfate in Refluxing 3N Hydrochloric Acid," *Chem. Pharm. Bull.* 31:3819–3828 (1983).

Yoshizawa et al., "Migration of Deuterium to C–20 in the Rearrangement Reaction of 17α–Deuterated 5α–Pregnane–3α, 20α—diol Disulfate by Hot Acid Hydrolysis to 17α—Ethyl—17β–methyl–5αandrost–13(14)–en–3α–0l," *Chem. Pharm. Bull.* 26(7):2281–2283 (1978).

Cocker, J. D. et al., "Action of Some Steroids on the Central Nervous System of the Mouse. I. Synthetic Methods", *J. Med. Chem.* 8(4):417–425 (Jul. 1965).

Kaspar et al. "On the Action of Haloform on Steroid Carbonyl Groups," *chem. Ber.* 91:2664–2670 (1958), translation of Kaspar et al., Uber die Einwirkung von Haloform auf Steroidcarbonylfunktionen, *Chem. Ber.* 91:2664–2670 (1958).

METHODS, COMPOSITIONS, AND COMPOUNDS FOR ALLOSTERIC MODULATION OF THE GABA RECEPTOR BY MEMBERS OF THE ANDROSTANE AND PREGNANE SERIES

This application is a continuation of application Ser. No. 745,216, filed Aug. 13, 1991, now U.S. Pat. No. 5,232,917, which is a continuation-in-part of application Ser. No. 521,724, filed May 10, 1990, now U.S. Pat. No. 5,120,723, which is in turn a continuation-in-part of application Ser. No. 379,047, filed Jul. 13, 1989, abandoned, which in turn is a continuation-in-part of application Ser. No. 089,362 filed Aug. 25, 1987, now abandoned. These patents, applications and their claims and figures are incorporated herein by reference.

BACKGROUND OF THE INVENTION

The present invention is directed to a method, compositions, and compounds for modulating animal brain excitability via the gamma-aminobutyric acid (GABA) receptor-chloride ionophore complex (GR complex).

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −80 mV, the cell interior being negative with respect to the cell exterior. The potential (voltage) is the result of ion ($K^+$, $Na^+$, $Cl^-$, organic anions) balance across the neuronal semi-permeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −80 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GR complex, the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GR complex to facilitate the flow of chloride ions down an electrochemical gradient of the GR complex into the cell. An intracellular increase in the levels of this anion causes hyperpolarization of the transmembrane potential, rendering the neuron less susceptible to excitatory inputs (i.e., reduced neuron excitability). In other words, the higher the chloride ion concentration, the lower the brain excitability (the level of arousal).

It is well-documented that the GR complex is responsible for the mediation of anxiety, seizure activity, and sedation. Thus, GABA and drugs that act like GABA or facilitate the effects of GABA (e.g., the therapeutically useful barbiturates and benzodiazepines (BZs) such as Valium) produce their therapeutically useful effects by interacting with specific regulatory sites on the GR receptor complex.

It has also been observed that a series of steroid metabolites interact with the GR receptor complex to alter brain excitability (Majewska, M. D. et al., "Steroid hormone metabolites are barbiturate-like modulators of the GABA receptor," *Science*, 232:1004–1007, 1986; Harrison, N. L. et al., "Structure-activity relationships for steroid interaction with the gamma-aminobutyric acid-A receptor complex," *J. Pharmacol. Exp. Ther.*, 241:346–353, 1987). Prior to the present invention, the therapeutic usefulness of these steroid metabolites was not recognized by workers in the field owing to an incomplete understanding of the potency and site of action. Applicants' invention relates in part to a pharmaceutical application of the knowledge gained from a more developed understanding of the potency and site of action of certain steroid compounds.

The ovarian hormone progesterone and its metabolites have been demonstrated to have profound effects on brain excitability (Backstrom, T. et al., "Ovarian steroid hormones: effects on mood, behavior and brain excitability," *Acta Obstet. Gynecol. Scand. Suppl.* 130:19–24, 1985; Pfaff, D. W. and McEwen, B S., "Actions of estrogens and progestins on nerve cells," *Science* 219:808–814, 1983; Gyermek, et al., "Structure activity relationship of some steroidal hypnotic agents," *J. Med. Chem.* 11:117, 1968; Lambert, J. et al., "Actions of synthetic and endogenous steroids on the $GABA_A$ receptor," *Trends Pharmacol.* 8:224–227, 1987). The levels of progesterone and its metabolites vary with the phases of the menstrual cycle. It has been well documented that progesterone and its metabolites decrease prior to the onset of menses. The monthly recurrence of certain physical symptoms prior to the onset of menses has also been well documented. These symptoms, which have become associated with premenstrual syndrome (PMS) include stress, anxiety, and migraine headaches (Dalton, K., *Premenstrual Syndrome and Progesterone Therapy*, 2nd edition, Chicago: Chicago yearbook, 1984). Patients with PMS have a monthly recurrence of symptoms that are present in premenses and absent in postmenses.

In a similar fashion, a reduction in progesterone has also been temporally correlated with an increase in seizure frequency in female epileptics (i.e., catamenial epilepsy; Laidlaw, J., "Catamenial epilepsy," *Lancet*, 1235–1237, 1956). A more direct correlation has been observed with a reduction in progesterone metabolites (Rosciszewska et al., "Ovarian hormones, anticonvulsant drugs and seizures during the menstrual cycle in women with epilepsy," *J. Neurol. Neurosurg. Psych.* 49:47–51, 1986). In addition, for patients with primary generalized petit mal epilepsy, the temporal incidence of seizures has been correlated with the incidence of the symptoms of premenstrual syndrome (Backstrom, T. et al., "Endocrinological aspects of cyclical mood changes during the menstrual cycle or the premenstrual syndrome," *J. Psychosom. Obstet. Gynaecol.* 2:8–20, 1983). The steroid desoxycorticosterone has been found to be effective in treating patients with epileptic spells correlated with their menstrual cycles (Aird, R. B. and Gordan, G., "Anticonvulsive properties of desoxycorticosterone," *J. Amer. Med. Soc.* 145:715–719, 1951).

A syndrome also related to low progesterone levels is postnatal depression (PND). Immediately after birth, progesterone levels decrease dramatically leading to the onset of PND. The symptoms of PND range from mild depression to psychosis requiring hospitalization; PND is associated with severe anxiety and irritability. PND-associated depression is not amenable to treatment by classic antidepressants and women experiencing PND show an increased incidence of PMS (Dalton, K., 1984, op. cit.).

Collectively, these observations imply a crucial role for progesterone and its metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, et al., 1983, op. cit.; Dalton, K., 1984, op. cit.) has prompted the use of progesterone in their treatment (Mattson, et al., "Medroxyprogesterone therapy of catamenial epilepsy," in *Advances in epileptology: XVth Epilepsy International Symposium*, Raven Press, New York, 279–282, 1984, and Dalton, K., 1984, op. cit.). However, progesterone is not consistently effective in the treatment of the aforementioned syndromes. For example, no dose-response relationship exists for progesterone in the treatment of PMS (Maddocks, et al., "A double-blind placebo-controlled trial of progesterone vaginal suppositories in the treatment of premenstrual syndrome," *Obstet. Gynecol.* 154:573–581, 1986; Dennerstein, et al., *British Medical Journal*, 290:16–17, 1986).

The publications and references referred to above and hereafter in this specification are incorporated herein by reference.

SUMMARY OF THE INVENTION

The present invention is directed to methods, compositions, and compounds for modulating brain excitability. More particularly, the invention relates to the use of 3α-hydroxylated steroid derivatives, acting at a newly identified site on the GR complex, to modulate brain excitability in a manner that will alleviate stress, anxiety, insomnia, mood disorders (such as depression) that are amenable to GR-active agents, and seizure activity. Compositions and compounds effective for such treatment are within the scope of the invention.

The compounds used in and forming part of the invention are modulators of the excitability of the central nervous system as mediated by their ability to regulate chloride ion channels associated with the GABA receptor complex. Applicants' experiments have established that the compounds used in and of the invention have anticonvulsant and anxiolytic activity similar to the actions of known anxiolytic agents such as the BZs, but act at a distinct site on the GR complex.

The relationship of endogenous metabolites of progesterone to processes associated with reproduction (estrus cycle and pregnancy) is well established (Marker, R. E., Kamm, O., and McGrew, R. V., "Isolation of epi-Pregnanol-3-one-20 from human pregnancy urine," *J Am. Chem. Soc.* 59, 616–618, 1937). Prior to the present invention, however, it was not recognized how to treat disorders by modulating brain excitability through the use of progesterone metabolites. Therefore, this invention is directed to methods, compositions, and compounds to treat disorders by modulating brain excitability using the compounds of this invention. Representative disorders treated in the present invention are epilepsy, anxiety, pre-menstrual syndrome (PMS), post-natal depression (PND), mood disorders (such as depression) that are amenable to GR-active agents, and insomnia.

DETAILED DESCRIPTION OF THE INVENTION

The compounds of and used in the invention are various 3-hydroxylated-pregnan-20-ones; 3,21-pregnanediol-20-ones; 3,20-pregnanediols; and 3-hydroxylated-androstanes, and ester, ether, sulfonate, sulfate, phosphonate, phosphate, oxime, and thiazolidine derivatives thereof, which derivatives are referred to as prodrugs. The expression "prodrug" denotes a derivative of a known direct acting drug, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology*, 112:309–323 (1985); Bodor, N., "Novel Approaches in Prodrug Design," *Drugs of the Future*, 6(3):165–182 (1981); and Bundgaard, H., "Design of Prodrugs: Bioreversible Derivatives for Various Functional Groups and Chemical Entities," in *Design of Prodrugs* (H. Bundgaard, ed.), Elsevier, N.Y. (1985). It should be noted that some of the synthetic derivatives forming part of the present invention may not be true prodrugs because, in addition to the above characteristics, they also possess intrinsic activity. However, for purposes of this application they will be referred to as prodrugs.

Our studies (Gee, K. W., et al., "GABA-dependent modulation of the Cl ionophore by steroids in rat brain," *European Journal of Pharmacology*, 136:419–423, 1987) have demonstrated that the 3-hydroxylated-5-reduced steroids used in the invention are orders of magnitude more potent than others have reported (Majewska, M. D., et al., 1986, op. cit. and Harrison, N. L., et al., 1987, op. cit.) as modulators of the GR complex. Majewska et al. and Harrison et al. teach that the 3-hydroxylated-5-reduced steroids are only capable of much lower levels of effectiveness. Our in vivo experimental data demonstrate that the high potency of these steroids allows them to be therapeutically useful in the modulation of brain excitability via the GR complex. The most potent steroids useful in the present invention include major metabolites of progesterone and deoxycorticosterone. These steroids can be specifically used to modulate brain excitability in stress, anxiety, insomnia, mood disorders (such as depression) that are amenable to GR-active agents, and seizure disorders in a therapeutically beneficial manner. Furthermore, we have demonstrated that these steroids interact at a unique site on the GR complex which is distinct from other known sites of interaction (i.e., barbiturate, BZ, and GABA) where therapeutically beneficial effects on stress, anxiety, sleep, mood disorders and seizure disorders have been previously elicited (Gee, K. W. and Yamamura, H. I., "Benzodiazepines and Barbiturates: Drugs for the Treatment of Anxiety, Insomnia and Seizure Disorders," in *In Central Nervous System Disorders*, pages 123–147, D. C. Horvell, ed., 1985; Lloyd, K. G. and Morselli, P. L., "Psychopharmacology of GABAergic Drugs," in *Psychopharmacology: The Third Generation of Progress*, pages 183–195, H. Y. Meltzer, ed., Raven Press, N.Y., 1987). These compounds are desirable for their duration, potency and oral activity (along with other forms of administration).

The steroid derivatives of this invention are those having the structural formula:

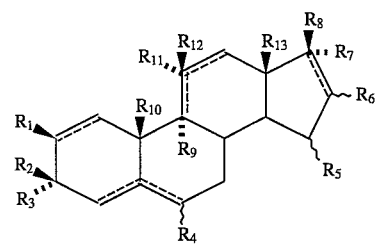

It is believed that R3 can be either hydroxyl, thiol or any ester due to the fact that the ester will be cleaved off as the prodrug is converted to drug form. These are referred to herein as cleavable esters.

Examples of substituents which can be used in these compounds are:

R1, R4, R5, and R6 are independently:

(1) hydrogen, hydroxyl or thiol; or (2) a pharmaceutically acceptable ether —Y—R14, wherein R14 is a $C_1$–$C_{10}$ saturated or unsaturated, halogenated or unhalogenated straight chain radical, or a $C_1$–$C_{10}$ saturated or unsaturated, halogenated or unhalogenated branched chain, or $C_3$–$C_{10}$ cyclic aliphatic radical, or $C_5$–$C_{10}$ aromatic radical, or $C_3$–$C_{10}$ heterocyclic radical having one or more 4, 5, 6, or 7 member saturated or unsaturated rings containing 1, 2, or 3 O, N, or S heteroatoms (where examples of heterocyclic radicals are: tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, ε-caprolactone, ε-caprolactam, omega-thiocaprolactam, and morpholine) and Y is either a divalent oxygen or sulfur linkage; or (3) a halogen atom; or (4) a $C_1$–$C_8$ saturated or unsaturated, halogenated or unhalogenated straight chain radical, a $C_1$–$C_8$ saturated or unsaturated, halogenated or unhalogenated branched chain, or $C_3$–$C_8$ cyclic aliphatic radical;

R2 is (1) a hydrogen; or (2) a halogen atom; or (3) a pharmaceutically acceptable ether —Y—R23, wherein R23 is a $C_1$–$C_4$ saturated or unsaturated, halogenated or unhalogenated straight chain radical, or a $C_1$–$C_4$ saturated or unsaturated, halogenated or unhalogenated branched chain radical, and Y is either a divalent oxygen or sulfur linkage; or (4) a $C_1$–$C_4$ saturated or unsaturated, halogenated or unhalogenated straight chain radical, or a $C_1$–$C_4$ saturated or unsaturated, halogenated or unhalogenated branched chain radical;

R3 is:

(1) hydroxyl or thiol; or (2) a pharmaceutically acceptable ester or thioester

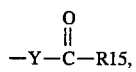

wherein R15 is hydrogen or a $C_1$–$C_{20}$ saturated, or unsaturated, halogenated or unhalogenated straight chain radical, or a $C_1$–$C_{20}$ saturated, or unsaturated, halogenated or unhalogenated branched chain radical, or $C_3$–$C_{10}$ cyclic aliphatic radical, or $C_5$–$C_{10}$ aromatic radical, or $C_3$–$C_{10}$ heterocyclic radical having one or more 4, 5, 6, or 7 member saturated or unsaturated rings containing 1, 2, or 3 O, N, or S heteroatoms, and Y is either a divalent oxygen or sulfur linkage. This ester is formed using reactions well known in the art between the hydroxyl group of the naturally occurring compounds discussed above with an organic acid, acid halide, acid anhydride, or ester, wherein the organic acids are for example: acetic, propionic, n- and i-butyric, n- and i- and s- and t-valeric, hexanoic, heptanoic, octanoic, nonanoic, decanoic, undecanoic, dodecanoic, cinnamic, benzylic, benzoic, maleic, fumaric, ascorbic, pimelic, succinic, bismethylene-salicylic, methanesulfonic, ethanesulfonic, oxalic, tartaric, acetyl salicylic, citric, gluconic, aspartic, stearic, palmitic, itaconic, glycolic, p-aminobenzoic, glutamic, benzenesulfonic, cyclohexyl-sulfamic, gamma-amino-butyric, α-(2-hydroxyethylamino)-propionic, phosphoric, phosphonic, sulfuric, sulfonic, glucuronic and 1-methyl-1,4-dihydro nicotinic, or thiocarboxylic acids thereof; or (3) a pharmaceutically acceptable cleavable ester of a natural or synthetic amino acid; or (4) a pharmaceutically acceptable acyloxyalkyloxy or acyloxyalkylthio

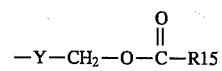

radical wherein Y and R15 are as previously defined. This acyloxyalkyloxy or acyloxyalkylthio embodiment is formed by the reaction of the 3-hydroxy or 3-thio group of the naturally occurring compounds discussed above by methods well known to the art with an organic acyloxyalkyl halide (1–20 carbons) or aryloxyalkyl halide, and, in particular, acetyl-oxy-methyl halide, diacetyloxymethyl halide, or aminoacetyloxymethyl halide;

R7 is (1) a hydrogen or a hydroxyl; or (2) a halogen atom; or (3) a pharmaceutically acceptable ether —Y—R23, wherein R23 is a $C_1$–$C_4$ saturated or unsaturated, halogenated or unhalogenated straight chain radical, or a $C_1$–$C_4$ saturated or unsaturated, halogenated or unhalogenated branched chain radical, and Y is either a divalent oxygen or sulfur linkage; or (4) a pharmaceutically acceptable $C_1$–$C_4$ saturated or unsaturated, halogenated or unhalogenated straight chain radical, or a $C_1$–$C_4$ saturated or unsaturated, halogenated or unhalogenated branched chain radical;

except when R8 is hydroxyl, R7 is not hydroxyl, and when C16–C17 is a double bond, R7 is not substituted;

R8 is:

(1) hydroxyl, thiol, acetyl

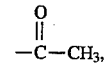

2-hydroxyethanoyl

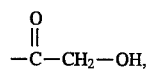

1-hydroxyethyl

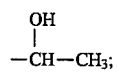

(2) a pharmaceutically acceptable ester or thioester

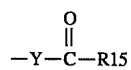

wherein R15 and Y are as previously defined; or (3) a pharmaceutically acceptable

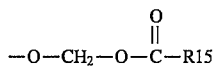

radical wherein R15 is as defined previously; or (4) a pharmaceutically acceptable

radical wherein R15 is as defined previously; or (5) a pharmaceutically acceptable

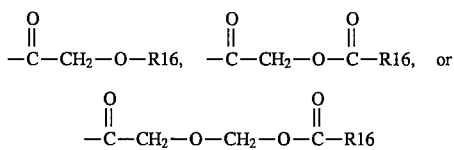

radical wherein each R16 is individually a $C_1$–$C_{10}$ saturated or unsaturated, halogenated or unhalogenated straight chain radical, or a $C_1$–$C_{10}$ saturated or unsaturated, halogenated or unhalogenated branched chain radical, or $C_3$–$C_{10}$ cyclic aliphatic radical, or $C_5$–$C_{10}$ aromatic radical, or $C_3$–$C_{10}$ heterocyclic radical having one or more 4, 5, 6, or 7 member saturated or unsaturated rings containing 1, 2, or 3 O, N, or S heteroatoms,
or an amide

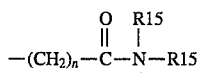

radical wherein n is 1–10, R15 is as previously defined, and each R15 is independently determined. An example of a compound of the present invention wherein R20 is an amide is 3α-hydroxy-5α-pregnan-21-(N,N-diethylsuccinamate)-20-one. These compounds are formed by reacting the 3,21-dihydroxylated pregnan-20-one in accordance with methods known in the art with an alkyl halide or organic acid, acid halide, acid anhydride, or ester, such as acetic, propionic, n- and i-butyric, n- and i- and s- and t-valeric, hexanoic, heptanoic, octanoic, nonanoic, decanoic, undecanoic, dodecanoic, cinnamic, benzylic, benzoic, maleic, fumaric, ascorbic, pimelic, succinic, bismethylenesalicylic, methanesulfonic, ethane-disulfonic, oxalic, tartaric, salicylic, citric, gluconic, aspartic, stearic, palmitic, itaconic, glycolic, p-aminobenzoic, glutamic, benzenesulfonic, cyclohexylsulfamic, gamma-amino-butyric, α-(2-hydroxyethylamino)-propionic, phosphoric, phosphonic, sulfuric, sulfonic, glucuronic and 1-methyl-1,4-dihydro nicotinic, or thiocarboxylic acids thereof; or (6) a pharmaceutically acceptable oxime

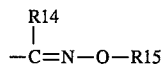

radical, wherein R14 and R15 are as previously defined, which may be prepared in accordance with known methods in the art; or (7) a pharmaceutically acceptable thiazolidine derivative of the 20-oxo position of a pregnone having the formula:

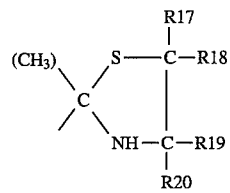

wherein any two of R17, R18, R19 and R20 are individually hydrogen or a $C_1$–$C_{10}$ saturated or unsaturated, halogenated or unhalogenated straight chain radical, or a $C_1$–$C_{10}$ saturated or unsaturated, halogenated or unhalogenated branched chain radical, or $C_3$–$C_8$ cyclic aliphatic radical, or $C_5$–$C_8$ aromatic radical, or $C_3$–$C_8$ heterocyclic radical having one or more 4, 5, 6, or 7 member saturated or unsaturated rings containing 1, 2, or 3 O, N, or S heteroatoms, and the remaining two of R17, R18, R19 and R20 are individually hydrogen; or R17, R18, R19 and R20 are individually

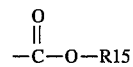

wherein R15 is as defined previously; or (8) a pharmaceutically acceptable

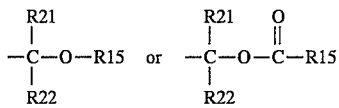

radical;
wherein at least one R21 and R22 are individually hydrogen or methyl and the other is hydrogen or a $C_1$–$C_{10}$ saturated or unsaturated, halogenated or unhalogenated straight chain radical, or a $C_1$–$C_{10}$ saturated or unsaturated, halogenated or unhalogenated branched chain radical, or $C_3$–$C_{10}$ cyclic aliphatic radical, or $C_5$–$C_{10}$ aromatic radical, or $C_3$–$C_{10}$ heterocyclic radical having one or more 4, 5, 6, or 7 member saturated or unsaturated rings containing 1, 2, or 3 O, N, or S heteroatoms, and R15 is as previously defined; or (9) a pharmaceutically acceptable carboxylate

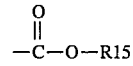

wherein R15 is as defined previously; or

(10) a pharmaceutically acceptable

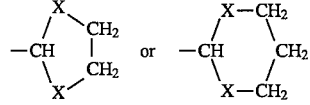

wherein each X independently is O, N, or S; or

(11) a pharmaceutically acceptable

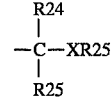

wherein R24 is hydrogen, or a $C_1$–$C_7$ saturated or unsaturated straight chain radical, or a $C_1$–$C_7$ saturated or unsaturated branched chain, or $C_3$–$C_{10}$ cyclic aliphatic radical, or $C_5-C_{10}$ aromatic radical, and R25 is a $C_1-C_7$ saturated or unsaturated straight chain radical, or a $C_1-C_7$ saturated or unsaturated branched chain, or $C_3-C_{10}$ cyclic aliphatic radical, or $C_5-C_{10}$ aromatic radical; or

(12) a cyano —C≡N;

R9 is hydrogen, an alkyl (preferably 1 to 6 carbons), an aryl (preferably 5 or 6 carbons), a halo-, dihalo-, or trihalo- (such as fluoro, chloro, bromo, or iodo) $C_{1-6}$ alkyl, or a halo-, dihalo-, or trihalo- (such as fluoro, chloro, bromo, or iodo) $C_{5-6}$ aryl; except if C8–C9 or C9–C11 is a double bond in which case R9 is not substituted;

R10 and R13 are hydrogen or an alkyl (preferably 1 to 8 carbons), $C_6$ aryl, halo (such as fluoro, chloro, bromo, or iodo), or dihalo or trihaloalkyl; or $C_6$ halo-, dihalo-, and trihaloaryl R11 and R12 are both hydrogen or one is hydrogen while the other is hydroxyl or thiol, alkyloxy or alkylthio (1 to 10 carbons), aryloxy or arylthio (1 to 10 carbons), or amino radical; or a saturated or unsaturated, halogenated or unhalogenated straight chain or branched chain (1–10 carbons) radical, or cyclic aliphatic (3–10 carbons) radical, or aromatic (5–10 carbons) radical, or heterocyclic (3–10 carbons) radical having one or more 4, 5, 6, or 7 member saturated or unsaturated rings containing 1, 2, or 3 O, N, or S heteroatoms; or R11 and R12 together make a double bond to oxygen or sulfur to form the ketone or thioketone; or R11 is selected from the group consisting of (1) a pharmaceutically acceptable

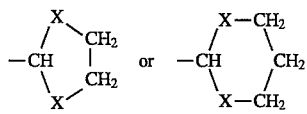

wherein each X independently is O, N, or S;

(2) a phamaceutically acceptable

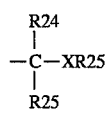

wherein R24 is hydrogen, or a $C_1-C_7$ saturated or unsaturated straight chain radical, or a $C_1-C_7$ saturated or unsaturated branched chain, or $C_3-C_{10}$ cyclic aliphatic radical, or $C_5-C_{10}$ aromatic radical, and R25 is a $C_1-C_7$ saturated or unsaturated straight chain radical, or a $C_1-C_7$ saturated or unsaturated branched chain, or $C_3-C_{10}$ cyclic aliphatic radical, or $C_5-C_{10}$ aromatic radical; except if C9–C11 is a double bond in which case R12 is not substituted.

In the compounds of the above formula [I], the bond at C1–C2 is either a single or a double bond. There can be single bonds at C4–C5 and $C_5$–C6 or a double bond at either C4–C5 or $C_5$–C6 while the other is a single bond. There can be single bonds at C8–C9 and C9–C11 or a double bond at either C8–C9 or C9–C11 while the other is a single bond. There can be a single or a double bond at C16–C17.

Typical alkyl groups used as R9, R10, and R13 are methyl, ethyl, propyl, butyl, octyl, t-butyl, and octa-decyl. Representative aryl groups are phenyl, benzyl, tolyl, and naphthyl. Typical trifluoroalkyl groups include trifluoromethyl and trifluoroethyl.

Representative alkyloxy groups for R11 and R12 include methoxy, ethoxy, propoxy, butoxy, octoxy, dodecoxy, and octadecoxy. Aryloxy groups useful as R11 and R12 moieties are phenoxy, tolyloxy, and the like.

Typical heterocyclic groups are radicals of 1-methyl-1,4-dihydronicotine, furan, thiophene, tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, ε-caprolactone, ε-caprolactam, omega-thiocaprolactam and morpholine.

The following preparations and examples are directed to the preparation of compounds forming part of and used in the present invention.

PREPARATION 1

3β-Hydroxy-5α-pregnan-20-one

A mixture of 3β-hydroxy-5-pregnen-20-one (980 mg, 316.5 g/m, 3.1 mmol) and 50 mg of 5% Pd/C in 50 mL of absolute ethyl alcohol was stirred under 1 atmosphere of hydrogen gas for 5 hours at room temperature. The reaction was filtered through a celite pad and the filtrate evaporated under reduced pressure to give 950 mg of 3β-hydroxy-5α-pregnan-20-one (96% yield).

PREPARATION 2

2α,3α-Epoxy-5α-pregnan-20-one

5α-pregnan-2-ene-20-one (3.05 g) in 50 mL of chloroform was treated with m-chloroperbenzoic acid (50–60%, 4.0 g). The solution was stirred at room temperature overnight (14 h) under an argon atmosphere. The solution was diluted with more chloroform (250 mL), washed with dilute potassium bicarbonate solution (2×150 mL), with water (2×100 mL), and finally with brine, and dried over magnesium sulfate and evaporated to an oil which crystallized on standing. Flash chromatography on a silica gel bed (200 g) and eluting with hexane/ethyl acetate (90:10) recovered in fraction 67–110 (collecting 20 mL volumes) 1.194 g of the title compound.

PREPARATION 3

5α-Pregnan-2-ene-20-one

3α-Hydroxy-5α-pregnan-20-one (5.12 g) in pyridine (40 mL) was treated with toluene-p-sulphonyl chloride (5.6 g), and the reaction mixture was stirred at room temperature for 18.0 h. This solution was poured into dilute (5%) hydrochloric acid (200 mL) and washed three times with chloroform (150 mL portions). The combined organic phase was extracted with more 5% hydrochloric acid and water, dried over magnesium sulfate and evaporated to an oil which on standing crystallized and gave 3α-toluene-p-sulphonyloxy-5α-pregnan-20-one as a white solid.

The crude product 3α-toluene-p-sulphonyloxy-5α-pregnan-20-one in 30 mL of collidine was refluxed for 1.0 h. The solution was allowed to cool and then poured into cold dilute hydrochloric acid (200 mL) and extracted three times with $CH_2Cl_2$ (100 mL portions). The combined organic phase was dried over magnesium sulfate and concentrated. Flash chromatography on a silica gel bed (100 g) and elution with hexane/ethyl acetate (80:20) gave 4.65 g (97% yield for the two steps) of 5α-pregn-2-ene-20-one.

PREPARATION 4

3α-t-butyldimethylsilyloxy-5α-androstan-17-one

To 3α-hydroxy-5α-androstan-17-one (25.22 g, 290.5 g/mol, 86.8 mmol) dissolved in 65 mL of dry pyridine was added 65 mL of dry dimethylformamide, imidazole (14.77 g, 68.1 g/mol, 217 mmol), and t-butyldimethylsilylchloride (16.36 g, 151 g/mol, 109 mmol), and the reaction was allowed to stand at room temperature for 12 hours. The reaction mixture was then partitioned between 220 mL of water and 220 mL of ethyl acetate and the combined organic layers were washed with water and dried over anhydrous sodium sulfate. The solvent was removed in vacuo and absolute ethanol was added with cooling to −20° C. to give the titled compound (32 g, 91% yield).

PREPARATION 5

3α-t-butyldimethylsilyloxy-(5α)-cis-pregn-17(20)-ene

To potassium-t-butoxide (93 mL, 93 mmol, 1M solution) in 161 mL of THF was added (ethyl)triphenylphosphonium bromide (35.4 g, 371.3 g/mol, 95 mmol), and 3α-t-butyldimethylsilyloxy-5α-androstan-17-one (10 g, 404.78 g/mol, 25 mmol). The orange-red colored reaction mixture was degassed under argon and refluxed for 10 hr. the reaction was then cooled to room temperature and poured into 350 mL of ice water. The mixture was extracted twice with 350 mL of ether and the combined organic layers were washed with 700 mL of water and dried over anhydrous magnesium sulfate. The solvent was removed to give an oil which was crystallized from ethanol to give the titled compound (9.3 g, 416.8 g/mol, 90% yield).

PREPARATION 6

(3R)-5α-pregnan-3-spiro-2'oxirane-20-one

To a stirred solution of trimethyl-sulfoxonium iodide (5.290 g, 24.04 mmol) in DMSO (75 mL) at room temperature was added NaH (97%; 488 mg, 19.72 mmol) in one portion. The resulting mixture that became a clear solution after ~10 min was stirred at room temperature under a nitrogen atmosphere for 1 h. Then a suspension of 5α-pregnan-3,20-dione (1.538 g, 4.860 mmol) in DMSO (40 mL+10 mL for the rinse) was added dropwise through a pressure-equalizing funnel. The mixture so obtained, which was not completely clear, was stirred at room temperature under a nitrogen atmosphere for a total of 2.5 h although TLC (3:1 hexane/EtOAC) after 1.5 h showed complete disappearance of the starting material. The mixture was then poured into ice/water and extracted with ether (×3). The combined organic phase was washed with water (×3) and brine, dried (MgSO$_4$), filtered, and evaporated under reduced pressure to give a solid. Finally, recrystallization from hot 1:1 methanol/acetone (~50 mL) gave the epoxide (1.176 g, 73%) as whte crystals.

EXAMPLE 1

3β,21-Dihydroxy-5α-pregnan-20-one 21-acetate

3β-Hydroxy-5α-pregnan-20-one (3.15 g, 9.9 mmol) was stirred for 4 hours at room temperature with lead tetraacetate (4.7 g, 10 mmol) in benzene (127 mL) and methanol (7 mL) containing boron trifluoride etherate (18.5 mL). The product was extracted with chloroform and isolated after aqueous workup. The organic phase was washed twice with 10% sodium bicarbonate, dried over magnesium sulfate, and finally concentrated to a solid. This crude solid product was recrystallized from ethyl acetate and petroleum ether (30°–60° C.) to give 2.0 g (56% yield) of 3β,21-dihydroxy-5α-pregnane-20-one 21-acetate.

EXAMPLE 2

3α,21-Dihydroxy-5α-pregnan-20-one 3,21-diacetate

To a stirred mixture of 3β,21-dihydroxy-5α-pregnane-20-one 21-acetate (500 mg, 1.32 mmol) in 40 mL of freshly distilled THF was added triphenylphosphine (366 mg, 262.3 g/m, 1.39 mmol) and glacial acetic acid (0.09 mL, 1.5 mmol). To this stirred mixture at room temperature under nitrogen atmosphere was introduced, over a period of 45 minutes, a solution of diisopropylazidodicarboxylate (DIAD) (0.275 mL, 1.027 g/ml, 202.2 g/m, 1.39 mmol) in 10 mL of THF. The combined reaction mixture was stirred for 2.0 hours before the solvent was removed under reduced pressure. The crude product was chromatographed (using the flash technique method on a column of 4 inches of silica gel) with hexane/ethyl acetate (7:3) to give 460 mg (86% yield) of 3α,21-dihydroxy-5α-pregnane-20-one 3,21-diacetate as a white solid.

EXAMPLE 3

3α,21-Dihydroxy-5α-pregnan-20-one

A mixture of 3α,21-dihydroxy-5α-pregnane-20-one 3,21-diacetate (1.00 g, 418.5 g/m, 2.39 mmol) in 40 mL of methanol was cooled to 0° C. with an ice bath. Perchloric acid, 70.0% (10.0 mL, 0.116 mole) was added dropwise to the mixture. After the addition of perchloric acid was completed, the reaction mixture was allowed to stir at 0° C. for an additional 30 min. and the water ice bath was removed. The mixture was left stirring at room temperature for 22 hours. The reaction mixture was poured into water (250 mL) and the white solid was filtered and washed with water until the filtrate is pH 7. The solid was recrystallized from hexane:ethyl acetate (60:40) to give 0.725 g (90.7%, 334.5 g/m) of 3α,21-dihydroxy-5α-pregnan-20-one.

EXAMPLE 4

3α-Acetoxy-5α-pregnan-20-one

To a stirred solution of 3β-hydroxy-5α-pregnan-20-one (4.5 g, 318.5 g/m, 14 mmol) in 150 mL of freshly distilled THF, triphenylphosphine (5.58 g, 262.3 g/m, 21 mmol), and acetic acid (1.22 mL) were added. To this stirred reaction mixture at room temperature was added a solution of diisopropylazidodicarboxylate (DIAD) (4.18 mL, 1.027 g/ml, 202.2 g/m, 21 mmol) in 75 mL of tetrahydrofuran dropwise over a period of 10 minutes. After 30 min., the reaction mixture was concentrated under reduced pressure and redissolved in 100 mL of chloroform and extracted twice with water. The chloroform extract was dried over magnesium sulfate and evaporated. The product residue was purified by flash chromatography on silica gel with a mixture of hexane/ethyl acetate (9:1). Fractions corresponding to the title compound were concentrated to give 4.95 g (97.5%) of 3α-acetoxy-5α-pregnan-20-one as a white solid.

EXAMPLE 5

3α-Hydroxy-5α-pregnan-20-one

3α-acetoxy-5α-pregnan-20-one (4.8 g) in 150 mL of methanol was cooled to 0° C. with an ice bath and 15.0 mL of perchloric acid was added dropwise. After 30 m of stirring, the ice bath was removed and the reaction mixture was left stirring for three days. The reaction mixture was poured into water and extracted with chloroform three times. The chloroform extracts were combined, dried over magnesium sulfate, and the solvent evaporated to give 4.57 g of crude product.

EXAMPLE 6

3α-(N-[2-Hydroxyethyl]-DL-alanyloxy)-5α-pregnan-20-one hydrochloride

A solution of 3α-hydroxy-5α-pregnan-20-one (810 mg, 2.45 mmol) in 100 mL of $CH_2Cl_2$ was treated with 2-bromopropionyl chloride (1.0 mL), a catalytic amount of dimethylaminopyridine (50 mg) and triethylamine (2 mL). This mixture was stirred at room temperature for 2.0 h. The crude reaction mixture was poured into water and $CH_2Cl_2$. The organic phase was washed several times with 10% HCl, water, saturated aqueous sodium bicarbonate and finally with more water, and dried and evaporated in vacuo. The TLC examination of this material indicated complete conversion of the starting material to bromo ester product (one spot, r.f.=0.9 eluting with Hexane/EtOAc (90:10)). This crude bromo ester in acetonitrile (30 mL) was treated at 0° C. with 2-hydroxyethylamine (2.0 mL) and the mixture stored in the refrigerator overnight. The solvent was removed in vacuo and the residue partitioned between ether and water. The organic phase was separated and extracted with cold 10% HCl. The aqueous acid solution was washed with ether and treated with an excess of aqueous ammonium hydroxide solution at 0° C. The free based product was next extracted into an organic phase with several ether washings. The combined organic phase was concentrated in vacuo and the oily residue dissolved in dioxane and taken to pH 3 with concentrated hydrochloric acid gas dissolved in EtOAc. The mixture was lyophilized and the resulting white amorphous solid taken up in water and the aqueous phase washed with ethyl acetate and ether. The aqueous solution was lyophilized to give the pure title compound (700 mg) as an amorphous solid.

EXAMPLE 7

3α-Hydroxy-5α-androstane-17β-carboxylic acid

A solution of sodium hydroxide (1.1 g) in water (18 mL) was stirred at −5° C. and bromine (0.4 mL) was added very slowly. Cold dioxane (12 mL) was added and the resulting sodium hypobromite solution was added to a solution of 3α-hydroxy-5α-pregnane-20-one (0.6 g) in dioxane (30 mL) at 0° C. The resulting mixture was kept at this temperature for 1 hr., neutralized with concentrated hydrochloric acid and poured into water. Excess 2N hydrochloric acid was then added and the precipitated solid was collected by filtration and dried in vacuo which gave the title compound.

EXAMPLE 8 a. 3α-Acetoxy-17α-bromo-5α-pregnan-20-one:

3α-Acetoxy-5α-pregnan-20-one (3 g, 360.5 g/m, 8.3 mmol), N-bromosuccinimide (2.7 g, 178 g/m, 15 mmol), and benzoyl peroxide (200 mg, 242 g/m, 0.83 mmol) dissolved in 50 ml of carbon tetrachloride were refluxed overnight (ca. 16h). The reaction mixture was cooled, filtered, and washed with sodium bisulfite, water, and brine, and then concentrated to give a crude reddish oil.

b. 3α-Acetoxy-5α-pregn-16-en-20-one:

The reddish oil above was dissolved in 150 mL of benzene and 2 mL of 1,5-diazabicyclo[5.4.0]undec-5-ene (DBU, 152 g/m, 1.02 g/mL, 13.4 mmol) and then refluxed for 16 h. DBU (2 ml) was added and reflux continued for 4 days. The solvent was removed in vacuo and the residue taken up in ether and washed with 1N HCl, dried over magnesium sulfate and concentrated to give the crude oily product. This was purified by filtration through a bed of silica gel with hexane/ethyl acetate (10:1.5) elution. Product was recovered in the middle fractions to give 1.1 g of a yellow product (358.5 g/m, 3.1 mmol, 37% overall).

EXAMPLE 9

(20S)3α,20-Dihydroxy-pregnane

To a stirred solution of 3α-acetoxy-5α-pregn-16-en 20-one (970 mg, 358.5 g/m, 2.7 mmol) in 130 mL of dry isopropanol was added sodium metal (8.0 g, 23 g/m, 348 mmol) slowly in small portions over 1 hr. After refluxing for 1 hour an additional amount of sodium (3.5 g) was added and reflux continued for 1 hour. The reaction mixture was acidified with 10% HCl and extracted with chloroform. The organic phase was dried over magnesium sulfate and concentrated to give the crude product. Recrystallization from acetone with cooling in the freezer gave 80 mg of a mixture (93:7) of 20α and 20β respectively. Additional recrystallization from methanol resulted in the pure title product.

EXAMPLE 10

3α-Benzoyloxy-5α-pregnan-20-one

A mixture of 3β-hydroxy-5α-pregnan-20-one (285 mg, 318.5 g/m, 0.89 mmol), triphenylphosphine (258 mg, 262.3 g/m, 0.94 mmol), and benzoic acid (120 mg, 122.2 g/m, 0.98 mmol) was dissolved in 25 mL of tetrahydrofuran (freshly distilled). To this stirred reaction mixture at room temperature was added a solution of diisopropylazidodicarboxylate (DIAD) (0.194 mL, 1.027 g/ml, 202.2 g/m, 0.98 mmol) in 5 mL of tetrahydrofuran dropwise over a period of 5 minutes. The reaction was followed by thin layer chromatography (TLC) as the starting material was consumed. After two hours, the reaction mixture was concentrated under reduced pressure and filtered through a bed of silica gel (10 g) with a mixture of hexane/ethyl acetate (9:1). Fractions corresponding to the title compound were concentrated to give 349 mg of 3α-benzoyloxy-5α-pregnan-20-one (92% yield) as a white solid.

EXAMPLE 11

3α-Benzoyloxy-5α-pregnan-20-oxime

To a stirred mixture of 3α-benzoyloxy-5α-pregnan-20-one (300 mg, 422.62 g/m, 0.71 mmol) in 25 mL of ethyl alcohol is added a solution of hydroxylamine (23 mg, 33 g/m, 0.71 mmol) and sodium acetate (290 mg, 136 g/m, 2.1 mmol) in 5 mL of water. After refluxing for 6 hours, the reaction mixture is cooled and extracted with water and ethyl acetate. The organic phase is dried over magnesium sulfate and evaporated to dryness which gives 3α-benzoyloxy-5α-pregnan-20-oxime in ca. 80% yield.

EXAMPLE 12

3α-benzoyloxy-20-carboxymethyloxime-5α-pregnane

A solution of sodium (11.5 mg, 22.99 g/m, 0.5 mmol) and 3α-benzoyloxy-5α-pregnan-20-oxime (219 mg, 437.6 g/m, 0.5 mmol) in 25 mL of absolute ethyl alcohol is prepared. To this stirred mixture is added bromoacetic acid (73 mg, 137.9 g/m, 0.53 mmol) in one portion and the reaction is heated in a bath (80° C.) until the pH is below 7 as shown by a wet pH paper. The reaction mixture is evaporated, and the residue is extracted twice with 25 mL of tetrahydrofuran. The organic phase is dried over magnesium sulfate and concentrated to give α-(3α-benzoyloxy-5α-pregnan-20-ylideneaminooxy) acetic acid (ca. 80% yield).

EXAMPLE 13

3α-Hydroxy-5α-pregnan-20-one 3-hemisuccinate sodium salt

Succinic anhydride (280 mg) was added to a solution of 3α-hydroxy-5α-pregnan-20-one (200 mg) in dry pyridine (4 mL). The stirred solution was refluxed (oil bath temperature set at 140° C. for 4 h). The reaction mixture was cooled and poured into water and acidified with 10% hydrochloric acid and extracted several times with chloroform. The organic phase was washed with water, dried over magnesium sulfate and finally concentrated to an oil. The crude oil was recrystallized from hexane and ethyl acetate to give 3α-hydroxy-5α-pregnan-20-one 3-hemisuccinate (220 mg, 84% yield) as fine white crystals.

3α-hydroxy-5α-pregnan-20-one 3-hemisuccinate (108 mg) was dissolved in 15 mL of methanol and a solution of aqueous sodium bicarbonate (22 mg in i mL of water) was added. The solvent was removed under reduced pressure and the product was triturated with ether and ethyl acetate and finally dried to give 99 mg of the title compound as white solid.

EXAMPLE 14

3α,21-Dihydroxy-5α-pregnan-20-one 21-hemisuccinate sodium salt

A mixture of 3α,21-dihydroxy-5α-pregnan-20-one (234 mg) and succinic anhydride (70 mg) in 6 mL of anhydrous pyridine was stirred under nitrogen atmosphere at room temperature for 5 days. The reaction mixture was monitored by TLC for the disappearance of the starting material. The reaction mixture was poured into 5% hydrochloric acid and chloroform and the organic phase washed several times with dilute acid, water, and dried over magnesium sulfate. The solvent was removed in vacuo to give 3α,21-dihydroxy-5α-pregnan-20-one 21-hemisuccinate in quantitative yield (299 mg) as white solid.

The above hemisuccinate (84 mg) in 20 mL of methanol was treated with an aqueous solution of sodium bicarbonate (18 mg in 1.5 mL of water). The reaction mixture was concentrated in vacuo, washed with ether and then ethyl acetate, and evaporated to a constant weight to give the titled compound as a white solid.

EXAMPLE 15

3α,3'-Acetylsalicyloxy-5α-pregnan-20-one

To a stirred solution of triethylamine (5 mL) in methylene chloride (70 mL) at room temperature is dissolved 254 mg of 3α-hydroxy-5α-pregnan-20-one. This mixture is cooled in an ice bath and acetylsalicyloyl chloride (200 mg) is added. The ice bath is removed after 1 h, and the reaction mixture is stirred at room temperature for 18 h. The reaction is poured into an aqueous 10% sodium bicarbonate solution and more methylene chloride is added.

The organic phase is washed once more with bicarbonate, water, and it is then dried over magnesium sulfate, filtered, and evaporated.

EXAMPLE 16

3α-5'-Chlorobenzoyloxy-5α-pregnan-20-one

To an ice-cooled, stirred mixture of 3α-hydroxy-5α-pregnan-20-one (260 mg, 318.5 g/m, 0.82 mmol), triethylamine (0.17 mL), and 4-dimethylaminopyridine (DMAP catalytic, 10 mg, 122.17 g/m, 82 μmol) dissolved in 17 mL of dry dichloromethane under a nitrogen atmosphere was added 4-chlorobenzoyl chloride (161 mg, 174.9 g/m, 0.92 mmol). The reaction was stirred at 0° C. for 10 hours and then poured into 100 mL of 10% HCl and 200 ml of ether. The organic phase was washed once more with acid, twice with saturated sodium bicarbonate, and then dried over magnesium sulfate. After removal of solvent in vacuo, the crude product was purified by filtration through a bed of silica gel with hexane/ethyl acetate (15:35) elution. The product was isolated from the two earliest fractions (100 mL each) to give (317 mg, 457 g/m, 9.69 mmol, 84% ).

EXAMPLE 17

3α-pentafluoropropionyloxy-5α-pregnan-20-one

To an ice-cooled, stirred mixture of 3α-hydroxy-5α-pregnan-20-one (260 mg, 318.5 g/m, 0.82 mmol), triethylamine (0.17 mL), and 4-dimethylaminopyridine (DMAP catalytic, 10 mg, 122.17 g/m, 82 umol) dissolved in 17 mL of dry dichloromethane under a nitrogen atmosphere was added pentafluoropropionyl chloride (168 mg, 182.5 g/m 0.92 mmol). The reaction was stirred at 0° C. for 10 hours and then poured into 100 mL of 10% HCl and 200 mL of ether. The organic phase was washed once more with acid, twice with saturated sodium bicarbonate, and then dried over magnesium sulfate. After removal of solvent in vacuo, the crude product was purified by filtration through a bed of silica gel with hexane/ethyl acetate (15:35) elution. The product was isolated from the two earliest fractions (100 mL each) to give (330 mg, 464.5 g/m, 0.71 mmol, 87%).

EXAMPLE 18

3α-nicotinoyloxy-5α-pregnan-20-one

To 3α-hydroxy-5α-pregnan-20-one (464 mg, 318.5 g/m, 1.5 mmol) and 4-dimethylaminopyridine (DMAP, 195 mg, 122.17 g/m, 1.6 mmol) dissolved in 10 mL of dry pyridine was added nicotinoyl chloride hydrochloride (285 mg, 178.02 g/m, 1.6 mmol). The reaction mixture was heated at 90° C. for 5 hours and poured into 300 mL of ether. The organic layer was washed twice with saturated sodium bicarbonate, twice with water, dried over magnesium sulfate, and concentrated in vacuo to give the crude product. The crude material was filtered through a bed of silica gel using hexane/ethyl acetate (50:50) elution. The first two fractions gave the title compound (604 mg, 421 6/m, 1.43 mmol, 96%).

EXAMPLE 19

3α-N-methyl-nicotinoyloxy,5α-pregnan-20-one iodide

A mixture of 3α-nicotinoyloxy-5α-pregnan-20-one (770 mg, 421 g/m, 1.8 mmol) and methyliodide (3.0 mL, 141 g/m, –20 mmol) in 30 mL of acetone was refluxed gently for 17 hours. The reaction mixture was concentrated in vacuo to give the crude product.

EXAMPLE 20

3α-N-methyl-dihydronicotinoyloxy-5α-pregnan-20-one

To an ice cold solution of the 3α-N-methyl-nicotinoyloxy-5α-pregnan-20-one iodide salt (1.01 g, 562 g/m, 1.8 mmol) in 150 mL of aqueous methanol (100 mL methanol and 50 mL water, deaerated) was added sodium bicarbonate (620 mg, 84 g/m, 7.4 mmol) and sodium dithionite (1.3 g, 174 g/m, 7.4 mmol). This mixture was stirred at 0° C. for 1 h. The reaction mixture was poured into 500 mL of water and extracted several times with chloroform. The combined organic layers were washed with potassium carbonate and concentrated. The crude product was filtered through a bed of silica gel using hexane/ethyl acetate (5:1) elution. The product was recovered in the initial fractions to give 180 mg (439 g/m, 0.4 mmol, 22%).

EXAMPLE 21

3α-Isobutyloxy-5α-pregnan-20-one

To a stirred solution of 3β-hydroxy-5α-pregnan-20-one (8 g, 318.5 g/m, 25 mmol) in 200 mL of freshly distilled tetrahydrofuran (THF), triphenylphosphine (9.88 g, 262.3 g/m, 38 mmol), and isobutyric acid (3.5 mL) were added. To this stirred reaction mixture at room temperature was added a solution of diisopropylazidodicarboxylate (DIAD, 7.42 mL, 1.027 g/mL, 202.2 g/m, 38 mmol) in 75 mL of THF dropwise over a period of 10 minutes. The solution was stirred overnight. TLC indicated that the reaction was not complete. Triphenylphosphine (6.58 g), DIAD (4.94 mL), and isobutyric acid (2.33 mL) were added to the reaction and allowed to stir at room temperature for an additional 3 hours. TLC indicated complete reaction. The excess THF was evaporated and the residue was purified by column chromatography on silica gel with 90:10 hexane:ethyl acetate elution to give 7.3 g (346.5 g/m, 83.9%).

EXAMPLE 22

(20R)3α,20-Dihydroxy-5α-pregnane

To a stirred solution of 3α-hydroxy-5α-pregnan-20-one (3.2g, 318.5 g/m, 10 mmol) in 160 mL of methanol and 30 mL of dichloromethane at room temperature was slowly added sodium borohydride (3.3 g, 37.8 g/m, 87 mmol) over a period of 2 h. The mixture was stirred for an additional hour and then poured into ice cold water (700 mL) and extracted three times with ether. The combined organic phase was washed several times with water, dried over magnesium sulfate and concentrated to a white solid (2.35 g, 320.5 g/m, 7.3 mmol, 73%).

EXAMPLE 23

2β-Methoxy-3α-hydroxy-5α-pregnan-20-one

2α,3α-Epoxy-5α-pregnan-20-one (325 mg) in 80 mL of methanol was treated with a 1 mL solution of methanol containing 7 drops of concentrated sulfuric acid at room temperature. This mixture was stirred at this temperature for 10 minutes and then poured into a cold saturated solution of sodium bicarbonate and ether. The organic phase was washed several times with a small portion of bicarbonate, brine and dried over potassium carbonate. The concentrated organic phase was tested by TLC for complete reaction. Flash chromatography on silica gel with hexane/ethyl acetate solvent mixture (80:20) produced 209 mg (60% yield).

EXAMPLE 24

2β-Ethoxy-3α-hydroxy-5α-pregnan-20-one

2α,3α-Epoxy-5α-pregnan-20-one (180 mg) was dissolved in 20 mL of absolute ethanol and cooled to °C. and added to a cold 1.0 mL ethanol solution containing 3-drops of concentrated sulfuric acid. This reaction mixture was stirred for 30 minutes at this temperature and an additional 30 minutes at room temperature, poured into 20% sodium bicarbonate solution and washed several times with chloroform. The combined organic phase was dried over potassium carbonate and concentrated and purified by preparative TLC silica plate in hexane/ethyl acetate (1:1), to give (80 mg, 40% yield) the title compound as fine white crystals.

EXAMPLE 25

2β-Propyloxy-3α-hydroxy-5α-pregnan-20-one

2α,3α-Epoxy-5α-pregnan-20-one (360 mg) was dissolved in 80 mL of propanol and cooled to °C. and added to a cold 1.0 mL propanol solution containing 5-drops of concentrated sulfuric acid. This reaction mixture was stirred for 30 minutes at this temperature and an additional 30 minutes at room temperature, poured into a 20% sodium bicarbonate solution and washed several times with chloroform. The combined organic phase was dried over potassium carbonate and concentrated. Purification of the crude product on a silica gel column eluting with hexane/ethyl acetate (70:30) gave the titled compound (206 mg, 50% yield) as white crystals.

EXAMPLE 26 a. (3R)-20,20-Ethylenedioxy-5α-pregnan-3-spiro-2'oxirane-20-one

To a stirred solution of trimethyl sulphoxonium iodide (1.11 g) in 16 mL of dimethyl sulfoxide at room temperature was added 72 mg of sodium hydride (97%) under nitrogen atmosphere. This mixture was stirred for 1 h at this temperature. 20,20-Ethylenedioxy-5α-pregnan-3-one (300 mg) in 10 mL of dimethyl sulfoxide (as a suspension) was then added to the reaction mixture and stirred for 1.5 h. The mixture was poured into water and washed with ether. The organic phase was extracted repeatedly with water, brine and finally dried over magnesium sulfate. The solvent was removed under reduced pressure to give the title compound as a white solid (262 mg, 84%).

b. 3α-Hydroxy-3β-methyl-20,20-ethylenedioxy-5α-pregnane

A solution of dry THF (10 mL) containing (3R)-20,20-ethylenedioxy-5α-pregnan-3-spiro-2'-oxirane (262 mg. 374 g/m, 0.7 mmol) was added to a stirred solution of lithium aluminum hydride (133 mg, 37.9 g/m, 3.5 mmol, suspended in 10 mL of dry THF). Addition was complete in 30 min. at room temperature. Stirring was continued at reflux for 4 hours, then treated with ammonium chloride (100 mL) and extracted three times with ether. The combined organic phase was washed several times with water, dried over magnesium sulfate and concentrated to a white solid.

c. 3α-hydroxy-3β-methyl-5α-pregnan-20-one

A solution of 3α-hydroxy-3β-methyl-20,20-ethylenedioxy-5α-pregnane and p-toluene sulfonic acid (catalytic) in wet acetone was heated at reflux overnight. The reaction was concentrated in vacuo and taken up in chloroform. The organic phase was washed with sodium bicarbonate, dried over magnesium sulfate, concentrated, and recrystallized from methanol to give the title compound.

EXAMPLE 27

3α-hydroxy-3β-methyl-5α-pregnan-20-one

To a solution (light yellow) of the (3R)-5α-pregnan-3-spiro-2'-oxirane-20-one (101 mg, 0.305 mmol) and NaI (115 mg, 0.767 mmol) in anhydrous 1,2-dimethoxyethane (DME) (5mL) at room temperature was added n-Bu$_3$SnH (0.22 mL, 0.238 g, 0.818 mmol). The reaction solution became colorless. Azobisisobutylnitrile (AIBN) (10 mg, 0.061 mmol) was then added. The resulting solution was refluxed under a nitrogen atmosphere for 21 h. at which point TLC (3:1 hexane/acetone) indicated completion of the reaction. The reaction was quenched with methanol; the mixture was stirred at room temperature for a while. The solvent was removed in vacuo to give an oil which did not dissolve in ether. Addition of CH$_2$Cl$_2$ gave a solution which was washed with water, 1N HCl, and saturated NaHCO$_3$. The organic layer was dried (MgSO$_4$), filtered, and concentrated under reduced pressure to a white solid. Purification by gradient flash chromatography (hexane, 7:1 hexane/acetone, 5:1 hexane/acetone) furnished the titled compound (93mg, 92%).

EXAMPLE 28

3α,20-dihydroxy-3β,20-dimethyl-5α-pregnane

5α-pregnan-3,20-dione (1.5 g, 316.48 g/m, 4.7 mmol) was dissolved in 250 mL of dry benzene and 15 mL of 3M methylmagnesium bromide was added. The reaction mixture was stirred at room temperature for 30 min. The excess methyl magnesium bromide was decomposed by adding 100 mL of 1M H$_2$SO4 dropwise at 0° C. The product solution was extracted with 250 mL of diethylether. The organic extract was combined, dried over magnesium sulfate, and evaporated to give a 60:40 mixture of 3β-methyl and 3α-methyl isomers. The product mixture was separated by flash chromatography on silica gel using a 70:30 (hexane:ethyl acetate and 1% methanol) elution to give 0.476 g (24% yield) of the desired product.

EXAMPLE 29

3α,20-dihydroxy-20-methyl-5α-pregnane

To a stirred mixture of 3α-acetoxy-5α-pregnan-20-one (120 mg, 360.5 g/m, 0.32 mmol) in 25 mL of dry benzene, was added 4.6 mL of 3M methylmagnesium bromide dropwise. After the addition of methylmagnesium bromide was completed, the reaction mixture was allowed to stir at room temperature for 18 h and then refluxed for 2 h. The excess methylmagnesium bromide was decomposed by dropwise addition of 30 mL of saturated ammonium chloride solution in an ice bath. The solution product was poured into water and extracted with chloroform twice. The extracts were dried over magnesium sulfate and evaporated to give 110 mg of crude product. The product was recrystallized in methanol to give 83 mg of 3α,20-dihydroxy-20-methyl-5α-pregnane.

EXAMPLE 30

3α-hydroxy-(5α)-cis-pregn-17(20)-ene

3α-t-butyldimethylsilyloxy-(5α)-cis-pregn-17(20)-ene (3 g, 416.8 g/mol, 7.2 mmol) was dissolved in 50 mL of acetone containing 1% (v/v) concentrated HCl (37%) at 55° C. After 8 hr. at 55° C. the reaction mixture was diluted with cold acetone and crystallized at −20° C. to give the title compound (1.46 g, 302.5 g/mol, 67% yield).

It will be obvious to one skilled in the art that the above described compounds may be present as mixtures of diastereomers which may be separated into individual diastereomers. Resolution of the diastereomers may be conveniently accomplished by gas or liquid chromatography or isolation from natural sources. Unless otherwise specified herein, reference in the specification and claims to the compounds of the invention, as discussed above, is intended to include all isomers, whether separated or mixtures thereof.

Where isomers are separated, the desired pharmacological activity will often predominate in one of the diastereomers. As disclosed herein, these compounds display a high degree of stereospecificity. In particular, those compounds having the greatest affinity for the GABA receptor complex are those with 3α-substituted-5α-pregnane steroid skeletons. In addition, 3α-substituted-5β-pregnane, 3α-substituted-4-pregnene and 3α-substituted-16-pregnene skeletons have been demonstrated to be active. The preferred neuroactive steroids include 3α-hydroxy-2β-methoxy-5α-pregnan-20-one; 3α,21-dihydroxy-5α-pregnan-20-one; 3α,20α-dihydroxy-5α-pregnane; 3α,20-dihydroxy-20-methyl-5α-pregnane; 3α,20-dihydroxy-3β,20-dimethyl-5α-pregnane;

3α-hydroxy-3β-methyl-5α-pregnan-20-one; 3α-hydroxy-5α-pregnan-20-one; and 3α-isobutyryloxy-5α-pregnan-20-one.

The compounds of and used in the invention, that being the nontoxic, pharmaceutically acceptable, natural and synthetic, direct acting and "prodrug" forms of progesterone and androstane metabolites, have hitherto unknown activity in the brain at the GABA receptor complex. The present invention takes advantage of the discovery of this previously unknown mechanism and activity.

The compounds of the invention may be prepared by any suitable technique known in the art or henceforth developed. For example, the naturally occurring metabolites of progesterone may be extracted from various animal excretion sources, e.g., urine, or extracted from vegetable products like soy or yams. Such extractions are conducted using the following steps: (i) hydrolysis of the urine with HCl; (ii) extraction with toluene; (iii) removal of acidic material from the toluene extract; (iv) elimination of substances other than pregnanes from the neutral toluene-soluble fraction by precipitations from ethanolic solution with dilute NaOH and with water; and (v) weighing of the purified pregnanes obtained. See Marrian et al., "The Isolation of Pregnane-3α-ol-20-one," *Biochem.*, 40:376–380 (1947). These extracted compounds may then be chemically altered to form the desired synthetic derivative, or used directly.

The pharmaceutical compositions of this invention are prepared in conventional dosage unit forms by incorporating an active compound of the invention or a mixture of such compounds, with a nontoxic pharmaceutical carrier according to accepted procedures in a nontoxic amount sufficient to produce the desired pharmacodynamic activity in a subject, animal or human. Preferably, the composition contains the active ingredient in an active, but nontoxic amount, selected from about 5 mg to about 500 mg of active ingredient per dosage unit. This quantity depends on the specific biological activity desired and the condition of the patient. Desirable objects of the compositions and methods of this invention are in the treatment of stress, anxiety, PMS, PND, and seizures such as those caused by epilepsy (other than grand mal) to ameliorate or prevent the attacks of anxiety, muscle tension, and depression common with patients suffering from these central nervous system abnormalities. An additional desirable object of the composition and methods is to prevent insomnia and produce hypnotic activity.

The pharmaceutical carrier employed may be, for example, either a solid, liquid, or time release (see e.g. Remington's Pharmaceutical Sciences, 14th Edition, 1970). Representative solid carriers are lactose, terra alba, sucrose, talc, gelatin, agar, pectin, acacia, magnesium stearate, stearic acid, microcrystalline cellulose, polymer hydrogels and the like. Typical liquid carriers are propylene glycol, aqueous solutions of β-cyclodextrins, syrup, peanut oil, and olive oil and the like emulsions. Similarly, the carrier or diluent may include any time-delay material well known to the art, such as glycerol monostearate or glycerol distearate alone or with wax, microcapsules, microspheres, liposomes, and/or hydrogels.

A wide variety of pharmaceutical forms can be employed. Thus, when using a solid carrier, the preparation can be plain milled micronized, in oil, tableted, placed in a hard gelatin or enteric-coated capsule in micronized powder or pellet form, or in the form of a troche, lozenge, or suppository. When using a liquid carrier, the preparation can be in the form of a liquid, such as an ampule, or as an aqueous or nonaqueous liquid suspension. Liquid dosage forms also need pharmaceutically acceptable preservatives and the like. In addition, because of the low doses that will be required as based on the data disclosed herein, nasal spray, sublingual administration and timed release skin patches are also suitable pharmaceutical forms for topical administration.

The method of producing anxiolytic, anticonvulsant, mood altering (such as anti-depressant) or hypnotic activity, in accordance with this invention, comprises administering to a subject in need of such activity a compound of the invention, usually prepared in a composition as described above with a pharmaceutical carrier, in a nontoxic amount sufficient to produce said activity.

During menses, the levels of excreted metabolites vary approximately fourfold (Rosciszewska, et al., op. cit.). Therefore, therapy for controlling symptoms involves maintaining the patient at a higher level of progesterone metabolite than normal in the premenstrual state of PMS patients. Plasma levels of active and major metabolites are monitored during pre-menses and post-menses of the patient. The amount of the compounds of the invention administered, either singly or as mixtures thereof, are thus calculated to increase the levels of progesterone metabolite during the premenses state.

The route of administration may be any route that effectively transports the active compound to the GABA receptors that are to be stimulated. Administration may be carried out parenterally, enterally, rectally, intravaginally, intradermally, sublingually, or nasally; the oral and dermal routes are preferred. For example, one dose in a skin patch may supply the active ingredient to the patient for a period of up to one week.

Potency and Efficacy at the GR Site

The in vitro and in vivo experimental data show that the naturally-occurring metabolites of progesterone/deoxycorticosterone and their derivatives interact with high affinity at a novel and specific recognition site on the GR complex to facilitate the conductance of chloride ions across neuronal membranes sensitive to GABA (Gee et al., 1987).

To those skilled in the art, it is known that the modulation of [$^{35}$S]t-butylbicyclophosphorothionate ([$^{35}$S]TBPS) binding is a measure of the potency and efficacy of drugs acting at the GR complex, which drugs may be of potential therapeutic value in the treatment of stress, anxiety, and seizure disorders (Squires, R. F., et al., "[$^{35}$S]t-Butylbicyclophophorothionate binds with high affinity to brain-specific sites coupled to a gamma aminobutyric acid-A and ion recognition site," *Mol. Pharmacol.*, 23:326, 1983; Lawrence, L. J., et al., "Benzodiazepine anticonvulsant action: gamma-aminobutyric acid-dependent modulation of the chloride ionophore," *Biochem. Biophys. Res. Comm.*, 123:1130–1137, 1984; Wood, et al., "In vitro characterization of benzodiazepine receptor agonists, antagonists, inverse agonists and agonist/antagonists," *Pharmacol. Exp. Ther.*, 231:572–576, 1984). We performed an assay to determine the modulation of [$^{35}$S]TBPS as effected by the compounds of the invention and found that these compounds have high potency and efficacy at the GR complex, with stringent structural requirements for such activity.

The procedures for performing this assay are fully discussed in: (1) Gee, et al., 1987 op. cit.; and (2) Gee, K. W., L. J. Lawrence, and H. I. Yamamura, "Modulation of the chloride ionophore by benzodiazepine receptor ligands: influence of gamma-aminobutyric acid and ligand efficacy," *Molecular Pharmacology*, 30, 218, 1986. These procedures were performed as follows:

Brains from male Sprague-Dawley rats were removed immediately following sacrifice and the cerebral cortices dissected over ice. A $P_2$ homogenate was prepared as previously described (Gee, et al., 1986, op. cit.). Briefly, the cortices were gently homogenized in 0.32M sucrose followed by centrifugation at 1000 ×g for 10 minutes. The supernatant was collected and centrifuged at 9000 ×g for 20 minutes. The resultant $P_2$ pellet was suspended as a 10% (original wet weight/volume) suspension in 50 mM Na/K phosphate buffer (pH 7.4) 200 mM NaCl to form the homogenate.

One hundred microliter (µL) aliquots of the $P_2$ homogenate (0.5 milligrams (mg) protein) were incubated with 2 nanomolar (nM) [$^{35}$S]TBPS (70–110 curies/millimole;, New England Nuclear, Boston, Mass.) in the presence or absence of the naturally occurring steroids and their synthetic derivative prodrugs to be tested. The tested compounds were dissolved in dimethylsulfoxide (Baker Chem. Co., Phillipsburg, N.J.) and added to the incubation mixture in 5 µL aliquots. The incubation mixture was brought to a final volume of 1 mL with buffer. Non-specific binding was defined as binding in the presence of 2 µM TBPS. The effect and specificity of GABA (Sigma Chem. Co., St. Louis, Mo.) was evaluated by performing all assays in the presence of GABA plus (+)bicuculline (Sigma Chem. Co.). Incubations maintained at 25° C. for 90 minutes (steady state conditions) were terminated by rapid filtration through glass fiber filters (No. 32, Schleicher and Schuell, Keene, N.H.). Filter bound radioactivity was quantitated by liquid scintillation spectrophotometry. Kinetic data and compound/[$^{35}$S]TBPS dose-response curves were analyzed by nonlinear regression using a computerized iterative procedure to obtain rate constants and $IC_{50}$ (concentration of compound at which half-maximal inhibition of basal [$^{35}$S]TBPS binding occurs) values.

The experimental data obtained for this assay are also published in Gee, et al., 1987 wherein the effect of (+)bicuculline on the pregnane steroid alphaxalone and GABA modulation of 2 nM [$^{35}$S]TBPS binding to rat cerebral cortex is described.

In this experiment, the effect of (+)bicuculline on the ability of alphaxalone or GABA to inhibit the binding of [$^{35}$S]TBPS was determined. Bicuculline is known to be a competitive antagonist of GABA and a classical parallel shift in the dose-response curves is observed. In contrast, the steroid binding site identified by this work is distinct from the GABA/bicuculline site. The shift in dose-response curves induced by bicuculline when the inhibition of [$^{35}$S]TBPS binding is caused by alphaxalone is not parallel. This indicates that the GABA and steroid sites do not overlap.

An assay was performed to determine the effect of pentobarbital on the dissociation kinetics of [$^{35}$S]TBPS in rat cerebral cortical membranes. This assay was performed in accordance with the procedures outlined above. These data indicate that the site of action of the compounds of the invention is unique and distinct from the previously known sites of action for the barbiturates. The effect of pentobarbital, alphaxalone, or 5α-pregnan-3α-hydroxy-20-one (3α-OH-DHP) on the dissociation kinetics for 2 nM [$^{35}$S]TBPS in cortical P2 homogenates was examined. Dissociation of bound [$^{35}$S]TBPS was initiated by 2 µM TBPS in all cases. Pentobarbital at 30 µM induces a biphasic dissociation mechanism which is absent for alphaxalone (300 nM) and 3α-OH-DHP (20 nM).

The kinetic rate constants and half lives obtained by this assay are set forth in Table 1. The information presented in Table 1 shows that the barbiturate induces a shift in the half life of dissociation and the proportion of slow and rapidly dissociating components—hallmark effects of therapeutically useful GABA agonists, barbiturates, and BZs on [$^{35}$S] TBPS binding (Gee, et al., 1986; Maksay, G. & Ticku, M., "Dissociation of [$^{35}$S]t-butylbicyclophosphorothionate binding differentiates convulsant and depressant drugs that modulate GABAergic transmission," *J. Neurochem.*, 44:480–486, 1985). In contrast, the progesterone metabolite 3α-OH-DHP and the pregnane alphaxalone do not influence the proportion of rapid and slow dissociation kinetics of [$^{35}$]TBPS binding. The steroid and barbiturate sites are, therefore, distinct.

TABLE 1

| Conditions | $T_{1/2}$ (min) | | $K_{-1}$ (min$^{-1}$) | | Total percentage of specific sites | |
|---|---|---|---|---|---|---|
| | S | R | S | R | S | R |
| Control | 50 ± 4 | 6 ± 1 | 0.0145 ± 0.0008 | 0.131 ± 0.016 | 73 ± 2 | 30 ± 2 |
| 30 µM Na pentobarbital | 38 ± 3 | 4.4 ± 0.3 | 0.0186 ± 0.0015 | 0.158 ± 0.013 | 61 ± 6* | 48 ± 6** |
| 300 nM alphaxalone | 67 ± 12 | 4.9 ± 1 | 0.0120 ± 0.003 ± | 0.180 ± 0.040 | 73 ± 4 | 34 ± 5 |
| 20 nM 3α-OH-DHP | 76 ± 11 | 6.4 ± 1 | 0.011 ± 0.002 | 0.122 ± 0.030 | 68 ± 3 | 35 ± 3 |

Significantly different from control @ *P < 0.05 and **P < 0.01 by Student's t-test. S and R represent slowly and rapidly dissociating components respectively.

Furthermore, 3α-OH-DHP does not interact with pentobarbital in the enhancement of the binding of [$^3$H]-flunitrazepam ([$^3$H]FLU) to the BZ receptor in the cortical brain homogenates indicating that steroids and barbiturates do not share a common site of action. An assay was performed to determine the effect of a single concentration of pentobarbital (1.0 mM) on 3α-OH-DEP modulation of 0.25 nM [$^3$H]FLU binding to the BZ receptor in rat hippocampal homogenates in accordance with the procedures outlined above. Curves are generated in which the data are expressed as percent enhancements of [$^3$H]FLU binding, which is defined as the percentage of [$^3$H]FLU bound in the absence of 3α-OH-DHP under the control conditions minus 100%. All assays were performed in the absence of GABA.

The data demonstrated that the compounds of and used in the invention interact with a novel site distinct from the barbiturate or BZ regulatory site on the GR complex.

Various compounds were screened to determine their potential as modulators of [$^{35}$S]TBPS binding in vitro. These assays were performed in accordance with the above discussed procedures. Based on these assays, we have established the structure-activity requirements for their specific interaction at the GR complex and their rank order potency and efficacy. Table 2 below provides data pertaining to direct acting compounds tested, while Table 3 provides data on prodrug esters of 3α-OH-DHP.

Columns 1 and 2 of Table 2 show in vitro activity of various direct acting drugs as measured by their ability to modulate the binding of [$^{35}$S]TBPS in the absence and presence of GABA. As can be seen from the table, 3α-OH-DHP has the lowest IC$_{50}$, or concentration necessary to achieve 50% maximal inhibition of [$^{35}$S]TBPS binding, while compounds such as sex steroids and cholesterol are essentially inactive. In vivo data are presented in column 4 as percent of animals protected from convulsions at various time points after administration of metrazol. It can readily be seen by this table that the in vivo data correlate well with the in vitro data. These data also correlate well with data on $^{36}$Cl ion uptake potentiated by various 3α-hydroxy steroids, described in Purdy, R. H., et al., "Synthesis, Metabolism, and Pharmacological Activity of 3α-Hydroxy Steroids Which Potentiate GABA-Receptor-Mediated Chloride Ion Uptake in Rat Cerebral Cortical Synaptoneurosomes," *J. Med. Chem* 33:1572–1581, 1990, incorporated herein by reference.

Table 3 provides in vivo data on prodrug esters of 3α-OH-DHP. The effectiveness of prodrug esters at two different positions on the steroid backbone is measured, as in table 2, by percent of animals protected from convulsions at various time points after administration of metrazol. It is evident from these data that certain prodrugs provide uniform protection over a period of time, while others provide quick protection, and still others provide delayed protection from the effects of the convulsant drug.

TABLE 2

| COMPOUND | STRUCTURE | No GABA[1] IC$_{50}$ (nM) | +5 μM GABA[2] IC$_{50}$ (nM) | Max. Inhib.[3] (%) | Anti-Metrazol[4] ED$_{50}$ (mg/kg) |
|---|---|---|---|---|---|
| 5α-PREGNAN-3α-OL-20-ONE (EPIALLO-PREGNANOLONE) | 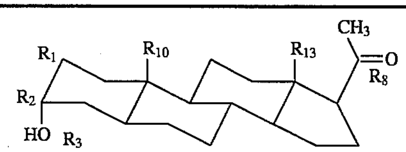 | 230 | 38 | 100 | 5 |
| 3α-HYDROXY-3β-METHYL-5α-PREGNAN-20-ONE | 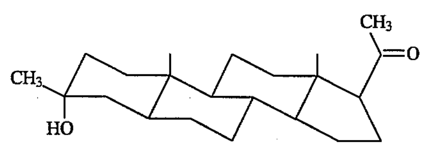 | — | 60 | 100 | 9 |
| 3α,20-DIHYDROXY-20-METHYL-5α-PREGNANE | 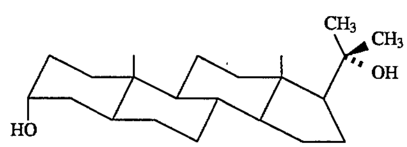 | — | 65 | 45 | — |
| 2β-METHOXY-3α-HYDROXY-5α-PREGNAN-2-ONE | 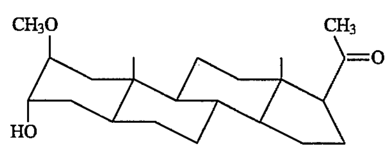 | — | 66 | 100 | 60 |
| 3α-HYDROXY-5α-CIS-PREGN-17(20)-ENE | 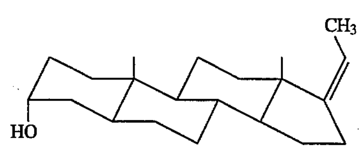 | — | 68 | 100 | — |
| 5α-PREGNAN-3α,21-DIOL-20-ONE TETRAHYDRO-DEOXY-CORTICO-STRONE (THDOC) | 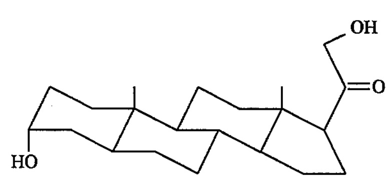 | — | 80 | 100 | 8 |
| 21-CHLORO-5α-PREGNAN-3α-OL-2-ONE | 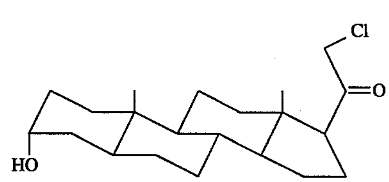 | — | 80 | 100 | — |

TABLE 2-continued

| COMPOUND | STRUCTURE | No GABA[1] IC$_{50}$ (nM) | +5 μM GABA[2] IC$_{50}$ (nM) | Max. Inhib.[3] (%) | Anti-Metrazol[4] ED$_{50}$ (mg/kg) |
|---|---|---|---|---|---|
| 5α-PREGNAN-3α,20α-DIOL (EPIALLO-PREGNANDIOL) | 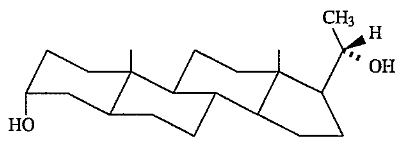 | 359 | 82 | 52 | 40 (iv) |
| 2β-ETHOXY-3α-HYDROXY-5α-PREGNAN-2-ONE | 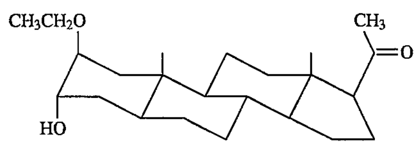 | — | 97 | 100 | 6 |
| 5α-PREGNAN-3α,21-DIOL-20-ONE | 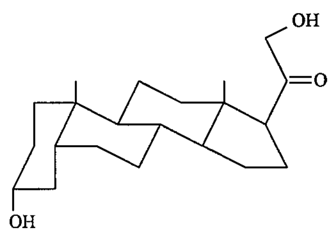 | — | 100 | 100 | 10 |
| 3α-HYDROXY-4-PREGNEN-20-ONE | 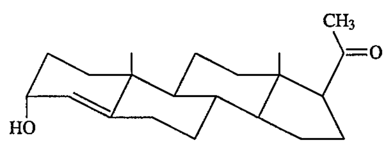 | — | 154 | 80 | 20 |
| 3α-HYDROXY-5α-PREGNEN-16-EN-20-ONE | 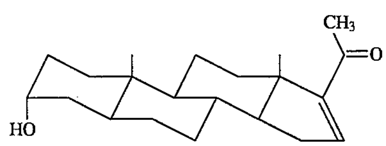 | — | 161 | 100 | — |
| 5α-PREGNAN-3α-OL-11,20-DIONE (ALPHAXALONE) | 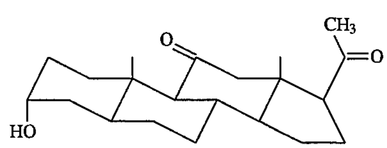 | 11000 | 264 | 100 | — |
| 3α,20-DIHYDROXY-3β,20-DIMETHYL-5α-PREGNANE | 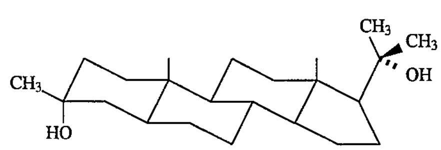 | — | 550 | 50 | — |
| 5α-ANDROSTAN-3α,17β-DIOL | 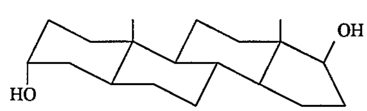 | 15000 | 1000 | 100 | — |
| 5α-PREGNAN-3β,20β-DIOL | 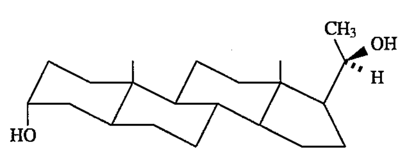 | — | 1000 | 100 | — |

TABLE 2-continued

| COMPOUND | STRUCTURE | No GABA[1] IC$_{50}$ (nM) | +5 μM GABA[2] IC$_{50}$ (nM) | Max. Inhib.[3] (%) | Anti-Metrazol[4] ED$_{50}$ (mg/kg) |
|---|---|---|---|---|---|
| 3α-HYDROXY-5β-PREGN-16-EN-20-ONE | 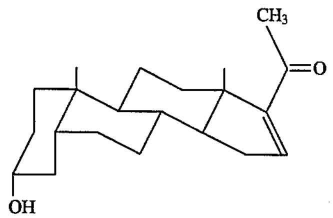 | — | 1000 | 100 | — |
| 3α-HYDROXY-5α-ANDROSTAN-17β-CARBOXYLATE | 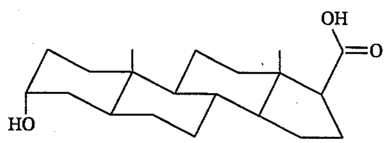 | — | 2680 | 63 | — |
| 3α-HYDROXY-5α-PREGNAN-16α-METHOXY-20-ONE | 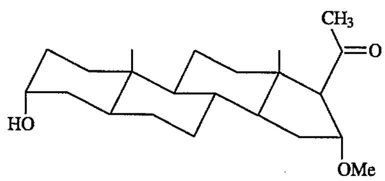 | — | 4500 | 73 | — |
| PROGESTERONE | 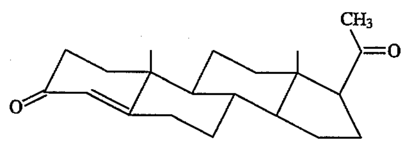 | >10$^5$ | 5200 | 100 | — |
| 5α-PREGNAN-3α,21-DIOL-11,20-DIONE | 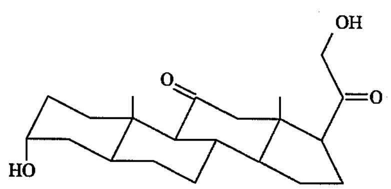 | >10$^5$ | 5500 | 100 | — |
| 3β-HYDROXY-3α-METHYL-5α-PREGNAN-20-ONE | 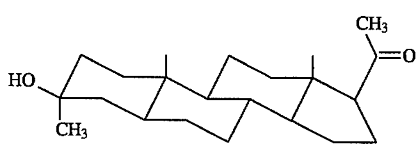 | — | 7400 | 55 | — |
| 5α-ANDROSTAN-17β-OL-3-ONE | 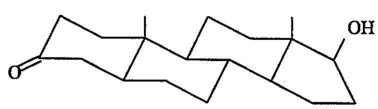 | >10$^5$ | 18000 | 52 | — |
| 2,3-EPOXY-5α-PREGNAN-20-ONE | 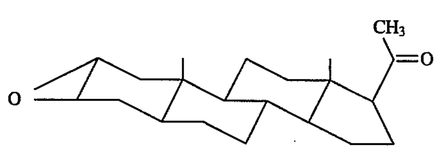 | — | 100000 | — | — |
| 5α-PREGNAN-3β-OL-20-ONE (ALLO-PREGNANOLONE) | 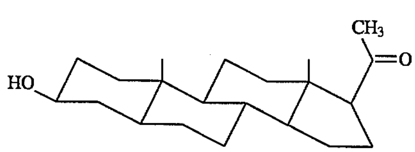 | inactive | >10$^5$ | 33 | — |

TABLE 2-continued

| COMPOUND | STRUCTURE | No GABA[1] IC$_{50}$ (nM) | +5 μM GABA[2] IC$_{50}$ (nM) | Max. Inhib.[3] (%) | Anti-Metrazol[4] ED$_{50}$ (mg/kg) |
|---|---|---|---|---|---|
| 5-PREGNEN-3β-OL-20-ONE (PREGNENOLONE) | 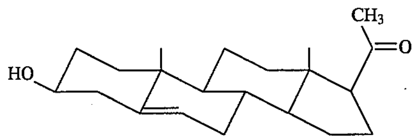 | inactive | >10$^5$ | 30 | — |
| 4-PREGNEN-11b,21-DIOL-3,20-DIONE (CORTICOSTERONE) | 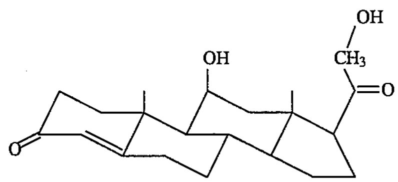 | inactive | >10$^5$ | 21 | — |
| 17β-ESTRADIOL | 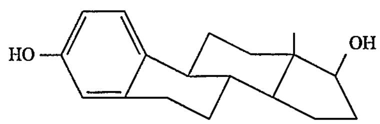 | inactive | inactive | 0 | — |
| CHOLESTEROL | 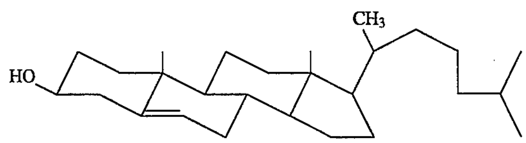 | inactive | inactive | 0 | — |

Legend
[1] Inhibition of [$^{35}$S]-TBPS binding in washed synaptoneurosomes with no GABA added. IC$_{50}$ is the concentration of test compound (nM) required to achieve 50% maximal inhibition.
[2] Inhibition of [$^{35}$S]-TBPS binding in the presence of 5 μM GABA added. IC$_{50}$ is the concentration of test compound (nM) required to achieve 50% maximal inhibition.
[3] Maximal % of specifically bound [$^{35}$S]-TBPS displaced at saturating concentrations of test compound.
[4] Anticonvulsant activity as measured by inhibition of metrazol induced convulsions. ED$_{50}$ is the concentration of test compound (nM) required to achieve 50% maximal inhibition.

TABLE 3

Prodrug esters of 3α-hydroxy-5α-pregnan-20-one

| | | Time Course of Antimetrazol Activity (60 mg/kg) Expressed as % of animals protected after ip injection. | | |
|---|---|---|---|---|
| Prodrug R1 = | Prodrug R2 = | 1 hr | 4 hr | 20 hr. |
| CH$_3$— | H | 25 | — | — |
| CH$_3$–CH$_2$– | H | 75 | 0 | — |
| CH$_3$–CH$_2$–CH$_2$– | H | 75 | 13 | — |
| CH$_3$–(CH$_2$)$_3$– | H | 33 | 33 | 33 |
| (CH$_3$)$_2$CH— | H | 75 | 29 | — |
| (CH$_3$)$_2$CH–CH$_2$–CH$_2$– | H | 0 | 16 | — |
| cyclobutyl | H | 17 | — | 17 |
| phenyl | H | 33 | — | — |

TABLE 3-continued

Prodrug esters of 3α-hydroxy-5α-pregnan-20-one

[Structure: steroid nucleus with R1-C(=O)-O- at 3-position and -C(=O)-CH2-R2 at 20-position]

Time Course of Antimetrazol Activity (60 mg/kg)
Expressed as % of animals protected after ip injection.

| Prodrug R1 = | Prodrug R2 = | 1 hr | 4 hr | 20 hr. |
|---|---|---|---|---|
| Cl—C6H4— | H | 50 | <16 | — |
| CH3O—C6H4— | H | 17 | 17 | — |
| pyridyl (N) | H | — | — | 50 |
| N-CH3 pyridyl | H | 0 | 0 | 63 |
| 3α-OH | —O—C(=O)—CH3 | 50 | 0 | — |
| CH3— | —O—C(=O)—CH3 | 0 | 0 | — |
| (CH3)2CH— | —O—C(=O)—CH3 | 63 | 13 | — |

Partial Agonist Activity

Inasmuch as the desired therapeutic activity should be available to the patient with the fewest undesirable side effects, a notable aspect of this invention involves the discovery of partial agonist activity in those compounds with a 20α-hydroxyl group or the prodrugs of those compounds with a 20α-hydroxyl group. For the patients who desire amelioration of anxiety or convulsions, hypnosis is undesired. The compounds and activities described as partial agonists have the desired effect with minimal undesired effect.

To show the partial agonist effect of the compounds of and used in the invention, the ability of 5α-pregnan-3α,20α-diol (5α-pregnandiol) to alter GABA-stimulated $^{36}$Cl uptake in rat cerebral cortical synaptoneurosomes in the presence or absence of 3α-OH-DHP was studied. In addition, the ability of the BZ clonazepam to modulate $^{36}$Cl uptake in the presence or absence of 5α-pregnandiol was evaluated.

Synaptoneurosomes from cerebral cortex were prepared from male Sprague-Dawley rats as previously described by Suzdak et al. (1986). Briefly, the tissue was homogenized (10% w/v) in 10 mM Tris-HEPES (pH 7.5) buffer, containing in mM: 145 NaCl, 5 KCl, 1 MgCl$_2$, 10 d-glucose, 1 CaCl$_2$ (Sigma Chem. Co., St. Louis, Mo.). The homogenate was diluted to a final volume of 40 mL with buffer and filtered through three layers of Nylon mesh (160 μm). The filtrate was washed twice by centrifugation at 1000 ×g for 15 min and the final pellet was resuspended in ice-cold buffer to yield a protein concentration of 7–10 mg/mL.

Aliquots of membrane preparation (200 μL) were preincubated at 30° C. for 10 min. The interaction was initiated by the simultaneous addition of drugs/steroids and 0.2 mL $^{36}$Cl (New England Nuclear Boston, Mass., 0.55 mCi/mmol, 0.8 μCi/ml) resulting in a total incubation volume of 0.4 mL. Steroids and test drugs were solubilized in dimethylsulfoxide (DMSO) and added to the reaction mixture in 2 μL aliquots. An equal volume of vehicle was always included in the control reaction mixture. The mixture was gently mixed and $^{36}$Cl uptake terminated after 5 sec by the addition of 5 mL of ice cold buffer containing 100 μM picrotoxin (Sigma Chem Co.) followed immediately by rapid filtration through glass fiber filters (Whatman GF/C) under vacuum. The filters were washed twice with 5 mL of ice-cold buffer and the filter-bound radioactivity quantitated by liquid scintillation spectrophotometry. Specific uptake was calculated by subtracting the amount of $^{36}$Cl bound to the filters in the absence of synaptoneurosomes from that observed in their presence. Percent enhancement represents percent increase in uptake over that of basal $^{36}$Cl uptake. Statistical comparisons utilized the analysis of variance (ANOVA).

GABA (25 μM) alone produces a significant enhancement of $^{36}$Cl uptake (Table 4, infra). The specificity of GABA for the GABA$_A$ receptor in the assay is demonstrated by the ability of (+)bicuculline (10 μM) to completely block the stimulatory effect of GABA. The addition of 5α-pregnanediol (Table 4) or 3α-OH-DHP alone to cerebral cortical synaptoneurosomes had no effect on basal $^{36}$Cl uptake. In the presence of GABA, both 5α-pregnanediol and 3α-OH-DHP enhanced $^{36}$Cl uptake in a dose-dependent manner above that produced by GABA (25 μM) alone. The potentiation of GABA-stimulated $^{36}$Cl uptake by 5α-pregnanediol reaches a plateau at a concentration of 3 μM with maximal enhancement of approximately 30% above that produced by GABA alone. Based upon the previous observation that 5α-pregnanediol has limited efficacy relative to 3α-OH-DHP as an allosteric inhibitor of [$^{35}$S]TBPS binding (Gee et al, 1988), we determined the ability of 5α-pregnanediol to modulate GABA-stimulated $^{36}$Cl uptake in the presence of a single concentration (500 nM) of 3α-OH-DHP. 3α-OH-DHP alone produces 60% enhancement of GABA-stimulated $^{36}$Cl uptake, an effect greater than the maximal effect produced by 5α-pregnanediol alone. Under these conditions, partial antagonism of 3α-OH-DHP potentiation of GABA-stimulated $^{36}$Cl uptake would be expected if 5α-pregnanediol is a partial agonist. Accordingly, the capacity of 3α-OH-DHP to potentiate GABA-stimulated $^{36}$Cl uptake was antagonized in a dose-dependent manner by 5α-pregnanediol going from 60 to 31% above that produced by 25 μM GABA alone. In the presence 3 μM 5α-pregnanediol, 3α-OH-DHP (500 nM) enhancement of GABA-stimulated $^{36}$Cl uptake was not significantly different from that produced by 5α-pregnanediol alone. These observations show that 3α-OH-DHP and 5α-pregnanediol act as full and partial agonists respectively at a common steroid site associated with the GR. Since the BZ clonazepam was reported to modulate [$^{35}$S]TBPS binding with limited efficacy similar to that of 5α-pregnanediol, it was of interest to compare the ability of clonazepam and 5α-pregnanediol to modulate GABA-stimulated $^{36}$Cl uptake. As shown in Table 4, the maximal potentiation of GABA-stimulated $^{36}$Cl uptake induced by 5α-pregnanediol and clonazepam, were similar (i.e. 162±4% vs. 164±2%). Yet, 5α-pregnanediol potentiated (i.e. additive) the effect of clonazepam on GABA-stimulated $^{36}$Cl uptake (Table 4). This is indicative of different sites of action for 5α-pregnanediol and clonazepam.

TABLE 4

Effect of steroids, clonazepam and (+)bicuculline on $^{36}$Cl uptake in the presence or absence of GABA (25 μM).

| Condition | % enhancement of basal $^{36}$Cl uptake |
|---|---|
| +GABA | 133 ± 6 |
| +GABA + (+)bicuculline (10 μM) | 3 ± 2 |
| +5α-pregnanediol (3 μM) | 2 ± 1 |
| +Clonazepam (1 μM) | 1 ± 0.5 |
| +GABA + 3α-OH-DHP (500 nM) | 194 ± 8 |
| +GABA + 5α-pregnanediol (3 μM) | 162 ± 4 |
| +GABA + clonazepam (1 μM) | 164 ± 2 |
| +GABA + 5α-pregnanediol (3 μM) + clonazepam (1 μM) | 192 ± 16[a] |

[a]Significantly different from GABA + 5α-pregnanediol (3 μM) at $P < 0.05$ by ANOVA.

Anti-Convulsant Activity

Experiments were also performed to determine the physiological relevance of these interactions by measuring the ability of the compounds of and used in the invention to modulate TBPS-induced convulsions in Swiss-Webster mice. Mice were injected with various doses of the test compounds of the invention 10 minutes prior to the injection of TBPS. The time to onset of myoclonus (presence of forelimb clonic activity) induced by TBPS was determined by observing each mouse for a period of 45 minutes. Significant differences between the time to onset in control mice vs. steroid-treated mice were determined by Student's t-test. The relative rank order potency and efficacy of these steroids in vivo were well correlated with those values determined in vitro. The anti-convulsant and toxicological profiles of 3α-OH-DHP were further determined. In the anti-convulsant screen, mice were injected with various doses of 3α-OH-DHP or vehicle (dimethylsulfoxide) 10 minutes prior to the administration of the following chemical convulsants: metrazol (85 mg/kg); (+)bicuculline (2.7 mg/kg); picrotoxin (3.15 mg/kg); strychnine (1.25 mg/kg); or vehicle (0.9% saline). Immediately after the injection of convulsant or vehicle, the mice were observed for a period of 30 to 45 minutes. The number of animals with tonic and/or clonic convulsions was recorded. In the maximal electroshock test, 50 mA of current at 60 Hz was delivered through corneal electrodes for 200 msec to induce tonic seizure. The ability of 3α-OH-DHP to abolish the tonic component was defined as the endpoint. Sedative potential was determined by a rotorod test 10 minutes after the injection of 3α-OH-DHP where the number of mice staying on a rotating (6 rpm) rod for ≧1 minute in each of 3 trials was determined. The $ED_{50}$ (the dose at which the half-maximal effect occurs) was determined for each screen. The acute $LD_{50}$ (the dose that is lethal to one half of the animals tested) was determined by counting survivors 48 hours after the administration of 3α-OH-DHP. The results are presented in Table 5, infra, and demonstrate that 3α-OH-DHP, in comparison to other clinically useful anti-convulsants, is highly effective with a profile similar to that of the BZ clonazepam. The sedative liability at anticonvulsant doses is low as shown by comparing the $ED_{50}$ values for the rotorod test and (+)bicuculline-induced seizures. The therapeutic index (ratio of $LD_{50}$ to $ED_{50}$) for 3α-OH-DHP is >122 when based on the $ED_{50}$ against (+)bicuculline-induced seizures, thus indicating very low toxicity. These observations demonstrate the therapeutic utility of these compounds as modulators of brain excitability, which is in correspondence with their high affinity interaction with the GR complex in vitro.

TABLE 5

Anticonvulsant and acute toxicological profile of 3α-OH-DHP and those of selected clinically useful anticonvulsants in mice.

| Compound | $ED_{50}$ (mg/Kg) | | | | | | $LD_{50}$ |
|---|---|---|---|---|---|---|---|
| | RR | MES | MTZ | BIC | PICRO | STR | |
| 3α-OH-DHP[a] | 30 | 28.6 | 4.9 | 12.3 | 10.2 | >300 | — |
| 5α-THDOC[a] | 22.9 | 26.7 | 8.1 | 17.8 | 5.6 | >300 | — |
| 3α-OH-DHP[b]* | 40–100 | >300 | 18.8 ± 1.1 | 4.1 ± 1.7 | 31.7 ± 1.1 | >300 | >500 |
| Clonazepam* | 0.184 | 93 | 0.009 | 0.0086 | 0.043 | NP | >6000 |
| Phenobarbital* | 69 | 22 | 13 | 38 | 28 | 95 | 265 |
| Phenytoin* | 65 | 10 | NP | NP | NP | ** | 230 |
| Progabide*** | — | 75 | 30 | 30 | 105 | 75 | 3000 |
| Valproate* | 426 | 272 | 149 | 360 | 387 | 293 | 1105 |

The abbreviations are RR (Rotorod); MES (maximal electroshock); MTZ (metrazol); BIC (bicuculline); PICRO (picrotoxin); STR (strychnine); NP (no protection).
[a]Dissolved in 20% hydroxypropyl-β-cyclodextrin in water. The route of administration for steroids and convulsants was i.p. and s.c., respectively.
[b]Dissolved in DMSO. Data taken from Belelli et al., 1989. $ED_{50}$ values include the 95% confidence limits.
*Anticonvulsant data are from Swinyard & Woodhead, General principles: experimental detection, quantification and evaluation of anticonvulsants, in Antiepileptic Drugs, D. M. Woodbury, J. K. Penry, and C. E. Pippenger, eds., p. 111, (Raven Press, New York), 1982.
**Maximum protection of 50% at 55–100 mg/kg.
***The chemical convulsants in the progabide studies were administered i.v., all data from Worms et al., Gamma-aminobutyric acid (GABA) receptor stimulation. I. Neuropharmacological profiles of progabide (SL 76002) and SL 75102, with emphasis on their anticonvulsant spectra, Journal of Pharmacology and Experimental Therapeutics 220: 660–671, 1982.

Further study of anti-convulsant activity of prodrugs was done over a time course with modifications of the basic compound 3α-OH-DHP. Adult male CF1 mice (20–30g) were used in these studies. Anti-convulsant activities were assessed as previously described by Swinyard and Woodhead (1982) supra. Percent protection against metrazol-induced seizures was plotted against time after administration of the compound. Mice were injected with metrazole (85 mg/kg s.c.) at various times after administration of the compound (3α-OH-DHP at 30 mg/kg, 3α-AC-DHP, 3α-PR-DHP, and 3α-BU-DHP all at 60 mg/kg). Ten to twelve mice were used per dose of test drug. Mice were injected (i.p.) with the compound dissolved in DMSO or 2-hydroxypropyl-β-cyclodextrin, or with vehicle alone (for DMSO, 5 μL/g body weight), at various times prior to the administration (s.c.) of a $CD_{97}$ (dose at which 97% of the animals have seizures from Swinyard and Woodhead, 1982) dose of metrazol (85 mg/kg) or vehicle (0.9% saline, 5 μL/g body weight). Immediately after the injection of the convulsant or vehicle, the mice were observed for a period of 30–45 min. The number of animals with tonic and/or clonic convulsions was recorded. The ability of the steroid to abolish the tonic component was defined as the endpoint. Sedative potential was determined by a rotorod test where the number of mice staying on a rotating (6 rpm) rod for ≧1 min. in each of three trials was determined. The acute $LD_{50}$ was determined by counting survivors 48 h. after the administration (i.p.) of the anti-convulsant compound. All median effective doses were determined by the method of Litchfield and Wilcoxon (1949).

Modification of the basic compound 3α-OH-DHP at the 3α position with an acetate, propionate or butyrate group increased the time of protection provided by the compound. Thus, the compounds of this invention can be modified to provide anti-convulsant activity over a period of time, with varying degrees of protection.

The effects of oral administration of the neuroactive molecules on anti-convulsive activity were also studied by comparing the oral anticonvulsant activity of a neuroactive steroid prodrug and a direct acting molecule. All studies were done using non-fasted CF1 mice (Charles River) during daylight hours (0600–1700). The molecules were administered orally in a vehicle containing 0.35% hydroxypropyl cellulose and 4% Tween 80 in 0.9% NaCl (micronizing solution). The molecules were placed in a glass mill jar with glass beads and micronized for 48 hrs prior to administration. This procedure results in drug particles approximately 7–35 μmeters in size as determined by video microscopy. The anticonvulsant steroids, 3α-isobutyryloxy-5α-pregnan-20-one (100 mg/kg) and 3α-hydroxy-3β-methyl-5α-pregnan-20-one (10 mg/kg) were given by oral feeding tube. The chemical convulsant metrazol (85 mg/kg; subcutaneous) was administered at various times following the anticonvulsant steroid. Results are expressed as the percentage of animals which did not show signs of myoclonus (i.e., percent protected) within 30 min of administration of convulsant agent.

There is extensive anti-convulsant activity over a useful period of time when either a prodrug or a direct acting anti-convulsant neuroactive steroid is administered orally. This is an important feature when such drugs are to be used therapeutically.

Benefits over Progesterone

The correlations between reduced levels of progesterone and the symptoms associated with PMS, PND, and catamenial epilepsy (Backstrom, et al., 1983, op. cit.; Dalton, K., 1984, op. cit.) led to the use of progesterone in their treatment (Mattson, et al., 1984; and Dalton, 1984). However, progesterone is not consistently effective in the treatment of the aforementioned syndromes. For example, no dose-response relationship exists for progesterone in the treatment of PMS (Maddocks, et al, 1987, op. cit.). These results are predictable when considered in light of the results of our in vitro studies which demonstrate that progesterone has very low potency at the GR complex, as seen in Table 2, compared to certain metabolites of progesterone.

The beneficial effect of progesterone is probably related to the variable conversion of progesterone to the active progesterone metabolites. The use of specific progesterone metabolites in the treatment of the aforementioned syndromes is clearly superior to the use of progesterone based upon the high potency and efficacy of the metabolites and their derivatives (See Gee, et al., 1987, and Table 2 above).

No Hormonal Side Effects

It has also been demonstrated that the compounds of and used in the invention lack hormonal side effects by the lack of affinity of these compounds of the invention for the progesterone receptor. The data were obtained by performing assays in accordance with the procedures outlined above to determine the effect of progesterone metabolites and the progestin R5020 on the binding of [$^3$H]R5020 to the progesterone receptor in rat uterus. The following compounds were tested: 5α-pregnan-3α-ol-20-one (DHP), 5α-pregnan-3α,21-diol-20-one (TM-DOC), and 5β-pregnan-3α,20α-diol (5BETA).

The hormonal activity of drugs described herein was further studied through testing their potential estrogenic, progestinic, mineralocorticoid and glucocorticoid activities. These activities were analyzed by monitoring the ability of the drugs to inhibit binding of the steroid hormones to their respective hormone receptors. The results are shown in Tables 6–9. They are expressed as percent inhibition of $^3$H-ligand binding to the various steroid hormone receptors for the drugs at $10^{-6}$ and $10^{-5}$M. Control values are represented by the binding in the absence of drugs.

In Table 6, rats were adrenalectomized 3 days prior to sacrifice. To isolate the mineralocorticoid receptor, brain cytosol fractions were prepared as previously described. The drugs were incubated with 3 nM of $^3$H-aldosterone (the specific ligand for the mineralocorticoid receptor) in the presence of the selective type II agonist RU28362 (0.5 μM) which blocks $^3$H-aldosterone binding to the type II (glucocorticoid) receptors. The specific binding was 1756 cpm/fraction.

TABLE 6

INHIBITION OF $^3$H-ALDOSTERONE
BINDING TO HIPPOCAMPAL
CYTOSOL MINERALOCORTICOID RECEPTORS.

| COMPETITOR ($10^{-6}$ M) | % of INHIBITION |
|---|---|
| Aldosterone | 95.5 |
| 5α-pregnan-3α,21-diol-20-one | 76.7 |
| 5β-pregnan-3α,21-diol-20-one | 13.8 |
| 5α-pregnan-3α,ol-20-one | 0 |
| 5β-pregnan-3α,ol-20-one | 0 |
| 5α-pregnan-3α,20α-diol | 0 |
| 5β-pregnan-3α,20α-diol | 0 |
| 5α-pregnan-3α,20-diol-20-dimethyl | 0 |
| 5α-pregnan-3α-ol-3β-methyl-20-one | 3.2 |
| 5α-pregnan-3β,20-trimethyl-3α,20-diol | 0 |

For Table 7, brain cytosol fractions were prepared as for Table 6, and the drugs were incubated with 3 nM of $^3$H-dexamethasone (the specific ligand for the glucocorticoid receptor). The specific binding was 1174 cpm/fraction.

TABLE 7

INHIBITION OF $^3$H-DEXAMETHASONE BINDING TO GLUCOCORTICOID RECEPTORS.

| COMPETITOR ($10^{-6}$ M) | % of INHIBITION |
|---|---|
| Dexamethasone | 100 |
| 5α-pregnan-3α,21-diol-20-one | 29.5 |
| 5β-pregnan-3α,21-diol-20-one | 8.2 |
| 5α-pregnan-3α,ol-20-one | 8.7 |
| 5β-pregnan-3α,ol-20-one | 5.9 |
| 5α-pregnan-3α,20α-diol | 2.6 |
| 5β-pregnan-3α,20α-diol | 1.4 |
| 5α-pregnan-20-dimethyl-3α,20-diol | 2.6 |
| 5α-pregnan-3α-ol-3β-methyl-20-one | 0.6 |

Table 8 shows the inhibition of $^3$H-estradiol (the specific ligand for the estrogen receptor) binding to bovine uteri cytosol, prepared as previously described. Two concentrations of $^3$H-estradiol; (A) 0.15 nM and (B) 0.25 nM, were incubated with the cytosol in the presence of the drugs. The specific binding for $^3$H-estradiol at 0.15 nM and 0.25 nM was 1241 cpm/fraction and 1951 cpm/fraction, respectively.

TABLE 8

INHIBITION OF $^3$H-ESTRADIOL BINDING TO THE BOVINE UTERAL ESTROGEN RECEPTORS.

| | % of INHIBITION | | | |
|---|---|---|---|---|
| | COMPETITOR AT $10^{-6}$ M | | COMPETITOR AT $10^{-5}$ M | |
| COMPETITOR | A[a] | B[b] | A | B |
| 5α-pregnan-3α,ol-20-one | 0 | 0 | 0 | 3 |
| 5α-pregnan-3α,21-diol-20-one | 2 | 4 | 23 | 23 |
| 5α-pregnan-3α,20α-diol | 0 | 0 | 7 | 13 |
| 5α-pregnan-3α-ol-3β-methyl-20-one | 0 | 0 | 2 | 6 |
| 5β-pregnan-3α,21-diol-20-one | 0 | 4 | 3 | 7 |
| 5α-pregnan-3β,20-trimethyl-3α,20-diol | 0 | 4 | 3 | 7 |
| 5β-pregnan-3α,20α-diol | 8 | 0 | 0 | 0 |
| 5β-pregnan-3α,ol-20-one | 0 | 0 | 5 | 0 |
| 5α-pregnan-20-dimethyl-3α,20-diol | 0 | 0 | 5 | 5 |

For the data presented in Table 9, bovine uteri cytosol was isolated as they were for Table 7 and used for following binding to progesterone receptors by following the inhibition of $^3$H-progesterone, the natural ligand. Two $^3$H-progesterone concentrations, (A) 0.15 nM and (B) 0.25 nM were incubated with the cytosol in the presence of the drugs. The specific binding for $^3$H-progesterone at 0.15 nM and 0.25 nM was 2893 cpm/fraction and 4222 cpm/fraction, respectively.

TABLE 9

INHIBITION OF $^3$H-PROGESTERONE BINDING TO THE BOVINE UTERAL PROGESTERONE RECEPTORS.

| | % of INHIBITION | | | |
|---|---|---|---|---|
| | COMPETITOR AT $10^{-6}$ M | | COMPETITOR AT $10^{-5}$ M | |
| COMPETITOR | A[a] | B[b] | A | B |
| 5α-pregnan-3α,ol-20-one | 14 | 2 | 41 | 40 |
| 5α-pregnan-3α,21-diol-20-one | 13 | 5 | 35 | 28 |
| 5α-pregnan-3α,20α-diol | 6 | 1 | 2 | 3 |
| 5α-pregnan-3α-ol-3β-methyl-20-one | 4 | 2 | 10 | 5 |
| 5β-pregnan-3α,21-diol-20-one | 6 | 2 | 19 | 10 |
| 5α-pregnan-3β,20-trimethyl-3α,20-diol | 8 | 0 | 5 | 0 |
| 5β-pregnan-3α,20α-diol | 0 | 0 | 1 | 1 |
| 5β-pregnan-3α,ol-20-one | 9 | 1 | 17 | 13 |
| 5α-pregnan-20-dimethyl-3α,20-diol | 0 | 0 | 0 | 0 |

The results of these experiments clearly show that the neuroactive steroids do not have a strong affinity for any of the above steroid receptors. Thus, they will not have predicted hormonal side-effects which would result from such steroid receptor binding.

Anxiolytic Effects

The following experiments demonstrate that the progesterone metabolite, 3α-OH-DHP, is an effective anxiolytic in three animal models of human anxiety that measure the behavioral effects of anxiolytic compounds. In addition, they show that the anxiolytic effects of 3α-OH-DHP were mediated through a mechanism that is separate from the that of the BZs.

The light/dark transition test (Crawley and Goodwin, 1980) is based on the observation that rodents naturally tend to explore novel environments, but open, brightly lit arenas are aversive to the rodents and inhibit exploratory behavior (Christmas and Maxwell, 1970; File, 1980). A variety of clinically established anxiolytics including diazepam, clonazepam and pentobarbital have been shown to increase the number of transitions between the light box and the dark box, whereas nonanxiolytic drugs do not demonstrate this behavioral effect (Blumstein and Crawley, 1983; Crawley, 1981; Crawley and Davis, 1982; Crawley and Goodwin, 1980; Crawley et al., 1984). Similar to the light/dark transition test, the open-field test measures the antagonism between the tendency to explore a novel environment and the tendency to remain still in an aversire environment (brightly lit arena). BZs have been shown to increase ambulation in open-field arenas (Davies and Steinberg, 1984; Hughes and Greig, 1975; Sansone, 1979; Bruhwyler et al., 1990; Bruhwyler, 1990). The open-field test provides a simple, non-punished assessment of the potential anxiolytic properties of novel compounds. Finally, 3α-OH-DHP was tested for anxiolytic properties in a Vogel conflict paradigm. The ability of BZs to attenuate the suppression of behavior by punishment in conflict paradigms is well established (Gellar et al., 1962; Vogel et al., 1971). The Vogel test provides classical behavioral pharmacological support to the two "exploratory" models of anxiety in testing the anxiolytic effects of 3α-OH-DHP and 5α-THDOC. In addition, CGS-8216, a BZ antagonist, has been shown to block diazepam's anxiolytic effects in the light/dark transition test (Crawley et al., 1984). To further demonstrate, in vitro, the uniqueness of the steroid site, we attempted to block the anxiolytic effect of 3α-OH-DHP with CGS-8216 in the light/dark transition test.

Male N.I.H. Swiss-Webster mice (Harlan) weighing 15–20 g were used in all experiments. The mice were housed 4/cage in polyethylene cages with sawdust bedding. The colony room was environmentally controlled (22° C.) with a 12 hr. light/dark cycle (0600–1800 hrs.). The mice had free access to food and water. The experiments were run from 0700–1500 hrs. and groups were counterbalanced for time of day effects.

a) Light/Dark Transitions

The method used was previously described by Crawley and Goodwin (1980). The apparatus included a large box (26×33×24 cm) connected to a small box (15×22×14 cm) through an opening (5×6 cm). The large box was brightly lit with a standard 100 W light bulb, while the small box was kept dark. Following pretreatment with a test drug, mice were placed in the center of the large box and the number of transitions between the large and small boxes was counted for 10 min. Drug pretreatment times were as follows: diazepam (30 min.); 3α-OH-DHP (10 min.); and 5α-THDOC (10 min.). During the antagonist studies, CGS-8216 was administered 30 min. prior to the test drug.

b) Open-Field Activity

As a secondary measure of anxiolytic effects, naive mice were placed in the center of a large, brightly lit plexiglass box (42×42×30.5 cm) and the total distance traveled was measured during a 10 min. test period. Anxiolytics have been shown to increase the amount of "exploring" or locomotor activity in a novel environment (Treit, 1985; Lister, 1990). The Digiscan Activity Monitor (Omnitech Electronics, Columbus, Ohio) includes 16 photobeams that surround the box. The activity monitor is linked to a computer through a Digiscan Analyzer (Omnitech Electronics) and the data is analyzed using the Integrated Lab Animal Monitoring System (Omnitech Electronics). The mice were administered drugs as described for light/dark transitions.

For evaluation of a drug's effects on general activity, mice were first habituated to the open-field apparatus for 15 min. The following day, mice were pretreated with a test drug and placed in the center of the activity chambers. The total distance traveled was measured for 10 min.

c) Vogel Paradigm

An Anxio-Monitor (Omnitech Electronics, Columbus, Ohio) was used for measuring lick suppression. The testing chamber consisted of a clear plexiglass box (29 cm×29 cm×23 cm) with a metal drinking tube located 2.5 cm from the floor and extending 2 cm into the box. The shock was applied through the drinking spout and was controlled by the Anxio-Monitor. The number of licks was counted and displayed by the Anxio-Monitor. The reinforcer was 0.1M sucrose.

The conflict test procedure described by Vogel et al. (1980) was employed. This procedure is a modification of the original lick suppression test first described by Vogel et al. (1971). After 24 hr. of water deprivation, mice were allowed to explore the test apparatus and drink without punishment for 10 min. or 100 licks. The following day (48 hr. after the start of water deprivation), mice were pretreated with 3α-OH-DHP (20 mg/kg), chlordiazepoxide (CDP; 10 mg/kg) or vehicle and subsequently placed in the conflict apparatus. Mice were allowed unpunished access to the drinking tube for 20 licks, thereafter, every 10th lick was punished with 0.1 mA shock. The test duration was 5 min.

The steroids 3α-OH-DHP, 3β-OH-DHP, and 5α-THDOC were synthesized as described above. 2-Hydroxypropyl β-cyclodextrin (β-cyclodextrin) is available from Aldrich (Milwaukee, Wis.). Diazepam and chlordiazepoxide are available from Sigma, Co. (St. Louis, Mo.). CGS-8216 was obtained from Ciba-Geigy (Summit, N.J.). All drugs were dissolved in 20% β-cyclodextrin in water and sonicated overnight. All drugs were administered intraperitoneally in a volume of 100 μL/20 g. CGS-8216 was administered subcutaneously in a volume of 100 μL/20 g.

Dose-response curves for 3α-OH-DHP, 5α-THDOC and diazepam generated in the light/dark transition test were run over several days. The vehicle control data were analyzed across test days using an 1-way analysis of variance (ANOVA). Because the vehicle data were not significantly different across days, the control data were collapsed for each test drug. The dose-response curves were then analyzed using a 1-way ANOVA, followed by Dunnett's t-test for individual comparisons between doses and control. The open-field and habituated locomotor data were analyzed using ANOVA followed by Dunnett's t-test. 3α-OH-DHP and CDP were tested on separate days in the lick-suppression test. The control groups were significantly different, therefore the data was analyzed using a Student's t-test (2-tailed) and for comparison is graphically displayed as percent of corresponding control. All data are expressed as the mean ±S.E.M.

The steroid 3α-OH-DHP produced anxiolytic effects as seen by an increase in the number of transitions in the light/dark paradigm. 3α-OH-DHP produced a significant dose-dependent response $(F(4,63)=21.5; p=0.0001)$. The number of transitions was increased by 3α-OH-DHP significantly $(p<0.01)$ at 10, 20, and 40 mg/kg. 3α-OH-DHP reached maximal effect at a dose of 20 mg/kg with an average of 70.2±4.3 transitions in a 10 min. period. The highest dose tested, 40 mg/kg, started a trend towards a reduction in the number of transitions. Several compounds have been shown to produce an inverted U-shaped dose-response curve in the light/dark transition paradigm (Crawley et al., 1986).

The deoxycorticosteroid metabolite, 5α-THDOC, produced a significant $(F(4,54)=10.0; p=0.0001)$ dose-related effect in the light/dark transition test. 5α-THDOC, at a dose of 20 mg/kg was significantly different from vehicle $(p<0.01)$. Although 5α-THDOC did produce a greater number of transitions at 10 mg/kg compared with vehicle (49.4±2.0 vs. 35.2±2.0), the difference did not reach significance $(p<0.06)$. At the highest dose tested, 5α-THDOC (40 mg/kg), produced a significant decrease $(p<0.05)$ in the number of transitions as compared with vehicle control.

Diazepam's effects on light/dark transitions were determined. Diazepam produced a significant $(F(5,72)=31.6; p=0.0001)$ inverted U-shaped dose-response curve. Diazepam was significantly $(p<0.01)$ different from controls at 1.0, 5.0, 10, and 20 mg/kg. Diazepam's maximal response was at 10 mg/kg with 86.4±5.4 transitions. Though significant at 20 mg/kg, diazepam's effects were diminished as compared with the effects at 10 mg/kg. These results are similar to the inverted U-shaped curves seen with the two steroids, 3α-OH-DHP and 5α-THDOC.

The diastereomer of 3α-OH-DHP, 3β-OH-DHP (20 mg/kg), did not produce an anxiolytic effect in the light/dark transition paradigm. In the same experiment, 3α-OH-DHP (20 mg/kg) did produce a significant (p<0.01) increase in the number of light/dark transitions over those produced by the carrier alone (β-cyclodextrin). These results demonstrate the stereo-specificity of the anxiolytic effects of the steroid 3α-OH-DHP.

The specific BZ antagonist CGS-8216 (10 mg/kg) was unable to block the anxiolytic effect of 3α-OH-DHP. 3α-OH-DHP (10 mg/kg) produced significant (p<0.01) increases alone and in the presence of CGS-8216. However, CGS-8216 was able to block the anxiolytic effect of diazepam. Diazepam (1.0 mg/kg) alone produced a significant (p<0.01) increase in transitions as compared to control. CGS-8216 did not demonstrate any intrinsic activity and was not significantly different from vehicle control (p>0.4). These results demonstrate that the anxiolytic effects of the steroid 3α-OH-DHP are through a separate neural mechanism from that of the BZs.

When placed in a novel, brightly lit open-field, mice demonstrate a low level of activity (i.e., exploration, locomotion, etc.), whereas anxiolytics increase the amount of activity in a novel environment (Lister, 1990). As shown in Table 10, there was a significant drug effect on open-field activity (F(4,44)=18.05; p=0.0001). Specifically, the steroids 3α-OH-DHP and 5α-THDOC produced significant (p<0.01) increases in activity as compared with control. In addition, diazepam produced a significant (p<0.01) increase in activity as compared with β-cyclodextrin vehicle control. However, 3β-OH-DHP did not show any effect in the open-field test.

TABLE 10

Effects of Steroids on Open-Field Activity

| DRUG | DOSE (mg/kg) | TOTAL DISTANCE (cm) |
|---|---|---|
| β-Cyclodextrin | | 2004.6 ± 134.6 |
| 3β-OHDHP | 20 | 1979.8 ± 174.5 |
| 3α-OHDHP | 20 | 5344.9 ± 754.5** |
| 5α-THDOC | 20 | 7328.4 ± 769.5** |
| DIAZEPAM | 10 | 4817.7 ± 528.4** |

Mice were pretreated 10 min or 30 min (diazepam) prior to being placed in the center of the open-field apparatus. Total distance travelled was measured for 10 min (see Methods for details). Each group consisted of 9–10 mice.
**p < .01: significantly different from the β-cyclodextrin vehicle control according to Dunnett's t-test.

3α-OH-DHP produced a significant increase in locomotor activity (p<0.01) in mice that were acclimated to the test chambers. 3α-OH-DHP (20 mg/kg) treated mice traveled a total distance of 5694.7±608.4 cm compared with controls 2061.2 ±157.7 cm. Diazepam (10 mg/kg) had no effect on locomotor activity (2258.0±897.7 cm).

Administration of 3α-OH-DHP (20 mg/kg) disinhibited punished-induced suppression of drinking. 3α-OH-DHP produced a significant 235.6% increase in the number of shocks received during the 5 min. test session as compared with controls (13.9±2.1 vs. 5.9±0.54; t=–3.98; p=0.01). In comparison, CDP (10 mg/kg) produced a 197.4% increase in punished responding as compared with controls (6.14±1.14 vs. 3.11±0.68; t=–2.4; p=0.03).

While the preferred embodiments have been described and illustrated, various substitutions and modifications may be made thereto without departing from the scope of the invention. Accordingly, it is to be understood that the present invention has been described by way of illustration and not limitation.

We claim:
1. A method for modulating excitability of the central nervous system as mediated by the ability to regulate chloride ion channels associated with the GABA-benzodiazepine receptor complex comprising administering to an animal subject an amount, effective to modulate said central nervous system excitability, of a neuroactive steroid compound that activates the GABA-benzodiazepine receptor complex by attaching to a brain receptor site, of formula I:

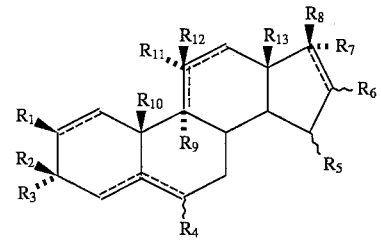

wherein
A) R1, R4, R5, and R6 are individually selected from the group consisting of:
   (1) hydrogen, hydroxyl, or thiol;
   (2) pharmaceutically acceptable ether and thioether groups —Y—R14, wherein R14 is a $C_1$ halogenated or unhalogenated radical, a $C_2$-$C_{10}$ saturated or unsaturated, halogenated or unhalogenated straight chain radical, a $C_3$-$C_{10}$ saturated or unsaturated, halogenated or unhalogenated branched chain radial, a $C_3$-$C_{10}$ cyclic aliphatic radical, a $C_6$-$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
   (3) halogen atoms; and
   (4) a $C_1$ halogenated or unhalogenated radical, $C_2$-$C_8$ saturated or unsaturated, halogenated or unhalogenated straight chain radicals, $C_3$-$C_8$ saturated or unsaturated, halogenated or unhalogenated branched chain radicals, or $C_3$-$C_8$ cyclic aliphatic radicals;
B) R2 is selected from the group consisting of
   (1) hydrogen; and
   (2) a $C_1$ halogenated or unhalogenated radical, $C_2$-$C_4$ saturated or unsaturated, halogenated or unhalogenated straight chain radicals, or $C_3$-$C_4$ saturated or unsaturated, halogenated or unhalogenated branched chain radicals;
C) R3 is selected from the group consisting of:
   (1) hydroxyl or thiol;
   (2) pharmaceutically acceptable ester and thioester groups

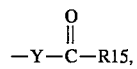

wherein R15 is hydrogen or a $C_1$ halogenated or unhalogenated radical, a $C_2$-$C_{20}$ saturated or unsaturated, halogenated or unhalogenated straight chain radical, a $C_3$-$C_{20}$ saturated or unsaturated, halogenated or unhalogenated branched chain radical, a $C_3$-$C_{10}$ cyclic aliphatic radical, a $C_6$-$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
(3) pharmaceutically acceptable cleavable esters of natural or synthetic amino acids;
(4) pharmaceutically acceptable acyloxyalkyloxy or acyloxyalkylthio

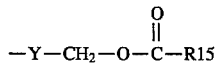

radicals, wherein Y is R15 are as previously defined; and
(5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucoronic, and 1-methyl-1,4-dihydro nicotinic;

D) R7 is selected from the group consisting of
(1) hydrogen or hydroxyl; and
(2) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
except when R8 is hydroxyl, R7 is not hydroxyl, and when the bond between carbons C16–C17 in formula I is a double bond, R7 is not present;

E) R8 is selected from the group consisting of:
(1) hydroxyl, thiol, 2-hydroxyethanoyl

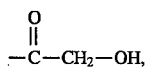

or 1-hydroxyethyl

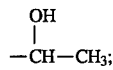

(2) pharmaceutically acceptable ester or thioester groups

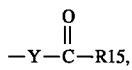

wherein Y and R15 are as previously defined;
(3) pharmaceutically acceptable

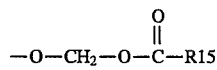

groups wherein R15 is as previously defined;
(4) pharmaceutically acceptable

groups, wherein R15 is as previously defined;

(5) pharmaceutically acceptable

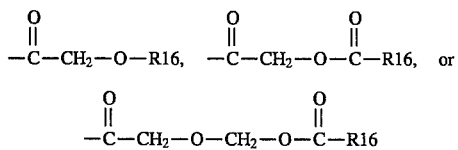

groups, wherein R16 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms, or an amide

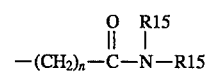

radical where n is 1–10, R15 is as previously defined, and each R15 is independently determined;

(6) pharmaceutically acceptable oxime

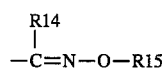

groups, where R14 and R15 are as previously defined;
(7) pharmaceutically acceptable thiazolidine derivatives having the formula:

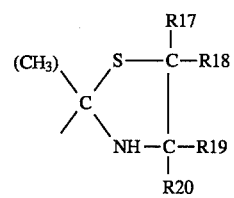

wherein any two or R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

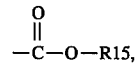

wherein R15 is as previously defined;

(8) pharmaceutically acceptable

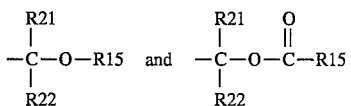

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogeneated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined;

(9) pharmaceutically acceptable carboxylate

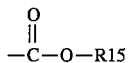

groups wherein R15 is as previously defined;

(10) pharmaceutically acceptable

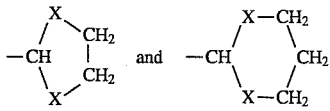

groups wherein each X independently is oxygen, nitrogen, or sulfur;

(11) cyano —C≡N; and

(12) pharmaceutically acceptable esters of thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

or R7 and R8 combined are =CH—$CH_3$;

F) R9 is selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl, except if the bond between carbons C9–C11 in formula I is a double bond, then R9 is not present;

G) R10 and R13 are individually selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
(1) hydrogen, hydroxyl, or thiol;
(2) $C_1$–$C_{10}$ alkyloxy and alkylthio radicals, $C_6$–$C_{10}$ aryloxy and arylthio radicals, or amino radicals;
(3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and (4) pharmaceutically acceptable

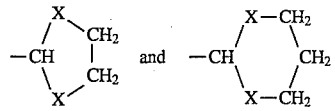

groups wherein each X independently is as previously defined;

or together R11 and R12 make a double bond to oxygen or sulfur to form the ketone or thioketone; except if the bond between carbons C9–C11 or C11–C12 in formula I is a double bond, then R12 is not present.

2. The method of claim 1 where any said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, ε-caprolactone, ε-caprolactam, omega-thiocaprolactam and morpholine.

3. The method of claim 1 where R3 is a pharmaceutically acceptable ester of an acid selected from the group consisting of acetic, propionic, normal and isomeric forms of butyric, valeric, hexanoic, heptanoic, octanoic, nonanoic, decanoic, undecanoic and dodecanoic, cinnamic, benzylic, benzoic, maleic, fumaric, ascorbic, pimelic, succinic, bismethylene-salicylic, methanesulfonic, ethanesulfonic, oxalic, tartaric, salicylic, acetyl salicylic, citric, gluconic, aspartic, stearic, palmitic, itaconic, glycolic, p-aminobenzoic, glutamic, benzenesulfonic, cyclohexyl-sulfamic, gamma-amino-butyric, α-(2-hydroxyethylamino)-propionic, phosphoric, phosphonic, sulfuric, sulfonic, glucuronic and 1-methyl-1,4-dihydro nicotinic.

4. The method of claim 1 wherein the modulation of excitability of the central nervous system is effected by said neuroactive steroid compound by regulation of the chloride ion channels associated with the GABA receptor complex.

5. The method of claim 1 wherein the modulation of excitability of the central nervous system is effected by said neuroactive steroid compound by activating the GABA receptor-chloride ionophore complex (GRC) by attaching to a specific brain steroid receptor site associated with and activating said complex.

6. The method of claim 4 wherein the regulation of the chloride ion channels associated with the GABA receptor complex is effected by said neuroactive steroid compound by activating the GRC by attaching to a specific brain steroid receptor site associated with and activating said complex.

7. The method of claim 1 wherein said neuroactive steroid compound is administered in an amount sufficient to alleviate stress or anxiety in said animal.

8. The method of claim 1 wherein said neuroactive steroid compound is administered in an amount sufficient to alleviate seizure activity in said animal.

9. The method of claim 1 wherein said neuroactive steroid compound is administered in an amount sufficient to reduce or alleviate insomnia in said patient.

10. The method of claim 1 wherein said neuroactive steroid compound is administered in an amount sufficient to reduce or alleviate symptoms of PMS or PND in said patient.

11. The method of claim 1 wherein said neuroactive steroid compound is administered in an amount sufficient to treat mood disorders in said patient.

12. The method of claim 11 wherein said mood disorder is depression.

13. The method of claim 1 wherein said pharmaceutically effective amount is from about 5 mg to about 500 mg per dosage unit.

14. The method of claim 1 wherein R8 is selected from

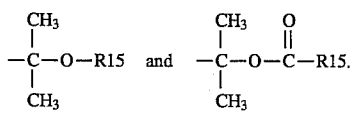

15. The method of claim 14 where any said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan hexamethyleneimine, ε-caprolactone, ε-caprolactam, omega-thiocaprolactam and morpholine.

16. The method of claim 14 where R3 is a pharmaceutically acceptable ester of an acid selected from the group consisting of acetic, propionic, normal and isomeric forms of butyric, valeric, hexanoic, heptanoic, octanoic, nonanoic, decanoic, undecanoic and dodecanoic, cinnamic, benzylic, benzoic, maleic, fumaric, ascorbic, pimelic, succinic, bismethylenesalicylic, methanesulfonic, ethanesulfonic, oxalic, tartaric, salicylic, acetyl salicylic, citric, gluconic, aspattic, stearic, palmitic, itaconic, glycolic, p-aminobenzoic, glutamic, benzenesulfonic, cyclohexyl-sulfamic, gamma-amino-butyric, α-(2-hydroxyethylamino)-propionic, phosphoric, phosphonic, sulfuric, sulfonic, glucuronic and 1-methyl-1,4-dihydro nicotinic.

17. The method of claim 14 wherein the modulation of excitability of the central nervous system is effected by said neuroactive steroid compound by regulation of the chloride ion channels associated with the GABA receptor complex.

18. The method of claim 14 wherein the modulation of excitability of the central nervous system is effected by said neuroactive steroid compound by activating the GABA receptor-chloride ionophore complex (GRC) by attaching to a specific brain steroid receptor site associated with and activating said complex.

19. The method of claim 17 wherein the regulation of the chloride ion channels associated with the GABA receptor complex is effected by said neuroactive steroid compound by activating the GRC by attaching to a specific brain steroid receptor site associated with and activating said complex.

20. The method of claim 14 wherein said neuroactive steroid compound is administered in an amount sufficient to alleviate stress or anxiety in said animal.

21. The method of claim 14 wherein said neuroactive steroid compound is administered in an amount sufficient to alleviate seizure activity in said animal.

22. The method of claim 14 wherein said neuroactive steroid compound is administered in an amount sufficient to reduce or alleviate insomnia in said patient.

23. The method of claim 14 wherein said neuroactive steroid compound is administered in an amount sufficient to reduce or alleviate symptoms of PMS or PND in said patient.

24. The method of claim 14 wherein said neuroactive steroid compound is administered in an amount sufficient to treat mood disorders in said patient.

25. The method of claim 24 wherein said mood disorder is depression.

26. The method of claim 14 wherein said pharmaceutically effective amount is from about 5 mg to about 500 mg per dosage unit.

27. The method of claim 1 wherein R8 is a pharmaceutically acceptable thiazolidine derivatives having the formula:

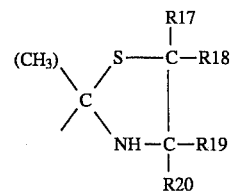

wherein any two of R17, R18, R19 and R20 are individually hydrogen or a $C_1$ halogenated or unhalogenated radical, a $C_2$–$C_{10}$ saturated or unsaturated, halogenated or unhalogenated straight chain radical, or a $C_3$–$C_{10}$ saturated or unsaturated, halogenated or unhalogenated branched chain radical, or $C_3$–$C_8$ cyclic aliphatic radical, or $C_6$–$C_8$ aromatic radical, or a 4, 5, or 6 membered C- or N- attached heterocyclic radical containing 1, 2, or 3 heteroatoms selected from the group consisting of O, N, and S, excluding heterocyclic radicals with two or more adjacent O or S atoms, and the remaining two of R17, R18, R19 and R20 are individually hydrogen; or one or more of R17, R18, R19, and R20 are individually

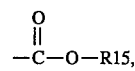

wherein R15 is as previously defined.

28. The method of claim 27 where any said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan hexamethyleneimine, ε-caprolactone, ε-caprolactam, omega-thiocaprolactam and morpholine.

29. The method of claim 27 where R3 is a pharmaceutically acceptable ester of an acid selected from the group consisting of acetic, propionic, normal and isomeric forms of butyric, valeric, hexanoic, heptanoic, octanoic, nonanoic, decanoic, undecanoic and dodecanoic, cinnamic, benzylic, benzoic, maleic, fumaric, ascorbic, pimelic, succinic, bismethylenesalicylic, methanesulfonic, ethanesulfonic, oxalic, tartaric, salicylic, acetyl salicylic, citric, gluconic, aspartic, stearic, palmitic, itaconic, glycolic, p-aminobenzoic, glutamic, benzenesulfonic, cyclohexyl-sulfamic, gamma-amino-butyric, α-(2-hydroxyethylamino)-propionic, phosphoric, phosphonic, sulfuric, sulfonic, glucuronic and 1-methyl-1,4-dihydro nicotinic.

30. The method of claim 27 wherein the modulation of excitability of the central nervous system is effected by said neuroactive steroid compound by regulation of the chloride ion channels associated with the GABA receptor complex.

31. The method of claim 27 wherein the modulation of excitability of the central nervous system is effected by said neuroactive steroid compound by activating the GABA receptor-chloride ionophore complex (GRC) by attaching to a specific brain steroid receptor site associated with and activating said complex.

32. The method of claim 30 wherein the regulation of the chloride ion channels associated with the GABA receptor complex is effected by said neuroactive steroid compound by activating the GRC by attaching to a specific brain steroid receptor site associated with and activating said complex.

33. The method of claim 27 wherein said neuroactive steroid compound is administered in an amount sufficient to alleviate stress or anxiety in said animal.

34. The method of claim 27 wherein said neuroactive steroid compound is administered in an amount sufficient to alleviate seizure activity in said animal.

35. The method of claim 27 wherein said neuroactive steroid compound is administered in an amount sufficient to reduce or alleviate insomnia in said patient.

36. The method of claim 27 wherein said neuroactive steroid compound is administered in an amount sufficient to reduce or alleviate symptoms of PMS or PND in said patient.

37. The method of claim 27 wherein said neuroactive steroid compound is administered in an amount sufficient to treat mood disorders in said patient.

38. The method of claim 37 wherein said mood disorder is depression.

39. The method of claim 27 wherein said pharmaceutically effective amount is from about 5 mg to about 500 mg per dosage unit.

40. The method of claim 1 wherein R7 and R8 combined are =CH—CH$_3$.

41. The method of claim 40 where any said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, ε-caprolactone, ε-caprolactam, omega-thiocaprolactam and morpholine.

42. The method of claim 40 where R3 is a pharmaceutically acceptable ester of an acid selected from the group consisting of acetic, propionic, normal and isomeric forms of butyric, valeric, hexanoic, heptanoic, octanoic, nonanoic, decanoic, undecanoic and dodecanoic, cinnamic, benzylic, benzoic, maleic, fumaric, ascorbic, pimelic, succinic, bismethylenesalicylic, methanesulfonic, ethanesulfonic, oxalic, tartaric, salicylic, acetyl salicylic, citric, gluconic, aspattic, stearic, palmitic, itaconic, glycolic, p-aminobenzoic, glutamic, benzenesulfonic, cyclohexyl-sulfamic, gamma-amino-butyric, α-(2-hydroxyethylamino)-propionic, phosphoric, phosphonic, sulfuric, sulfonic, glucuronic and 1-methyl-1,4-dihydro nicotinic.

43. The method of claim 40 wherein the modulation of excitability of the central nervous system is effected by said neuroactive steroid compound by regulation of the chloride ion channels associated with the GABA receptor complex.

44. The method of claim 40 wherein the modulation of excitability of the central nervous system is effected by said neuroactive steroid compound by activating the GABA receptor-chloride ionophore complex (GRC) by attaching to a specific brain steroid receptor site associated with and activating said complex.

45. The method of claim 43 wherein the regulation of the chloride ion channels associated with the GABA receptor complex is effected by said neuroactive steroid compound by activating the GRC by attaching to a specific brain steroid receptor site associated with and activating said complex.

46. The method of claim 40 wherein said neuroactive steroid compound is administered in an amount sufficient to alleviate stress or anxiety in said animal.

47. The method of claim 40 wherein said neuroactive steroid compound is administered in an amount sufficient to alleviate seizure activity in said animal.

48. The method of claim 40 wherein said neuroactive steroid compound is administered in an amount sufficient to reduce or alleviate insomnia in said patient.

49. The method of claim 40 wherein said neuroactive steroid compound is administered in an amount sufficient to reduce or alleviate symptoms of PMS or PND in said patient.

50. The method of claim 40 wherein said neuroactive steroid compound is administered in an amount sufficient to treat mood disorders in said patient.

51. The method of claim 50 wherein said mood disorder is depression.

52. The method of claim 40 wherein said pharmaceutically effective amount is from about 5 mg to about 500 mg per dosage unit.

53. The method of claim 1 wherein R2 is selected from the group consisting of methyl, ethyl, and propyl.

54. The method of claim 53 where any said heterocyclic radicals are independently selected from the group consisting of tetrahydrofuran, 1,4-dioxane, 1,3,5-trioxane, pyrrolidine, piperidine, quinuclidine, pyzidine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, ε-caprolactone, ε-caprolactam, omega-thiocaprolactam and morpholine.

55. The method of claim 53 where R3 is a pharmaceutically acceptable ester of an acid selected from the group consisting of acetic, propionic, normal and isomeric forms of butyric, valeric, hexanoic, heptanoic, octanoic, nonanoic, decanoic, undecanoic and dodecanoic, cinnamic, benzylic, benzoic, maleic, fumaric, ascorbic, pimelic, succinic, bismethylenesalicylic, methanesulfonic, ethanesulfonic, oxalic, tartaric, salicylic, acetyl salicylic, citric, gluconic, aspartic, stearic, palmitic, itaconic, glycolic, p-aminobenzoic, glutamic, benzenesulfonic, cyclohexyl-sulfamic, gamma-amino-butyric, α-(2-hydroxyethylamino)-propionic, phosphoric, phosphonic, sulfuric, sulfonic, glucuronic and 1-methyl-1,4-dihydro nicotinic.

56. The method of claim 53 wherein the modulation of excitability of the central nervous system is effected by said neuroactive steroid compound by regulation of the chloride ion channels associated with the GABA receptor complex.

57. The method of claim 53 wherein the modulation of excitability of the central nervous system is effected by said neuroactive steroid compound by activating the GABA receptor-chloride ionophore complex (GRC) by attaching to a specific brain steroid receptor site associated with and activating said complex.

58. The method of claim 56 wherein the regulation of the chloride ion channels associated with the GABA receptor complex is effected by said neuroactive steroid compound by activating the GRC by attaching to a specific brain steroid receptor site associated with and activating said complex.

59. The method of claim 53 wherein said neuroactive steroid compound is administered in an amount sufficient to alleviate stress or anxiety in said animal.

60. The method of claim 53 wherein said neuroactive steroid compound is administered in an amount sufficient to alleviate seizure activity in said animal.

61. The method of claim 53 wherein said neuroactive steroid compound is administered in an amount sufficient to reduce or alleviate insomnia in said patient.

62. The method of claim 53 wherein said neuroactive steroid compound is administered in an amount sufficient to reduce or alleviate symptoms of PMS or PND in said patient.

63. The method of claim 53 wherein said neuroactive steroid compound is administered in an amount sufficient to treat mood disorders in said patient.

64. The method of claim 63 wherein said mood disorder is depression.

65. The method of claim 53 wherein said pharmaceutically effective amount is from about 5 mg to about 500 mg per dosage unit.

66. The method of claim 1 wherein R8 is (1S)-1-hydroxyethyl.

67. The method of claim 66 where any said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, $\epsilon$-caprolactone, $\epsilon$-caprolactam, omega-thiocaprolactam and morpholine.

68. The method of claim 66 where R3 is a pharmaceutically acceptable ester of an acid selected from the group consisting of acetic, propionic, normal and isomeric forms of butyric, valeric, hexanoic, heptanoic, octanoic, nonanoic, decanoic, undecanoic and dodecanoic, cinnamic, benzylic, benzoic, maleic, fumaric, ascorbic, pimelic, succinic, bismethylenesalicylic, methanesulfonic, ethanesulfonic, oxalic, tartaric, salicylic, acetyl salicylic, citric, gluconic, aspartic, stearic, palmitic, itaconic, glycolic, p-aminobenzoic, glutamic, benzenesulfonic, cyclohexyl-sulfamic, gamma-amino-butyric, $\alpha$-(2-hydroxyethylamino)-propionic, phosphoric, phosphonic, sulfuric, sulfonic, glucuronic and 1-methyl-1,4-dihydro nicotinic.

69. The method of claim 66 wherein the modulation of excitability of the central nervous system is effected by said neuroactive steroid compound by regulation of the chloride ion channels associated with the GABA receptor complex.

70. The method of claim 66 wherein the modulation of excitability of the central nervous system is effected by said neuroactive steroid compound by activating the GABA receptor-chloride ionophore complex (GRC) by attaching to a specific brain steroid receptor site associated with and activating said complex.

71. The method of claim 69 wherein the regulation of the chloride ion channels associated with the GABA receptor complex is effected by said neuroactive steroid compound by activating the GRC by attaching to a specific brain steroid receptor site associated with and activating said complex.

72. The method of claim 66 wherein said neuroactive steroid compound is administered in an amount sufficient to alleviate stress or anxiety in said animal.

73. The method of claim 66 wherein said neuroactive steroid compound is administered in an amount sufficient to alleviate seizure activity in said animal.

74. The method of claim 66 wherein said neuroactive steroid compound is administered in an amount sufficient to reduce or alleviate insomnia in said patient.

75. The method of claim 66 wherein said neuroactive steroid compound is administered in an amount sufficient to reduce or alleviate symptoms of PMS or PND in said patient.

76. The method of claim 66 wherein said neuroactive steroid compound is administered in an amount sufficient to treat mood disorders in said patient.

77. The method of claim 76 wherein said mood disorder is depression.

78. The method of claim 66 wherein said pharmaceutically effective amount is from about 5 mg to about 500 mg per dosage unit.

79. The method of claim 1 wherein (A) R2 is not hydrogen; and (B) R8 is cyano —C≡N.

80. The method of claim 79 where any said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furrural, furfuryl alcohol, carbazole, isoquinoline, 3-pyrroline, thiophene, furan, hexamethyleneimine, $\epsilon$-caprolactone, $\epsilon$-caprolactam, omega-thiocaprolactam and morpholine.

81. The method of claim 79 where R3 is a pharmaceutically acceptable ester of an acid selected from the group consisting of acetic, propionic, normal and isomeric forms of butyric, valeric, hexanoic, heptanoic, octanoic, nonanoic, decanoic, undecanoic and dodecanoic, cinnamic, benzylic, benzoic, maleic, fumaric, ascorbic, pimelic, succinic, bismethylenesalicylic, methanesulfonic, ethanesulfonic, oxalic, tartaric, salicylic, acetyl salicylic, citric, gluconic, aspartic, stearic, palmitic, itaconic, glycolic, p-aminobenzoic, glutamic, benzenesulfonic, cyclohexyl-sulfamic, gamma-amino-butyric, $\alpha$-(2-hydroxyethylamino)-propionic, phosphoric, phosphonic, sulfuric, sulfonic, glucuronic and 1-methyl-1,4-dihydro nicotinic.

82. The method of claim 79 wherein the modulation of excitability of the central nervous system is effected by said neuroactive steroid compound by regulation of the chloride ion channels associated with the GABA receptor complex.

83. The method of claim 79 wherein the modulation of excitability of the central nervous system is effected by said neuroactive steroid compound by activating the GABA receptor-chloride ionophore complex (GRC) by attaching to a specific brain steroid receptor site associated with and activating said complex.

84. The method of claim 82 wherein the regulation of the chloride ion channels associated with the GABA receptor complex is effected by said neuroactive steroid compound by activating the GRC by attaching to a specific brain steroid receptor site associated with and activating said complex.

85. The method of claim 79 wherein said neuroactive steroid compound is administered in an amount sufficient to alleviate stress or anxiety in said animal.

86. The method of claim 79 wherein said neuroactive steroid compound is administered in an amount sufficient to alleviate seizure activity in said animal.

87. The method of claim 79 wherein said neuroactive steroid compound is administered in an amount sufficient to reduce or alleviate insomnia in said patient.

88. The method of claim 79 wherein said neuroactive steroid compound is administered in an amount sufficient to reduce or alleviate symptoms of PMS or PND in said patient.

89. The method of claim 79 wherein said neuroactive steroid compound is administered in an amount sufficient to treat mood disorders in said patient.

90. The method of claim 89 wherein said mood disorder is depression.

91. The method of claim 79 wherein said pharmaceutically effective amount is from about 5 mg to about 500 mg per dosage unit.

92. A compound of formula I:

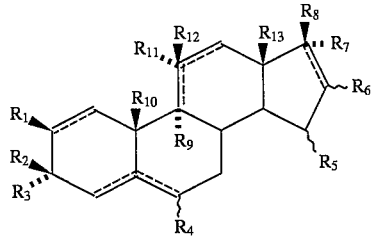

wherein

A) $R1$, $R4$, $R5$, and $R6$ are individually selected from the group consisting of:
  (1) hydrogen, hydroxyl, or thiol;
  (2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
  (3) halogen atoms; and
  (4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;

B) $R2$ is selected from the group consisting of
  (1) hydrogen; and
  (2) a $C_1$ halogenated or unhalogenated radical, $C_2$–$C_4$ saturated or unsaturated, halogenated or unhalogenated straight chain radicals, and $C_3$–$C_4$ saturated or unsaturated, halogenated or unhalogenated branched chain radicals; except that where R3 is hydroxyl and R10 and R13 are both methyl, R2 is not hydrogen;

C) $R3$ is selected from the group consisting of:
  (1) hydroxyl or thiol;
  (2) pharmaceutically acceptable ester and thioester groups

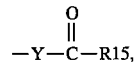

wherein R15 is hydrogen or a $C_1$ halogenated or unhalogenated radical, a $C_2$–$C_{20}$ saturated or unsaturated, halogenated or unhalogenated straight chain radical, a $C_3$–$C_{20}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
  (3) pharmaceutically acceptable cleavable esters of natural or synthetic amino acids;
  (4) pharmaceutically acceptable acyloxyalkyloxy or acyloxyalkylthio

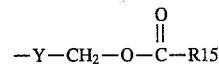

radicals, wherein Y and R15 are as previously defined; and
  (5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

D) $R7$ is selected from the group consisting of
  (1) hydrogen or hydroxyl;
  (2) halogen atoms;
  (3) pharmaceutically acceptable ether and thioether groups —Y—R23, wherein R23 is a $C_1$ halogenated or unhalogenated radical, a $C_2$–$C_4$ saturated or unsaturated, halogenated or unhalogenated straight chain radical, or a $C_3$–$C_4$ saturated or unsaturated, halogenated or unhalogenated branched chain radical, and Y is as previously defined; and
  (4) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
except when the bond between carbons C16–C17 in formula I is a double bond, R7 is not present;

E) $R8$ is (1S)-1-hydroxyethyl;

F) $R9$ is selected from the group consisting of
  (1) hydrogen; and
  (2) $C_1$–$C_6$ alkyl, halo-, dihalo-, and trihaloalkyl, or $C_6$ aryl, halo-, dihalo-, and trihaloaryl; except if the bond between carbons C9–C11 in formula I is a double bond, then R9 is not present;

G) $R10$ and $R13$ are individually selected from the group consisting of $C_1$–$C_6$ alkyl, halo-, dihalo-, and trihaloalkyl, or $C_6$ aryl, halo-, dihalo-, and trihaloaryl; and H) one of $R11$ and $R12$ is hydrogen, and the other is selected from the group consisting of
  (1) hydrogen, hydroxyl, or thiol;

(2) $C_1$–$C_{10}$ alkyloxy and alkylthio radicals, $C_6$–$C_{10}$ aryloxy and arylthio radicals, or amino radicals;
(3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
(4) pharmaceutically acceptable

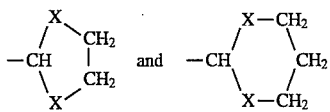

groups wherein each X independently is oxygen, nitrogen, or sulfur;
or together R11 and R12 make a double bond to oxygen or sulfur to form the ketone or thioketone; except if the bond between carbons C9–C11 or C11–C12 in formula I is a double bond, then R12 is not present.

93. The compound of claim 92 where said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, ε-caprolactone, ε-caprolactam, omega-thiocaprolactam and morpholine.

94. A compound of formula I:

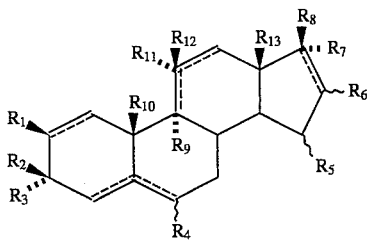

wherein
A) R1, R4, R5, and R6 are individually selected from the group consisting of:
(1) hydrogen, hydroxyl, or thiol;
(2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
(3) halogen atoms; and
(4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;
B) R2 is selected from the group consisting of
(1) hydrogen; and
(2) a $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
C) R3 is selected from the group consisting of:
(1) hydroxyl or thiol;
(2) pharmaceutically acceptable ester and thioester groups

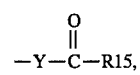

wherein R15 is hydrogen or a $C_1$ halogenated or unhalogenated radical, a $C_2$–$C_{20}$ saturated or unsaturated, halogenated or unhalogenated straight chain radical, a $C_3$–$C_{20}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
(3) pharmaceutically acceptable cleavable esters of natural or synthetic amino acids;
(4) pharmaceutically acceptable acyloxyalkyloxy or acyloxyalkylthio

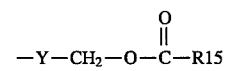

radicals, wherein Y and R15 are as previously defined; and
(5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;
D) R7 is selected from the group consisting of
(1) hydrogen or hydroxyl;
(2) halogen atoms;
(3) pharmaceutically acceptable ether and thioether groups —Y—R23, wherein R23 is a $C_1$ halogenated or unhalogenated radical, a $C_2$–$C_4$ saturated or unsaturated, halogenated or unhalogenated straight chain radical, or a $C_3$–$C_4$ saturated or unsaturated, halogenated or unhalogenated branched chain radical, and Y is as previously defined; and
(4) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
except when the bond between carbons C16–C17 in formula I is a double bond, R7 is not present;

E) R8 is

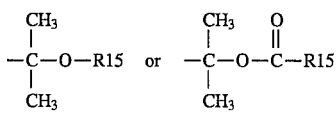

wherein R15 is as previously defined;

F) R9 is selected from the group consisting of
  (1) hydrogen; and
  (2) $C_1$–$C_6$ alkyl, halo-, dihalo-, and trihaloalkyl, or $C_6$ aryl, halo-, dihalo-, and trihaloaryl; except if the bond between carbons C9–C11 in formula I is a double bond, then R9 is not present;

G) R10 and R13 are individually selected from the group consisting of
  (1) hydrogen; and
  (2) $C_1$–$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
  (1) hydrogen, hydroxyl, or thiol;
  (2) $C_1$–$C_{10}$ alkyloxy and alkylthio radicals, $C_6$–$C_{10}$ aryloxy and arylthio radicals, or amino radicals;
  (3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
  (4) pharmaceutically acceptable

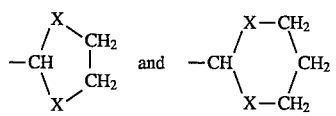

groups wherein each X independently is oxygen, nitrogen, or sulfur;
or together R11 and R12 make a double bond to oxygen or sulfur to form the ketone or thioketone; except if the bond between carbons C9–C11 or C11–C12 in formula I is a double bond, then R12 is not present.

95. The compound of claim 94 where said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, ε-caprolactone, ε-caprolactam, omega-thiocaprolactam and morpholine.

96. A compound of formula I:

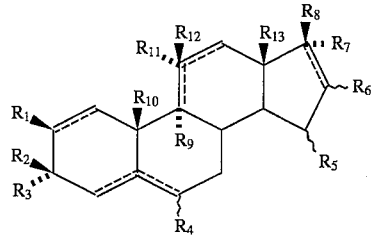

wherein

A) R1, R4, R5, and R6 are individually selected from the group consisting of:
  (1) hydrogen, hydroxyl, or thiol;
  (2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
  (3) halogen atoms; and
  (4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;

B) R2 is selected from the group consisting of
  (1) hydrogen; and
  (2) a $C_1$ halogenated or unhalogenated radical, $C_2$–$C_4$ saturated or unsaturated, halogenated or unhalogenated straight chain radicals, and $C_3$–$C_4$ saturated or unsaturated, halogenated or unhalogenated branched chain radicals; except that where R3 is hydroxyl and R10 and R13 are both methyl, R2 is not hydrogen;

C) R3 is selected from the group consisting of:
  (1) hydroxyl or thiol;
  (2) pharmaceutically acceptable ester and thioester groups

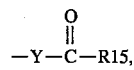

wherein R15 is hydrogen or a $C_1$ halogenated or unhalogenated radical, a $C_2$–$C_{20}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
  (3) pharmaceutically acceptable cleavable esters of natural or synthetic amino acids;

(4) pharmaceutically acceptable acyloxyalkyloxy or acyloxyalkylthio

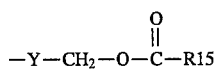

radicals, wherein Y and R15 are as previously defined; and
(5) pharmaceutically acceptable esters or thioesters of the aforementioned hydroxyl or thiol groups with an acid selected from the group consisting of cinnamic, maleic, fumaric, ascorbic, pimelic, succinic. bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

D) R7 and R8 combined are =CH—CH$_3$;

E) R9 is selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl; except if the bond between carbons C9–C11 in formula I is a double bond, then R9 is not present;

F) R10 and R13 are individually selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl; and G) one of R11 and R12 is hydrogen, and the other is selected from the group consisting of
(1) hydrogen, hydroxyl, or thiol;
(2) $C_1$–$C_{10}$ alkyloxy and alkylthio radicals, $C_6$–$C_{10}$ aryloxy and arylthio radicals, or amino radicals;
(3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
(4) pharmaceutically acceptable

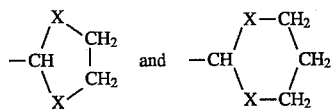

groups wherein each X independently is oxygen, nitrogen, or sulfur;
or together R11 and R12 make a double bond to oxygen or sulfur to form the ketone or thioketone; except if the bond between carbons C9–C11 or C11–C12 in formula I is a double bond, then R12 is not present.

97. The compound of claim 96 where said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, ε-caprolactone, ε-caprolactam, omega-thiocaprolactam and morpholine.

98. A compound of formula I:

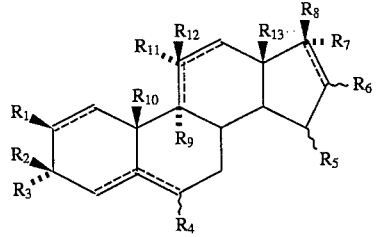

wherein
A) R1, R4, R5, and R6 are individually selected from the group consisting of:
(1) hydrogen, hydroxyl, or thiol;
(2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
(3) halogen atoms; and
(4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;

B) R2 is selected from the group consisting of
(1) hydrogen; and
(2) a $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;

C) R3 is selected from the group consisting of:
(1) hydroxyl or thiol;
(2) pharmaceutically acceptable ester and thioester groups

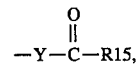

wherein R15 is hydrogen or a $C_1$ halogenated or unhalogenated radical, a $C_2$–$C_{20}$ saturated or unsaturated, halogenated or unhalogenated straight chain radical, a $C_3$–$C_{20}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
(3) pharmaceutically acceptable cleavable esters of natural or synthetic amino acids;

(4) pharmaceutically acceptable acyloxyalkyloxy or acyloxyalkylthio $$-Y-CH_2-O-\overset{O}{\underset{\|}{C}}-R15$$

radicals, wherein Y and R15 are as previously defined; and (5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

D) R7 is selected from the group consisting of
  (1) hydrogen or hydroxyl;
  (2) halogen atoms;
  (3) pharmaceutically acceptable ether and thioether groups —Y—R23, wherein R23 is a $C_1$ halogenated or unhalogenated radical, a $C_2$–$C_4$ saturated or unsaturated, halogenated or unhalogenated straight chain radical, or a $C_3$–$C_4$ saturated or unsaturated, halogenated or unhalogenated branched chain radical, and Y is as previously defined; and
  (4) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;

except when the bond between carbons C16–C17 in formula I is a double bond, R7 is not present;

E) R8 is a pharmaceutically acceptable thiazolidine derivative having the formula:

wherein any two of R17, R18, R19 and R20 are individually hydrogen, a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually $$-\overset{O}{\underset{\|}{C}}-O-R15,$$

wherein R15 is as previously defined;

F) R9 is selected from the group consisting of
  (1) hydrogen; and (2) $C_1$–$C_6$ alkyl, halo-, dihalo-, and trihaloalkyl, or $C_6$ aryl, halo-, dihalo-, and trihaloaryl; except if the bond between carbons C9–C11 in formula I is a double bond, then R9 is not present;

G) R10 and R13 are individually selected from the group consisting of
  (1) hydrogen; and
  (2) $C_1$–$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
  (1) hydrogen, hydroxyl, or thiol;
  (2) $C_1$–$C_{10}$ alkyloxy and alkylthio radicals, $C_6$–$C_{10}$ aryloxy and arylthio radicals, or amino radicals;
  (3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
  (4) pharmaceutically acceptable groups wherein each X independently is oxygen, nitrogen, or sulfur;

or together R11 and R12 make a double bond to oxygen or sulfur to form the ketone or thioketone; except if the bond between carbons C9–C11 or C11–C12 in formula I is a double bond, then R12 is not present.

99. The compound of claim 98 where said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine thymine, uracil, adenine, guanine, pyrazine, 1-methyl-1,4-dihydronicotine, picolinic acid, picoline, furoic acid, furrural, furfuryl alcohol, carbazole, isoquinoline, 3-pyrroline, thiophene, furan, hexamethyleneimine, ε-caprolactone, ε-caprolactam, omega-thiocaprolactam and morpholine.

100. A compound of formula I:

wherein
  A) R1, R4, R5, and R6 are individually selected from the group consisting of:
    (1) hydrogen, hydroxyl, or thiol;
    (2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
   (3) halogen atoms; and
   (4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;
B) R2 is selected from the group consisting of methyl, ethyl, and propyl;
C) R3 is selected from the group consisting of:
   (1) hydroxyl or thiol;
   (2) pharmaceutically acceptable ester and thioester groups

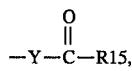

wherein R15 is hydrogen or a $C_1$ halogenated or unhalogenated radical, a $C_2$–$C_{20}$ saturated or unsaturated, halogenated or unhalogenated straight chain radical, a $C_3$–$C_{20}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
   (3) pharmaceutically acceptable cleavable esters of natural or synthetic amino acids;
   (4) pharmaceutically acceptable acyloxyalkyloxy or acyloxyalkylthio

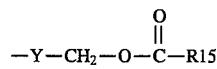

radicals, wherein Y and R15 are as previously defined; and
   (5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;
D) R7 is selected from the group consisting of
   (1) hydrogen or hydroxyl;
   (2) halogen atoms;
   (3) pharmaceutically acceptable ether and thioether groups —Y—R23, wherein R23 is a $C_1$ halogenated or unhalogenated radical, a $C_2$–$C_4$ saturated or unsaturated, halogenated or unhalogenated straight chain radical, or a $C_3$–$C_4$ saturated or unsaturated, halogenated or unhalogenated branched chain radical, and Y is as previously defined; and
   (4) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
except when R8 is hydroxyl, R7 is not hydroxyl; when R8 is hydroxyl or thiol, R7 is not halogen, an ether, or a thioether; and when the bond between carbons C16–C17 in formula I is a double bond, R7 is not present;

E) R8 is selected from the group consisting of:
   (1) hydroxyl, thiol, or 2-hydroxyethanoyl;

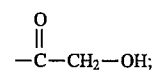

(2) pharmaceutically acceptable ester or thioester groups

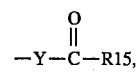

wherein Y and R15 are as previously defined;
   (3) pharmaceutically acceptable

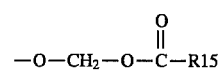

groups wherein R15 is as previously defined;
   (4) pharmaceutically acceptable

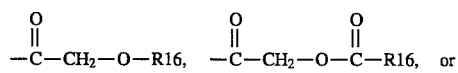

groups wherein R16 is a $C_8$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide

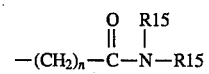

radical where n is 1–10, R15 is as previously defined, and each R15 is independently determined;
   (5) pharmaceutically acceptable oxime

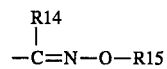

groups, where R14 and R15 are as previously defined;

(6) pharmaceutically acceptable thiazolidine derivatives having the formula:

$$\begin{array}{c} \phantom{xx} \text{R17} \\ \phantom{xx} | \\ (CH_3) \quad S\text{---}C\text{---}R18 \\ \diagdown C \diagup \\ \diagup \phantom{x} \diagdown \\ \phantom{xxx} NH\text{---}C\text{---}R19 \\ \phantom{xxxxxx} | \\ \phantom{xxxxxx} R20 \end{array}$$

wherein any two of R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually $$\begin{array}{c} O \\ \| \\ \text{---}C\text{---}O\text{---}R15, \end{array}$$

wherein R15 is as previously defined;

(7) pharmaceutically acceptable $$\begin{array}{ccc} \text{R21} & & \text{R21} \quad O \\ | & & | \quad \| \\ \text{---}C\text{---}O\text{---}R15 \quad \text{and} & \text{---}C\text{---}O\text{---}C\text{---}R15 \\ | & & | \\ \text{R22} & & \text{R22} \end{array}$$

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined; and (8) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

F) R9 is selected from the group consisting of
  (1) hydrogen; and
  (2) $C_1$–$C_6$ alkyl, halo-, dihalo-, and trihaloalkyl, or $C_6$ aryl, halo-, dihalo-, and trihaloaryl; except if the bond between carbons C9–C11 in formula I is a double bond, then R9 is not present;

G) R10 and R13 are individually selected from the group consisting of
  (1) hydrogen; and
  (2) $C_1$–$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
  (1) hydrogen, hydroxyl, or thiol;
  (2) $C_1$–$C_{10}$ alkyloxy and alkylthio radicals, $C_6$–$C_{10}$ aryloxy and arylthio radicals, or amino radicals;
  (3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
  (4) pharmaceutically acceptable $$\begin{array}{cc} \diagup X \diagdown & \diagup X\text{---}CH_2 \diagdown \\ \text{---}CH \quad CH_2 & \text{---}CH \quad CH_2 \\ \diagdown \diagup CH_2 \quad \text{and} & \diagdown \quad \diagup \\ \phantom{xx} X & \phantom{xx} X\text{---}CH_2 \end{array}$$

groups wherein each X independently is oxygen, nitrogen, or sulfur;

or together R11 and R12 make a double bond to oxygen or sulfur to form the ketone or thioketone; except if the bond between carbons C9–C11 or C11–C12 in formula I is a double bond, then R12 is not present.

101. The compound of claim 100 where said heterocyclic radicals are independently selected from the group consisting of tetrahydrofuran, 1,4-dioxane, 1,3,5-trioxane, pyrrolidine, piperidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamethyleneimine, ε-caprolactone, ε-caprolactam, omega-thiocaprolactam and morpholine.

102. A method for treating or preventing seizures in an animal in need of such treatment or prevention, comprising administering to said animal a therapeutically effective amount of a neuroactive steroid compound of formula I:

wherein
A) R1, R4, R5, and R6 are individually selected from the group consisting of:
  (1) hydrogen, hydroxyl, or thiol;
  (2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
  (3) halogen atoms; and
  (4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;
B) R2 is selected from the group consisting of
  (1) hydrogen; and
  (2) a $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
C) R3 is selected from the group consisting of:
  (1) hydroxyl or thiol;
  (2) pharmaceutically acceptable ester and thioester groups

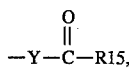

wherein R15 is hydrogen or a $C_1$ halogenated or unhalogenated radical, a $C_2$–$C_{20}$ saturated or unsaturated, halogenated or unhalogenated straight chain radical, a $C_3$–$C_{20}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
  (3) pharmaceutically acceptable cleavable esters of natural or synthetic amino acids;
  (4) pharmaceutically acceptable acyloxyalkyloxy or acyloxyalkylthio

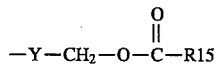

radicals, wherein Y and R15 are as previously defined; and
  (5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;
D) R7 is selected from the group consisting of
  (1) hydrogen or hydroxyl;
  (2) halogen atoms;
  (3) pharmaceutically acceptable ether and thioether groups —Y—R23, wherein R23 is a $C_1$ halogenated or unhalogenated radical, a $C_2$–$C_4$ saturated or unsaturated, halogenated or unhalogenated straight chain radical, or a $C_3$–$C_4$ saturated or unsaturated, halogenated or unhalogenated branched chain radical, and Y is as previously defined; and
  (4) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
except when R8 is hydroxyl, R7 is not hydroxyl; when R8 is hydroxyl or thiol, R7 is not halogen, an ether, or a thioether: and when the bond between carbons C16–C17 in formula I is a double bond, R7 is not present;
E) R8 is selected from the group consisting of:
  (1) hydroxyl, thiol, 2-hydroxyethanoyl

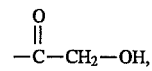

or 1-hydroxyethyl

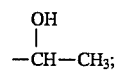

(2) pharmaceutically acceptable ester or thioester groups

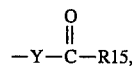

wherein Y and R15 are as previously defined;
  (3) pharmaceutically acceptable

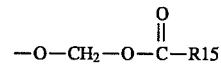

groups wherein R15 is as previously defined;
  (4) pharmaceutically acceptable

groups, wherein R15 is as previously defined;
  (5) pharmaceutically acceptable

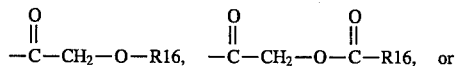

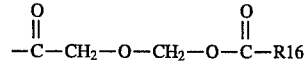

groups, wherein R16 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide

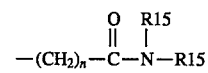

radical where n is 1–10, R15 is as previously defined, and each R15 is independently determined;

(6) pharmaceutically acceptable oxime

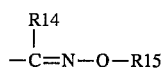

groups, where R14 and R15 are as previously defined;
(7) pharmaceutically acceptable thiazolidine derivatives having the formula:

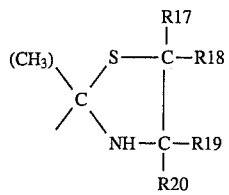

wherein any two of R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

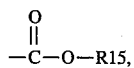

wherein R15 is as previously defined;
(8) pharmaceutically acceptable

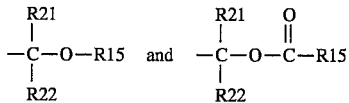

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, or a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined;
(9) pharmaceutically acceptable carboxylate

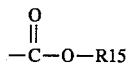

groups wherein R15 is as previously defined;
(10) pharmaceutically acceptable

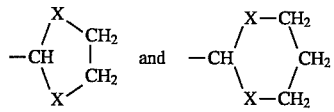

groups wherein each X independently is oxygen, nitrogen, or sulfur;
(11) cyano —C≡N; and
(12) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic; or R7 and R8 combined are =CH—$CH_3$; except when R3 is hydroxyl and R2 is hydrogen and R10 and R13 are both methyl, R8 is not acetyl:

F) R9 is selected from the group consisting of
(1) hydrogen; and
(2) $C_1$–$C_6$ alkyl, halo-, dihalo, and trihaloalkyl, or $C_6$ aryl, halo-, dihalo-, and trihaloaryl, except if the bond between carbons C9–C11 in formula I is a double bond, then R9 is not present;

G) R10 and R13 are individually selected from the group consisting of
(1) hydrogen; and
(2) $C_1$–$C_6$ alkyl, halo-, dihalo, and trihaloalkyl, or $C_6$ aryl, halo-, dihalo-, and trihaloaryl; and H) one of R11 and R12 is hydrogen, and the other is selected from the group consisting of
(1) hydrogen, hydroxyl, or thiol;
(2) $C_1$–$C_{10}$ alkyloxy and alkylthio radicals, $C_6$–$C_{10}$ aryloxy and arylthio radicals, or amino radicals;
(3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
(4) pharmaceutically acceptable

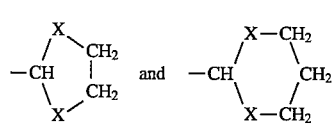

groups wherein each X independently is as previously defined;
or together R11 and R12 make a double bond to oxygen or sulfur to form the ketone or thioketone; except if the bond between carbons C9–C11 or C11–C12 in formula I is a double bond, then R12 is not present.

103. The method of claim 102 wherein the neuroactive steroid compound is selected from the group consisting of 3α-hydroxy-2β-methoxy-5α-pregnan-20-one, 3α,21-dihydroxy-5α-pregnan-20-one, 3α,20α-dihydroxy-5α-pregnane, 3α,20-dihydroxy-20-methyl-5α-pregnane 3α,20-dihydroxy-3β,20-dimethyl-5α-pregnane, 3α-hydroxy-3β-methyl-5α-pregnan-20-one, 3α-hydroxy-5α-pregnan-20-one, and 3α-isobutyryloxy-5α-pregnan-20-one.

104. The method of claim 102 wherein the neuroactive steroid compound is 3α-hydroxy-3β-methyl-5α-pregnan-20-one.

105. A method for treating or preventing anxiety in an animal in need of such treatment or prevention, comprising administering to said animal a therapeutically effective amount of a neuroactive steroid compound of the formula I:

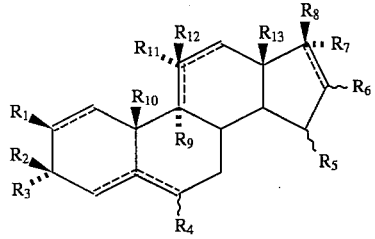

wherein
A) $R_1$, $R_4$, $R_5$, and $R_6$ are individually selected from the group consisting of:
  (1) hydrogen, hydroxyl, or thiol;
  (2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
  (3) halogen atoms; and
  (4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;
B) $R_2$ is selected from the group consisting of
  (1) hydrogen; and
  (2) a $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
C) $R_3$ is selected from the group consisting of:
  (1) hydroxyl or thiol;
  (2) pharmaceutically acceptable ester and thioester groups

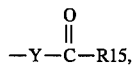

wherein R15 is hydrogen or a $C_1$ halogenated or unhalogenated radical, a $C_2$–$C_{20}$ saturated or unsaturated, halogenated or unhalogenated straight chain radical, a $C_3$–$C_{20}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
  (3) pharmaceutically acceptable cleavable esters of natural or synthetic amino acids;
  (4) pharmaceutically acceptable acyloxyalkyloxy or acyloxyalkylthio

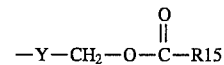

radicals, wherein Y and R15 are as previously defined; and
  (5) pharmaceutically acceptable esters or thioesters of the aforementioned hydroxyl or thiol groups with an acid selected from the group consisting of cinnamic, maleic, fumaric, ascorbic, pimelic, succinic, bism-ethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;
D) R7 is selected from the group consisting of
  (1) hydrogen or hydroxyl;
  (2) halogen atoms;
  (3) pharmaceutically acceptable ether and thioether groups —Y—R23, wherein R23 is a $C_1$ halogenated or unhalogenated radical, a $C_2$–$C_4$ saturated or unsaturated, halogenated or unhalogenated straight chain radical, or a $C_3$–$C_4$ saturated or unsaturated, halogenated or unhalogenated branched chain radical, and Y is as previously defined; and
  (4) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
except when R8 is hydroxyl, R7 is not hydroxyl; when R8 is hydroxyl or thiol, R7 is not halogen, an ether, or a thioether; and when the bond between carbons C16–C17 in formula I is a double bond, R7 is not present;
E) R8 is selected from the group consisting of:
  (1) hydroxyl, thiol, 2-hydroxyethanoyl

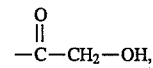

or 1-hydroxyethyl

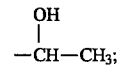

(2) pharmaceutically acceptable ester or thioester groups

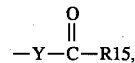

wherein Y and R15 are as previously defined;
  (3) pharmaceutically acceptable

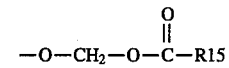

groups wherein R15 is as previously defined;

(4) pharmaceutically acceptable

groups, wherein R15 is as previously defined;
(5) pharmaceutically acceptable

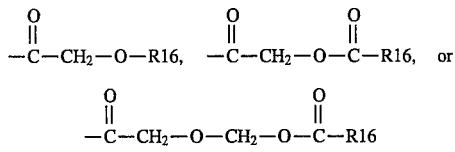

groups, wherein R16 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide

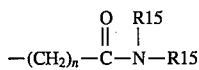

radical where n is 1–10, R15 is as previously defined, and each R15 is independently determined;
(6) pharmaceutically acceptable oxime

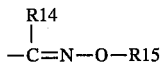

groups, where R14 and R15 are as previously defined;
(7) pharmaceutically acceptable thiazolidine derivatives having the formula:

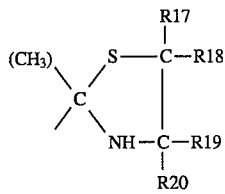

wherein any two of R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

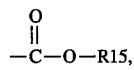

wherein R15 is as previously defined;

(8) pharmaceutically acceptable

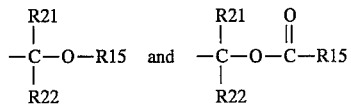

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, or a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined;
(9) pharmaceutically acceptable carboxylate

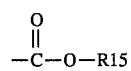

groups wherein R15 is as previously defined;
(10) pharmaceutically acceptable

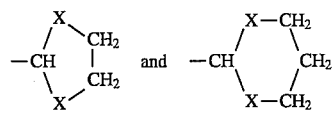

groups wherein each X independently is oxygen, nitrogen, or sulfur;
(11) cyano —C≡N; and
(12) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic; or R7 and R8 combined are =CH—$CH_3$; except when R3 is hydroxyl and R2 is hydrogen and R10 and R13 are both methyl, R8 is not 2-hydroxyethanoyl;

F) R9 is selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl, except if the bond between carbons C9–C11 in formula I is a double bond, then R9 is not present;

G) R10 and R13 are individually selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
(1) hydrogen, hydroxyl, or thiol;
(2) $C_1$–$C_{10}$ alkyloxy and alkylthio radicals, $C_6$–$C_{10}$ aryloxy and arylthio radicals, or amino radicals;
(3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and (4) pharmaceutically acceptable

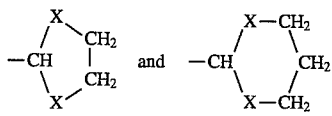

groups wherein each X independently is as previously defined;
or together R11 and R12 make a double bond to oxygen or sulfur to form the ketone or thioketone; except if the bond between carbons C9–C11 or C11–C12 in formula I is a double bond, then R12 is not present.

106. The method of claim 105 wherein the neuroactive steroid compound is selected from the group consisting of 3α-hydroxy-2β-methoxy-5α-pregnan-20-one, 3α,21-dihydroxy-5α-pregnan-20-one, 3α,20α-dihydroxy-5α-pregnane, 3α,20-dihydroxy-20-methyl-5α-pregnane, 3α,20-dihydroxy-3β,20-dimethyl-5α-pregnane, 3α-hydroxy-3β-methyl-5α-pregnan-20-one, 3α-hydroxy-5α-pregnan-20-one, and 3α-isobutyryloxy-5α-pregnan-20-one.

107. The method of claim 105 wherein the neuroactive steroid compound is 3α-hydroxy-3β-methyl-5α-pregnan-20-one.

108. A method for treating or preventing pre-menstrual syndrome in an animal in need of such treatment or prevention, comprising administering to said animal a therapeutically effective amount of a neuroactive steroid compound of the formula I:

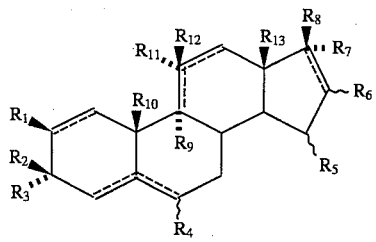

wherein
A) R1, R4, R5, and R6 are individually selected from the group consisting of:
(1) hydrogen, hydroxyl, or thiol;
(2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radials with two or more adjacent O or S atoms and Y is either a divalent oxygen or sulfur linkage;
(3) halogen atoms; and
(4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;

B) R2 is selected from the group consisting of
(1) hydrogen; and
(2) a $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;

C) R3 is selected from the group consisting of:
(1) hydroxy or thiol;
(2) pharmaceutically acceptable ester and thioester groups

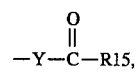

wherein R15 is hydrogen or a $C_1$ halogenated or unhalogenated radical, a $C_2$–$C_{20}$ saturated or unsaturated, halogenated or unhalogenated straight chain radical, a $C_3$–$C_{20}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
(3) pharmaceutically acceptable cleavable esters of natural or synthetic amino acids;
(4) pharmaceutically acceptable acyloxyalkyloxy or acyloxyalkylthio

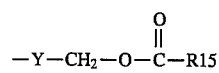

radicals, wherein Y and R15 are as previously defined; and
(5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

D) R7 is selected from the group consisting of
(1) hydrogen or hydroxyl;
(2) halogen atoms;
(3) pharmaceutically acceptable ether and thioether groups —Y—R23, wherein R23 is a $C_1$ halogenated or unhalogenated radical, a $C_2$–$C_4$ saturated or unsaturated, halogenated or unhalogenated straight chain radical, or a $C_3$–$C_4$ saturated or unsaturated, halogenated or unhalogenated branched chain radical, and Y is as previously defined; and
(4) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
except when R8 is hydroxy, R7 is not hydroxyl; when R8 is hydroxyl or thiol, R7 is not halogen, an ether, or a thioether; and when the bond between carbons C16–C17 in formula I is a double bond, R7 is not present;

E) R8 is selected from the group consisting of:
(1) hydroxyl, thiol, 2-hydroxyethanoyl

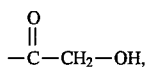

or 1-hydroxyethyl

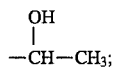

(2) pharmaceutically acceptable ester or thioester groups

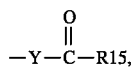

wherein Y and R15 are as previously defined;
(3) pharmaceutically acceptable

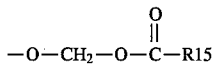

groups wherein R15 is as previously defined;
(4) pharmaceutically acceptable

groups, wherein R15 is as previously defined;
(5) pharmaceutically acceptable

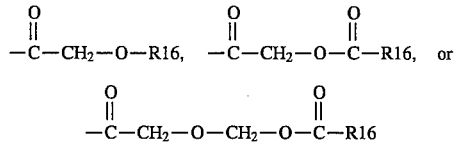

groups, wherein R16 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide

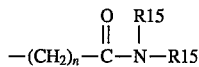

radical where n is 1–10, R15 is as previously defined, and each R15 is independently determined;
(6) pharmaceutically acceptable oxime

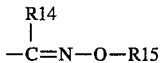

groups, where R14 and R15 are as previously defined;

(7) pharmaceutically acceptable thiazolidine derivatives having the formula:

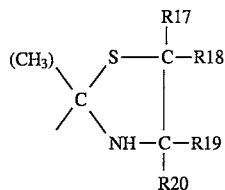

wherein any two of R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

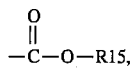

wherein R15 is as previously defined;
(8) pharmaceutically acceptable

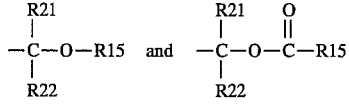

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, or a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined;
(9) pharmaceutically acceptable carboxylate

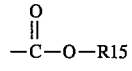

groups wherein R15 is as previously defined;
(10) pharmaceutically acceptable

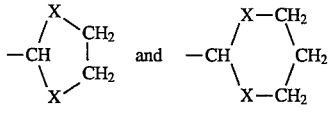

groups wherein each X independently is oxygen, nitrogen, or sulfur;
(11) cyano —C≡N; and
(12) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic; or R7 and R8 combined are =CH—CH$_3$;

F) R9 is selected from the group consisting of
  (1) hydrogen; and
  (2) C$_1$–C$_6$ alkyl, halo-, dihalo-, and trihaloalkyl, or C$_6$ aryl, halo-, dihalo-, and trihaloaryl, except if the bond between carbons C9–C11 in formula I is a double bond, then R9 is not present;

G) R10 and R13 are individually selected from the group consisting of
  (1) hydrogen; and
  (2) C$_1$–C$_6$ alkyl, halo-, dihalo-, and trihaloalkyl, or C$_6$ aryl, halo-, dihalo-, and trihaloaryl; and H) one of R11 and R12 is hydrogen, and the other is selected from the group consisting of
  (1) hydrogen, hydroxyl, or thiol;
  (2) C$_1$–C$_{10}$ alkyloxy and alkylthio radicals, C$_6$–C$_{10}$ aryloxy and arylthio radicals, or amino radicals;
  (3) a C$_1$ halogenated or unhalogenated radical, C$_2$–C$_{10}$ saturated or unsaturated, halogenated or unhalogenated straight chain radicals, C$_3$–C$_{10}$ saturated or unsaturated, halogenated or unhalogenated branched chain radicals, C$_3$–C$_{10}$ cyclic aliphatic radicals, C$_6$–C$_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
  (4) pharmaceutically acceptable

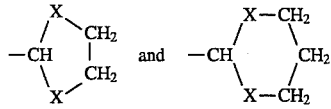

groups wherein each X independently is as previously defined;
or together R11 and R12 make a double bond to oxygen or sulfur to form the ketone or thioketone; except if the bond between carbons C9–C11 or C11–C12 in formula I is a double bond, then R12 is not present.

109. The method of claim 108 wherein the neuroactive steroid compound is selected from the group consisting of 3α-hydroxy-2β-methoxy-5α-pregnan-20-one, 3α,21-dihydroxy-5α-pregnan-20-one, 3α,20α-dihydroxy-5α-pregnane, 3α,20-dihydroxy-20-methyl-5α-pregnane, 3α,20-dihydroxy-3β,20-dimethyl-5α-pregnane, 3α-hydroxy-3β-methyl-5α-pregnan-20-one, 3α-hydroxy-5α-pregnan-20-one, and 3α-isobutyryloxy-5α-pregnan-20-one.

110. The method of claim 108 wherein the neuroactive steroid compound is 3α-hydroxy-3β-methyl-5α-pregnan-20-one.

111. A method for treating or preventing post-natal depression in an animal in need of such treatment or prevention, comprising administering to said animal a therapeutically effective amount of a neuroactive steroid compound of the formula I:

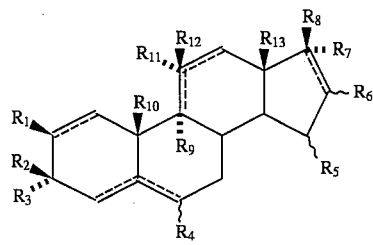

wherein
A) R1, R4, R5, and R6 are individually selected from the group consisting of:
  (1) hydrogen, hydroxyl, or thiol;
  (2) pharmaceutically acceptable ether and thioether groups —Y—R14, wherein R14 is a C$_1$ halogenated or unhalogenated radical, a C$_2$–C$_{10}$ saturated or unsaturated, halogenated or unhalogenated straight chain radical, a C$_3$–C$_{10}$ saturated or unsaturated, halogenated or unhalogenated branched chain radical, a C$_3$–C$_{10}$ cyclic aliphatic radical, a C$_6$–C$_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
  (3) halogen atoms; and
  (4) a C$_1$ halogenated or unhalogenated radical, C$_2$–C$_8$ saturated or unsaturated, halogenated or unhalogenated straight chain radicals, C$_3$–C$_8$ saturated or unsaturated, halogenated or unhalogenated branched chain radicals, or C$_3$–C$_8$ cyclic aliphatic radicals;

B) R2 is selected from the group consisting of
  (1) hydrogen; and
  (2) a C$_1$ halogenated or unhalogenated radical, C$_2$–C$_4$ saturated or unsaturated, halogenated or unhalogenated straight chain radicals, or C$_3$–C$_4$ saturated or unsaturated, halogenated or unhalogenated branched chain radicals;

C) R3 is selected from the group consisting of:
  (1) hydroxyl or thiol;
  (2) pharmaceutically acceptable ester and thioester groups

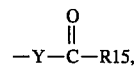

wherein R15 is hydrogen or a C$_1$ halogenated or unhalogenated radical, a C$_2$–C$_{20}$ saturated or unsaturated, halogenated or unhalogenated straight chain radical, a C$_3$–C$_{20}$ saturated or unsaturated, halogenated or unhalogenated branched chain radical, a C$_3$–C$_{10}$ cyclic aliphatic radical, a C$_6$–C$_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
  (3) pharmaceutically acceptable cleavable esters of natural or synthetic amino acids;

(4) pharmaceutically acceptable acyloxyalkyloxy or acyloxyalkylthio

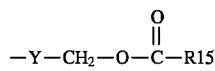

radicals, wherein Y and R15 are as previously defined; and
   (5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicyclic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;
D) R7 is selected from the group consisting of
   (1) hydrogen or hydroxyl;
   (2) halogen atoms;
   (3) pharmaceutically acceptable ether and thioether groups —Y—R23, wherein R23 is a $C_1$ halogenated or unhalogenated radical, a $C_2$–$C_4$ saturated or unsaturated, halogenated or unhalogenated straight chain radical, or a $C_3$–$C_4$ saturated or unsaturated, halogenated or unhalogenated branched chain radical, and Y is a previously defined; and
   (4) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
except when R8 is hydroxy, R7 is not hydroxyl; when R8 is hydroxyl or thiol, R7 is not halogen, an ether, or a thioether; and when the bond between carbons C16–C17 in formula I is double bond, R7 is not present;
E) R8 is selected from the group consisting of:
   (1) hydroxyl, thiol, 2-hydroxyethanoyl

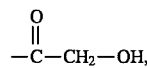

or 1-hydroxyethyl

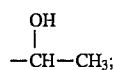

(2) pharmaceutically acceptable ester or thioester groups

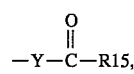

wherein Y and R15 are as previously defined;
   (3) pharmaceutically acceptable

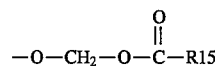

groups wherein R15 is as previously defined;

(4) pharmaceutically acceptable

groups, wherein R15 is as previously defined;
   (5) pharmaceutically acceptable

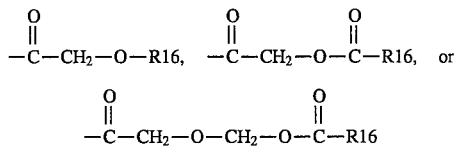

groups, wherein R16 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide

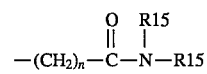

radical where n is 1–10, R15 is as previously defined, and each R15 is independently determined;
   (6) pharmaceutically acceptable oxime

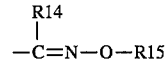

groups, where R14 and R15 are as previously defined;
   (7) pharmaceutically acceptable thiazolidine derivatives having the formula:

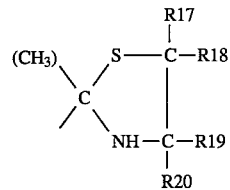

wherein any two or R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

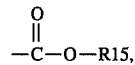

wherein R15 is as previously defined;

(8) pharmaceutically acceptable

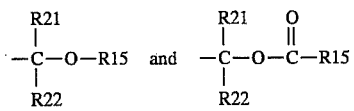

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, or a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2 or 3 heteroatoms selected from the group consisting of oxygen, nitrogen, and sulfur, excluding heterocyclic radicals with two or more adjacent O or S atoms, and R15 is as previously defined;

(9) pharmaceutically acceptable carboxylate

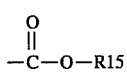

groups wherein R15 is as previously defined;

(10) pharmaceutically acceptable

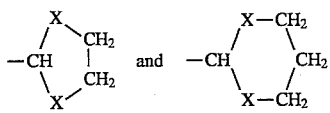

groups wherein each X independently is oxygen, nitrogen, or sulfur;

(11) cyano —C≡N; and

(12) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

or R7 and R8 combined are =CH—$CH_3$;

F) R9 is selected from the group consisting of
  (1) hydrogen; and
  (2) $C_1$–$C_6$ alkyl, halo-, dihalo-, and trihaloalkyl, or $C_6$ aryl, halo-, dihalo-, and trihaloaryl, except if the bond between carbons C9-C11 in formula I is a double bond, then R9 is not present;

G) R10 and R13 are individually selected from the group consisting of
  (1) hydrogen; and
  (2) $C_1$–$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
  (1) hydrogen, hydroxyl, or thiol;
  (2) $C_1$–$C_{10}$ alkyloxy and alkylthio radicals, $C_6$–$C_{10}$ aryloxy and arylthio radicals, or amino radicals;
  (3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and (4) pharmaceutically acceptable

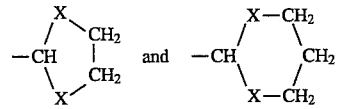

groups wherein each X independently is as previously defined;

or together R11 and R12 make a double bond to oxygen or sulfur to form the ketone or thioketone; except if the bond between carbons C9-C11 or C11-C12 in formula I is a double bond, then R12 is not present.

112. The method of claim 111 wherein the neuroactive steroid compound is selected from the group consisting of 3α-hydroxy-2β-methoxy-5α-pregnan-20-one, 3α,21-dihydroxy-5α-pregnan-20-one, 3α,20α-dihydroxy-5α-pregnane, 3α,20-dihydroxy-20-methyl-5α-pregnane, 3α,20-dihydroxy-3β,20-dimethyl-5α-pregnane, 3α-hydroxy-3β-methyl-5α-pregnan-20-one, 3α-hydroxy-5α-pregnan-20-one, and 3α-isobutyryloxy-5α-pregnan-20-one.

113. The method of claim 111 wherein the neuroactive steroid compound is 3α-hydroxy-3β-methyl-5α-pregnan-20-one.

114. A method for treating or preventing mood disorders that are amenable to GR-active agents in an animal in need of such treatment or prevention comprising administering to said animal a therapeutically effective amount of a neuroactive steroid compound of the formula I:

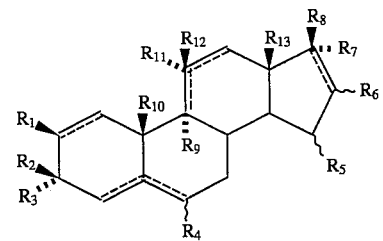

wherein

A) R1, R4, R5, and R6 are individually selected from the group consisting of:
  (1) hydrogen, hydroxyl, or thiol;
  (2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
  (3) halogen atoms; and
  (4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;

B) R2 is selected from the group consisting of
  (1) hydrogen; and
  (2) a $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
C) R3 is selected from the group consisting of:
  (1) hydroxyl or thiol;
  (2) pharmaceutically acceptable ester and thioester groups

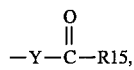

wherein R15 is hydrogen or a $C_1$ halogenated or unhalogenated radical, a $C_2$–$C_{20}$ saturated or unsaturated, halogenated or unhalogenated straight chain radical, a $C_3$–$C_{20}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
  (3) pharmaceutically acceptable cleavable esters of natural or synthetic amino acids;
  (4) pharmaceutically acceptable acyloxyalkyloxy or acyloxyalkylthio

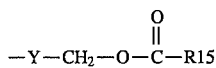

radicals, wherein Y and R15 are as previously defined; and
  (5) pharmaceutically acceptable esters or thioesters of the aforementioned hydroxyl or thiol groups with an acid selected from the group consisting of cinnamic, maleic, fumaric ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;
D) R7 is selected from the group consisting of
  (1) hydrogen or hydroxyl;
  (2) halogen atoms;
  (3) pharmaceutically acceptable ether and thioether groups —Y—R23, wherein R23 is a $C_1$ halogenated or unhalogenated radical, a $C_2$–$C_4$ saturated or unsaturated, halogenated or unhalogenated straight chain radical, or a $C_3$–$C_4$ saturated or unsaturated, halogenated or unhalogenated branched chain radical, and Y is as previously defined; and
  (4) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;
except when R8 is hydroxyl, R7 is not hydroxyl; when R8 is hydroxyl or thiol, R7 is not halogen, an ether, or a thioether; and when the bond between carbons C16–C17 in formula I is a double bond, R7 is not present;
E) R8 is selected from the group consisting of:
  (1) hydroxyl, thiol, 2-hydroxyethanoyl

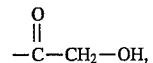

or 1-hydroxyethyl

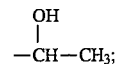

(2) pharmaceutically acceptable ester or thioester groups

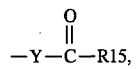

wherein Y and R15 are as previously defined;
  (3) pharmaceutically acceptable

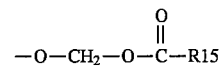

groups wherein R15 is as previously defined;
  (4) pharmaceutically acceptable

groups, wherein R15 is as previously defined;
  (5) pharmaceutically acceptable

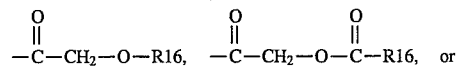

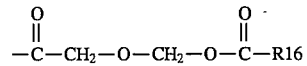

groups, wherein R16 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide

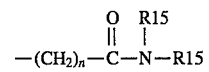

radical where n is 1-10, R15 is as previously defined, and each R15 is independently determined;
  (6) pharmaceutically acceptable oxime

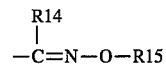

groups, where R14 and R15 are as previously defined;

(7) pharmaceutically acceptable thiazolidine derivatives having the formula:

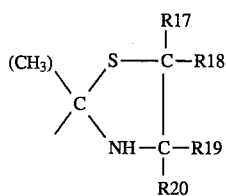

wherein any two of R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

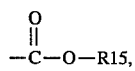

wherein R15 is as previously defined;

(8) pharmaceutically acceptable

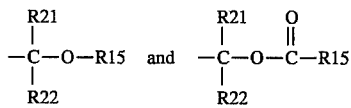

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, or a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined;

(9) pharmaceutically acceptable carboxylate

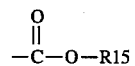

groups wherein R15 is as previously defined;

(10) pharmaceutically acceptable

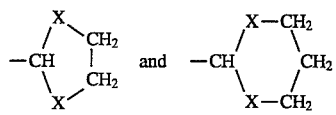

groups wherein each X independently is oxygen, nitrogen, or sulfur;

(11) cyano —C≡N; and

(12) pharmaceutically acceptable esters or thioesters of the aforementioned hydroxyl or thiol groups with an acid selected from the group consisting of cinnamic, maleic, fumaric, ascorbic, pimelic, succinic, bism- ethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

or R7 and R8 combined are =CH—CH₃;

F) R9 is selected from the group consisting of
   (1) hydrogen; and
   (2) $C_1$–$C_6$ alkyl, halo-, dihalo-, and trihaloalkyl, or $C_6$ aryl, halo-, dihalo-, and trihaloaryl, except if the bond between carbons C9–C11 in formula I is a double bond, then R9 is not present;

G) R10 and R13 are individually selected from the group consisting of
   (1) hydrogen; and
   (2) $C_1$–$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
   (1) hydrogen, hydroxyl, or thiol;
   (2) $C_1$–$C_{10}$ alkyloxy and alkylthio radicals, $C_6$–$C_{10}$ aryloxy and arylthio radicals, or amino radicals;
   (3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
   (4) pharmaceutically acceptable

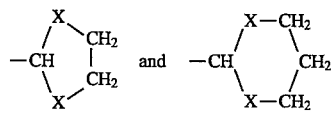

groups wherein each X independently is as previously defined;

or together R11 and R12 make a double bond to oxygen or sulfur to form the ketone or thioketone; except if the bond between carbons C9–C11 or C11–C12 in formula I is a double bond, then R12 is not present.

115. The method of claim 114 wherein the neuroactive steroid compound is selected from the group consisting of 3α-hydroxy-2β-methoxy-5α-pregnan-20-one, 3α,21-dihydroxy-5α-pregnan-20-one, 3α,20α-dihydroxy-5α-pregnane, 3α,20-dihydroxy-20-methyl-5α-pregnane, 3α,20-dihydroxy-3β,20-dimethyl-5α-pregnane, 3α-hydroxy-3β-methyl-5α-pregnan-20-one, 3α-hydroxy-5α-pregnan-20-one, and 3α-isobutyryloxy-5α-pregnan-20-one.

116. The method of claim 114 wherein the neuroactive steroid compound is 3α-hydroxy-3β-methyl-5α-pregnan-20-one.

117. A method for treating or preventing insomnia in an animal in need of such treatment or prevention, comprising administering to said animal a therapeutically effective amount of a neuroactive steroid compound of the formula I:

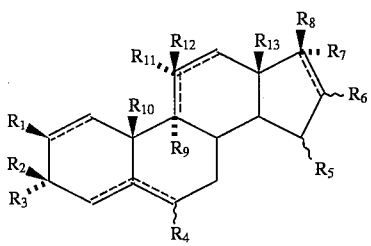

wherein

A) R1, R4, R5, and R6 are individually selected from the group consisting of:
(1) hydrogen, hydroxyl, or thiol;
(2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
(3) halogen atoms; and
(4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;

B) R2 is selected from the group consisting of
(1) hydrogen; and
(2) a $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;

C) R3 is selected from the group consisting of:
(1) hydroxyl or thiol;
(2) pharmaceutically acceptable ester and thioester groups

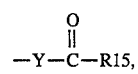

wherein R15 is hydrogen or a $C_1$ halogenated or unhalogenated radical, a $C_2$–$C_{20}$ saturated or unsaturated, halogenated or unhalogenated straight chain radical, a $C_3$–$C_{20}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
(3) pharmaceutically acceptable cleavable esters of natural or synthetic amino acids;
(4) pharmaceutically acceptable acyloxyalkyloxy or acyloxyalkylthio

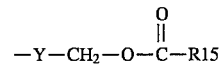

radicals, wherein Y and R15 are as previously defined; and
(5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

D) R7 is selected from the group consisting of
(1) hydrogen or hydroxyl;
(2) halogen atoms;
(3) pharmaceutically acceptable ether and thioether groups —Y—R23, wherein R23 is a $C_1$ halogenated or unhalogenated radical, a $C_2$–$C_4$ saturated or unsaturated, halogenated or unhalogenated straight chain radical, or a $C_3$–$C_4$ saturated or unsaturated, halogenated or unhalogenated branched chain radical, and Y is as previously defined; and
(4) a pharmaceutically acceptable $C_1$ halogenated or unhalogenated radical, $C_2$–$C_4$ saturated or unsaturated, halogenated or unhalogenated straight chain radicals, or $C_3$–$C_4$ saturated or unsaturated, halogenated or unhalogenated branched chain radicals;

except when R8 is hydroxyl, R7 is not hydroxyl; when R8 is hydroxyl or thiol, R7 is not halogen, an ether, or a thioether; and when the bond between carbons C16–C17 in formula I is a double bond, R7 is not present;

E) R8 is selected from the group consisting of:
(1) hydroxyl, thiol, 2-hydroxyethanoyl

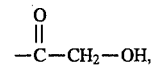

or 1-hydroxyethyl

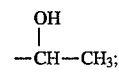

(2) pharmaceutically acceptable ester or thioester groups

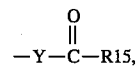

wherein Y and R15 are as previously defined;
(3) pharmaceutically acceptable

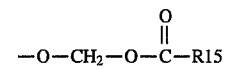

groups wherein R15 is as previously defined;

(4) pharmaceutically acceptable

groups, wherein R15 is as previously defined;

(5) pharmaceutically acceptable

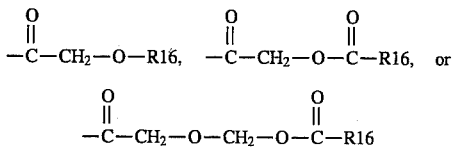

groups, wherein R16 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide

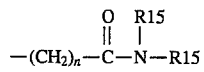

radical where n is 1–10, R15 is as previously defined, and each R15 is independently determined;

(6) pharmaceutically acceptable oxime

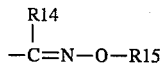

groups, where R14 and R15 are as previously defined;

(7) pharmaceutically acceptable thiazolidine derivatives having the formula:

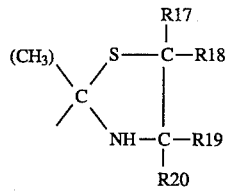

wherein any two of R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

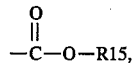

wherein R15 is as previously defined;

(8) pharmaceutically acceptable

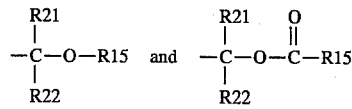

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, or a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined;

(9) pharmaceutically acceptable carboxylate

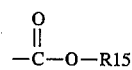

groups wherein R15 is as previously defined;

(10) pharmaceutically acceptable

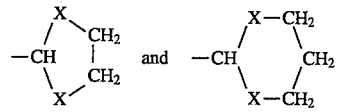

groups wherein each X independently is oxygen, nitrogen, or sulfur;

(11) cyano —C≡N; and

(12) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

or R7 and R8 combined are =CH—CH$_3$; except when R3 is hydroxyl and R2 is hydrogen and R10 and R13 are both methyl, R8 is not acetyl or 2-hydroxyethanoyl;

F) R9 is selected from the group consisting of
 (1) hydrogen; and
 (2) $C_1$–$C_6$ alkyl, halo-, dihalo-, and trihaloalkyl, or $C_6$ aryl, halo-, dihalo-, and trihaloaryl, except if the bond between carbons C9–C11 in formula I is a double bond, then R9 is not present;

G) R10 and R13 are individually selected from the group consisting of
 (1) hydrogen; and
 (2) $C_1$–$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
 (1) hydrogen, hydroxyl, or thiol:
 (2) $C_1$–$C_{10}$ alkyloxy and alkylthio radicals, $C_6$–$C_{10}$ aryloxy and arylthio radicals, or amino radicals;
 (3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3-C_{10}$ cyclic aliphatic radicals, $C_6-C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and (4) pharmaceutically acceptable

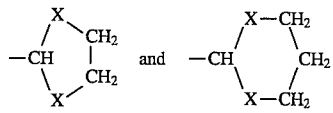

groups wherein each X independently is as previously defined;

or together R11 and R12 make a double bond to oxygen or sulfur to form the ketone or thioketone; except if the bond between carbons C9–C11 or C11,C12 in formula I is a double bond, then R12 is not present.

118. The method of claim 117 wherein the neuroactive steroid compound is selected from the group consisting of 3α-hydroxy-2β-methoxy-5α-pregnan-20-one, 3α,21-dihydroxy-5α-pregnan-20-one, 3α,20α-dihydroxy-5α-pregnane, 3α,20-dihydroxy-20-methyl-5α-pregnane, 3α,20-dihydroxy-3β,20-dimethyl-5α-pregnane, 3α-hydroxy-3β-methyl-5α-pregnan-20-one, 3α-hydroxy-5α-pregnan-20-one, and 3α-isobutyryloxy-5α-pregnan-20-one.

119. The method of claim 117 wherein the neuroactive steroid compound is 3α-hydroxy-3β-methyl-5α-pregnan-20-one.

120. A method for treating or preventing stress in an animal in need of such treatment or prevention, comprising administering to said animal a therapeutically effective amount of a neuroactive steroid compound of the formula I:

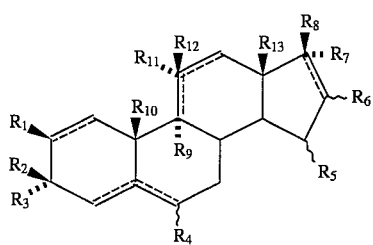

wherein

A) R1, R4, R5, and R6 are individually selected from the group consisting of:
(1) hydrogen, hydroxyl, or thiol;
(2) pharmaceutically acceptable ether and thioether groups —Y—R14, wherein R14 is a $C_1$ halogenated or unhalogenated radical, a $C_2-C_{10}$ saturated or unsaturated, halogenated or unhalogenated straight chain radical, a $C_3-C_{10}$ saturated or unsaturated, halogenated or unhalogenated branched chain radical, a $C_3-C_{10}$ cyclic aliphatic radical, a $C_6-C_{10}$ aromatic radical, or a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
(3) halogen atoms; and
(4) a $C_1$ halogenated or unhalogenated radical, $C_2-C_8$ saturated or unsaturated, halogenated or unhalogenated straight chain radicals, $C_3-C_8$ saturated or unsaturated, halogenated or unhalogenated branched chain radicals, or $C_3-C_8$ cyclic aliphatic radicals;

B) R2 is selected from the group consisting of
(1) hydrogen; and
(2) a $C_1$ halogenated or unhalogenated radical, $C_2-C_2$ saturated or unsaturated, halogenated or unhalogenated straight chain radicals, or $C_3-C_4$ saturated or unsaturated, halogenated or unhalogenated branched chain radicals;

C) R3 is selected from the group consisting of:
(1) hydroxyl or thiol;
(2) pharmaceutically acceptable ester and thioester groups

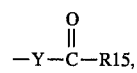

wherein R15 is hydrogen or a $C_1$ halogenated or unhalogenated radical, a $C_2-C_{20}$ saturated or unsaturated, halogenated or unhalogenated straight chain radical, a $C_3-C_{20}$ saturated or unsaturated, halogenated or unhalogenated branched chain radical, a $C_3-C_{10}$ cyclic aliphatic radical, a $C_6-C_{10}$ aromatic radical, or a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
(3) pharmaceutically acceptable cleavable esters of natural or synthetic amino acids;
(4) pharmaceutically acceptable acyloxyalkyloxy or acyloxyalkylthio

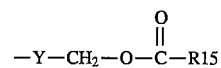

radicals, wherein Y and R15 are as previously defined; and
(5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

D) R7 is selected from the group consisting of
(1) hydrogen or hydroxyl;
(2) halogen atoms;
(3) pharmaceutically acceptable ether and thioether groups —Y—R23, wherein R23 is a $C_1$ halogenated or unhalogenated radical, a $C_2-C_4$ saturated or unsaturated, halogenated or unhalogenated straight chain radical, or a $C_3-C_4$ saturated or unsaturated, halogenated or unhalogenated branched chain radical, and Y is as previously defined; and
(4) a pharmaceutically acceptable $C_1$ halogenated or unhalogenated radical, $C_2-C_4$ saturated or unsaturated, halogenated or unhalogenated straight chain radicals, or $C_3-C_4$ saturated or unsaturated, halogenated or unhalogenated branched chain radicals;

except when R8 is hydroxyl, R7 is not hydroxyl; when R8 is hydroxyl or thiol, R7 is not halogen, an ether, or a thioether, and when the bond between carbons C16–C17 in formula I is a double bond, R7 is not present;

E) R8 is selected from the group consisting of:
(1) hydroxyl, thiol, 2-hydroxyethanoyl

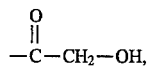

or 1-hydroxyethyl

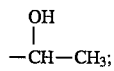

(2) pharmaceutically acceptable ester or thioester groups

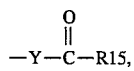

wherein Y and R15 are as previously defined;
(3) pharmaceutically acceptable

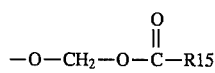

groups wherein R15 is as previously defined;
(4) pharmaceutically acceptable

groups, wherein R15 is as previously defined;
(5) pharmaceutically acceptable

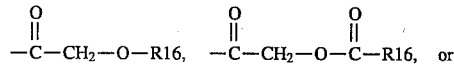

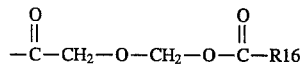

groups, wherein
R16 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide

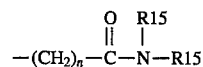

radical where n is 1-10, R15 is as previously defined, and each R15 is independently determined;
(6) pharmaceutically acceptable oxime

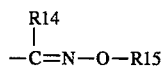

groups, where R14 and R15 are as previously defined;

(7) pharmaceutically acceptable thiazolidine derivatives having the formula:

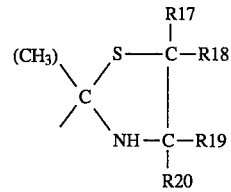

wherein any two of R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

wherein R15 is as previously defined;
(8) pharmaceutically acceptable

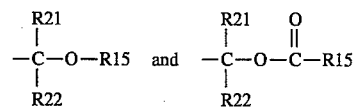

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, or a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined;
(9) pharmaceutically acceptable carboxylate

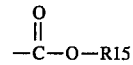

groups wherein R15 is as previously defined;
(10) pharmaceutically acceptable

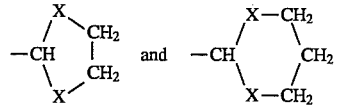

groups wherein each X independently is oxygen, nitrogen, or sulfur;
(11) cyano -C - N; and
(12) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic; or R7 and R8 combined are =CH—CH$_3$; except when R3 is hydroxyl and R2 is hydrogen and R10 and R13 are both methyl, R8 is not 2-hydroxyethanoyl;

F) R9 is selected from the group consisting of
   (1) hydrogen; and
   (2) $C_1$-$C_6$ alkyl, halo-, dihalo-, and trihaloalkyl, or $C_6$ aryl, halo-, dihalo-, and trihaloaryl, except if the bond between carbons C9–C11 in formula I is a double bond, then R9 is not present;

G) R10 and R13 are individually selected from the group consisting of
   (1) hydrogen; and
   (2) $C_1$-$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
   (1) hydrogen, hydroxyl, or thiol;
   (2) $C_1$-$C_{10}$ alkyloxy and alkylthio radicals, $C_6$-$C_{10}$ aryloxy and arylthio radicals, or amino radicals;
   (3) a $C_1$ halogenated or unhalogenated radical, $C_2$-$C_{10}$ saturated or unsaturated, halogenated or unhalogenated straight chain radicals, $C_3$-$C_{10}$ saturated or unsaturated, halogenated or unhalogenated branched chain radicals, $C_3$-$C_{10}$ cyclic aliphatic radicals, $C_6$-$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
   (4) pharmaceutically acceptable

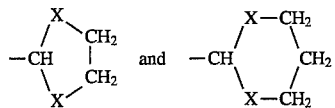

groups wherein each X independently is as previously defined;
or together R11 and R12 make a double bond to oxygen or sulfur to form the ketone or thioketone; except if the bond between carbons C9–C11 or C11–C12 in formula I is a double bond, then R12 is not present.

121. The method of claim 120 wherein the neuroactive steroid compound is selected from the group consisting of 3α-hydroxy-2β-methoxy-5α-pregnan-20-one, 3α,21-dihydroxy-5α-pregnan-20-one, 3α,20α-dihydroxy-5α-pregnane, 3α,20-dihydroxy-20-methyl-5α-pregnan, 3α,20-dihydroxy-3β,20-dimethyl-5α-pregnane, 3α-hydroxy-3β-methyl-5α-pregnan-20-one, 3α-hydroxy-5α-pregnan-20-one, and 3α-isobutyryloxy-5α-pregnan-20-one.

122. The method of claim 120 wherein the neuroactive steroid compound is 3α-hydroxy-3β-methyl-5α-pregnan-20-one.

123. A method for treating or preventing convulsions in an animal in need of such treatment or prevention, comprising administering to said animal a therapeutically effective amount of a neuroactive steroid compound of the formula I:

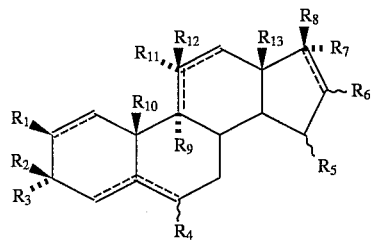

wherein

A) R1, R4, R5, and R6 are individually selected from the group consisting of:
   (1) hydrogen, hydroxyl, or thiol;
   (2) pharmaceutically acceptable ether and thioether groups —Y—R14, wherein R14 is a $C_1$ halogenated or unhalogenated radical, a $C_2$-$C_{10}$ saturated or unsaturated, halogenated or unhalogenated straight chain radical, a $C_3$-$C_{10}$ saturated or unsaturated, halogenated or unhalogenated branched chain radical, a $C_3$-$C_{10}$ cyclic aliphatic radical, a $C_6$-$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
   (3) halogen atoms; and
   (4) a $C_1$ halogenated or unhalogenated radical, $C_2$-$C_8$ saturated or unsaturated, halogenated or unhalogenated straight chain radicals, $C_3$-$C_8$ saturated or unsaturated, halogenated or unhalogenated branched chain radicals, or $C_3$-$C_8$ cyclic aliphatic radicals;

B) R2 is selected from the group consisting of
   (1) hydrogen; and
   (2) a $C_8$ halogenated or unhalogenated radical, $C_2$-$C_4$ saturated or unsaturated, halogenated or unhalogenated straight chain radicals, or $C_3$-$C_4$ saturated or unsaturated, halogenated or unhalogenated branched chain radicals;

C) R3 is selected from the group consisting of:
   (1) hydroxyl or thiol;
   (2) pharmaceutically acceptable ester and thioester groups

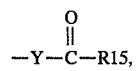

wherein R15 is hydrogen or a $C_1$ halogenated or unhalogenated radical, a $C_2$-$C_{20}$ saturated or unsaturated, halogenated or unhalogenated straight chain radical, a $C_3$-$C_{20}$ saturated or unsaturated, halogenated or unhalogenated branched chain radical, a $C_3$-$C_{10}$ cyclic aliphatic radical, a $C_6$-$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
   (3) pharmaceutically acceptable cleavable esters of natural or synthetic amino acids;

(4) pharmaceutically acceptable acyloxyalkyloxy or acyloxyalkylthio

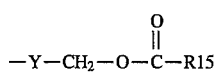

radicals, wherein Y and R15 are as previously defined; and (5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethamino)-propionic, phosphoric, phosphonic, sulfuric, sulfonic, glucuronic, and 1-methyl-1,4-dihydro nicotinic;

D) R7 is selected from the group consisting of
(1) hydrogen or hydroxyl;
(2) halogen atoms;
(3) pharmaceutically acceptable ether and thioether groups —Y—R23, wherein R23 is a $C_1$ halogenated or unhalogenated radical, a $C_2$-$C_4$ saturated or unsaturated, halogenated or unhalogenated straight chain radical, or a $C_3$-$C_4$ saturated or unsaturated, halogenated or unhalogenated branched chain radical, and Y is as previously defined; and
(4) a pharmaceutically acceptable $C_1$ halogenated or unhalogenated radical, $C_2$-$C_4$ saturated or unsaturated, halogenated or unhalogenated straight chain radicals, or $C_3$-$C_4$ saturated or unsaturated, halogenated or unhalogenated branched chain radicals;

except when R8 is hydroxyl, R7 is not hydroxyl; when R8 is hydroxyl or thiol, R7 is not halogen, an ether, or a thioether; and when the bond between carbons C16–C17 in formula I is a double bond, R7 is not present;

E) R8 is selected from the group consisting of:
(1) hydroxyl, thiol, 2-hydroxyethanoyl

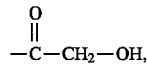

or 1-hydroxyethyl

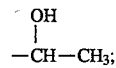

(2) pharmaceutically acceptable ester or thioester groups

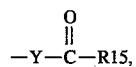

wherein Y and R15 are as previously defined;
(3) pharmaceutically acceptable

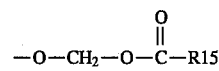

groups wherein R15 is as previously defined;

(4) pharmaceutically acceptable

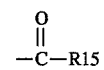

groups, wherein R15 is as previously defined;
(5) pharmaceutically acceptable

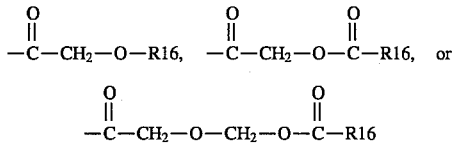

groups, wherein R16 is a $C_1$ halogenated or unhalogenated radical, a $C_2$-$C_{10}$ saturated or unsaturated, halogenated or unhalogenated straight chain radical, a $C_3$-$C_{10}$ saturated or unsaturated, halogenated or unhalogenated branched chain radical, a $C_3$-$C_{10}$ cyclic aliphatic radical, a $C_6$-$C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide

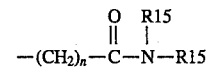

radical where n is 1-10, R15 is as previously defined, and each R15 is independently determined;
(6) pharmaceutically acceptable oxime

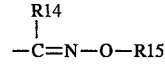

groups, where R14 and R15 are as previously defined;
(7) pharmaceutically acceptable thiazolidine derivatives having the formula:

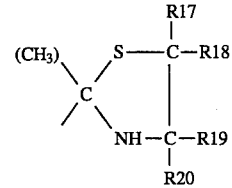

wherein any two of R17, R18, R19 and R20 are individually hydrogen or a $C_1$ halogenated or unhalogenated radical, a $C_2$-$C_{10}$ saturated or unsaturated, halogenated or unhalogenated straight chain radical, a $C_3$-$C_{10}$ saturated or unsaturated, halogenated or unhalogenated branched chain radical, a $C_3$-$C_8$ cyclic aliphatic radical, a $C_6$-$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

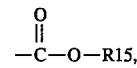

wherein R15 is as previously defined;

(8) pharmaceutically acceptable

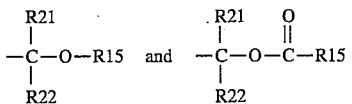

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, or a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined;

(9) pharmaceutically acceptable carboxylate

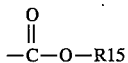

groups wherein R15 is as previously defined;

(10) pharmaceutically acceptable

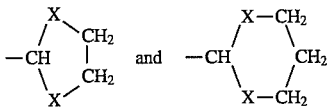

groups wherein each X independently is oxygen, nitrogen, or sulfur;

(11) cyano -C - N; and

(12) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic; or R7 and R8 combined are =CH—CH$_3$; except when R3 is hydroxyl and R2 is hydrogen and R10 and R13 are both methyl, R8 is not acetyl;

F) R9 is selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl, except if the bond between carbons C9–C11 in formula I is a double bond, then R9 is not present;

G) R10 and R13 are individually selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
(1) hydrogen, hydroxyl, or thiol;
(2) $C_1$–$C_{10}$ alkyloxy and alkylthio radicals, $C_6$–$C_{10}$ aryloxy and arylthio radicals, or amino radicals;
(3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and (4) pharmaceutically acceptable

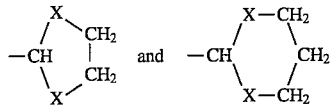

groups wherein each X independently is as previously defined;

or together R11 and R12 make a double bond to oxygen or sulfur to form the ketone or thioketone; except if the bond between carbons C9–C11 or C11–C12 in formula I is a double bond, then R12 is not present.

124. The method of claim 123 wherein the neuroactive steroid compound is selected from the group consisting of 3α-hydroxy-2β-methoxy-5α-pregnan-20-one, 3α,21-dihydroxy-5α-pregnan-20-one, 3α,20α-dihydroxy-5α-pregnane, 3α,20-dihydroxy-20-methyl-5α-pregnane, 3α,20-dihydroxy-3β,20-dimethyl-5α-pregnane, 3α-hydroxy-3β-methyl-5α-pregnan-20-one, 3α-hydroxy-5α-pregnan-20-one, and 3α-isobutyryloxy-5α-pregnan-20-one.

125. A method for treating or preventing muscle tension in an animal in need of such treatment or prevention, comprising administering to said animal a therapeutically effective amount of a neuroactive steroid compound of the formula I:

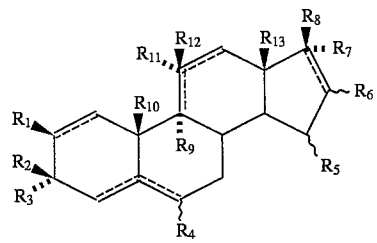

wherein
A) R1, R4, R5, and R6 are individually selected from the group consisting of:
(1) hydrogen, hydroxyl, or thiol;
(2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N-attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
(3) halogen atoms; and
(4) a $C_1$ halogenated or unhalogenated radical, $C_2$–$C_8$ saturated or unsaturated, halogenated or unhalogenated straight chain radicals, $C_3$–$C_8$ saturated or unsaturated, halogenated or unhalogenated branched chain radicals, or $C_3$–$C_8$ cyclic aliphatic radicals;

B) R2 is selected from the group consisting of
(1) hydrogen; and
(2) a $C_1$ halogenated or unhalogenated radical, $C_2$–$C_4$ saturated or unsaturated, halogenated or unhalogenated straight chain radicals, or $C_3-C_4$ saturated or unsaturated, halogenated or unhalogenated branched chain radicals;

C) R3 is selected from the group consisting of:
  (1) hydroxyl or thiol;
  (2) pharmaceutically acceptable ester and thioester groups $$-Y-\overset{O}{\underset{\|}{C}}-R15,$$

wherein R15 is hydrogen or a $C_1$ halogenated or unhalogenated radical, a $C_2-C_{20}$ saturated or unsaturated, halogenated or unhalogenated straight chain radical, a $C_3-C_{20}$ saturated or unsaturated, halogenated or unhalogenated branched chain radical, a $C_3-C_{10}$ cyclic aliphatic radical, a $C_6-C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
  (3) pharmaceutically acceptable cleavable esters of natural or synthetic amino acids;
  (4) pharmaceutically acceptable acyloxyalkyloxy or acyloxyalkylthio $$-Y-CH_2-O-\overset{O}{\underset{\|}{C}}-R15$$

radicals, wherein Y and R15 are as previously defined; and
  (5) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

D) R7 is selected from the group consisting of
  (1) hydrogen or hydroxyl;
  (2) halogen atoms;
  (3) pharmaceutically acceptable ether and thioether groups —Y—R23, wherein R23 is a $C_1$ halogenated or unhalogenated radical, a $C_2-C_4$ saturated or unsaturated, halogenated or unhalogenated straight chain radical, or a $C_3-C_4$ saturated or unsaturated, halogenated or unhalogenated branched chain radical, and Y is as previously defined; and
  (4) a pharmaceutically acceptable $C_1$ halogenated or unhalogenated radical, $C_2-C_4$ saturated or unsaturated, halogenated or unhalogenated straight chain radicals, or $C_3-C_4$ saturated or unsaturated, halogenated or unhalogenated branched chain radicals;
except when R8 is hydroxyl, R7 is not hydroxyl; when R8 is hydroxyl or thiol, R7 is not halogen, an ether, or a thioether; and when the bond between carbons C16–C17 in formula I is a double bond, R7 is not present;

E) R8 is selected from the group consisting of:
  (1) hydroxyl, thiol, 2-hydroxyethanoyl $$-\overset{O}{\underset{\|}{C}}-CH_2-OH,$$

or 1-hydroxyethyl $$-\overset{OH}{\underset{|}{C}H}-CH_3;$$

(2) pharmaceutically acceptable ester or thioester groups $$-Y-\overset{O}{\underset{\|}{C}}-R15,$$

wherein Y and R15 are as previously defined;
  (3) pharmaceutically acceptable $$-O-CH_2-O-\overset{O}{\underset{\|}{C}}-R15$$

groups wherein R15 is as previously defined;
  (4) pharmaceutically acceptable $$-\overset{O}{\underset{\|}{C}}-R15$$

groups, wherein R15 is as previously defined;
  (5) pharmaceutically acceptable $$-\overset{O}{\underset{\|}{C}}-CH_2-O-R16, \quad -\overset{O}{\underset{\|}{C}}-CH_2-O-\overset{O}{\underset{\|}{C}}-R16, \quad \text{or}$$

$$-\overset{O}{\underset{\|}{C}}-CH_2-O-CH_2-O-\overset{O}{\underset{\|}{C}}-R16$$

groups, wherein R16 is a $C_1$ halogenated or unhalogenated radical, a $C_2-C_{10}$ saturated or unsaturated, halogenated or unhalogenated straight chain radical, a $C_3-C_{10}$ saturated or unsaturated, halogenated or unhalogenated branched chain radical, a $C_3-C_{10}$ cyclic aliphatic radical, a $C_6-C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide $$-(CH_2)_n-\overset{O}{\underset{\|}{C}}-\overset{R15}{\underset{|}{N}}-R15$$

radical where n is 1-10, R15 is as previously defined, and each R15 is independently determined;
  (6) pharmaceutically acceptable oxime $$-\overset{R14}{\underset{|}{C}}=N-O-R15$$

groups, where R14 and R15 are as previously defined;
  (7) pharmaceutically acceptable thiazolidine derivatives having the formula:

wherein any two of R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

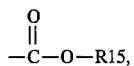

wherein R15 is as previously defined;
(8) pharmaceutically acceptable

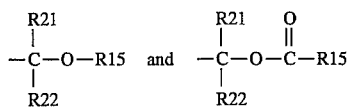

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, or a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined;
(9) pharmaceutically acceptable carboxylate

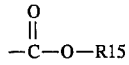

groups wherein R15 is as previously defined;
(10) pharmaceutically acceptable

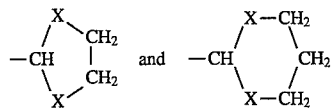

groups wherein each X independently is oxygen, nitrogen, or sulfur;
(11) cyano -C - N; and
(12) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

or R7 and R8 combined are =CH—$CH_3$;

F) R9 is selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl, except if the bond between carbons C9–C11 in formula I is a double bond, then R9 is not present;

G) R10 and R13 are individually selected from the group consisting of (1) hydrogen; and
(2) $C_1$–$C_6$ alkyl, halo-, dihalo-, and trihaloalkyl, or $C_6$ aryl, halo-, dihalo-, and trihaloaryl; and H) one of R11 and R12 is hydrogen, and the other is selected from the group consisting of
(1) hydrogen, hydroxyl, or thiol;
(2) $C_1$–$C_{10}$ alkyloxy and alkylthio radicals, $C_6$–$C_{10}$ aryloxy and arylthio radicals, or amino radicals;
(3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
(4) pharmaceutically acceptable

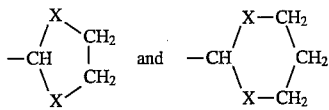

groups wherein each X independently is as previously defined;
or together R11 and R12 make a double bond to oxygen or sulfur to form the ketone or thioketone; except if the bond between carbons C9–C11 or C11–C12 in formula I is a double bond, then R12 is not present.

126. The method of claim 125 wherein the neuroactive steroid compound is selected from the group consisting of 3α-hydroxy-2β-methoxy-5α-pregnan-20-one, 3α,21-dihydroxy-5α-pregnan-20-one, 3α,20α-dihydroxy-5α-pregnane, 3α,20-dihydroxy-20-methyl-5α-pregnane, 3α,20-dihydroxy-3β,20-dimethyl-5α-pregnane, 3α-hydroxy-3β-methyl-5α-pregnan-20-one, 3α-hydroxy-5α-pregnan-20-one, and 3α-isobutyryloxy-5α-pregnan-20-one.

127. The method of claim 125 wherein the neuroactive steroid compound is 3α-hydroxy-3β-methyl-5α-pregnan-20-one.

128. A compound of the formula:

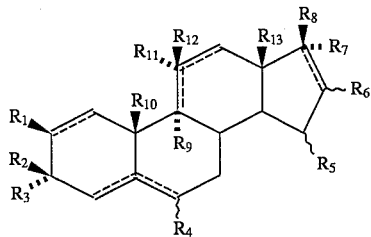

wherein
A) R1, R4, R5, and R6 are individually selected from the group consisting of:
(1) hydrogen, hydroxyl, or thiol;
(2) pharmaceutically acceptable ether and thioether groups —Y—R14, wherein R14 is a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms and Y is either a divalent oxygen or sulfur linkage;
(3) halogen atoms; and
(4) a $C_1$ halogenated or unhalogenated radical, $C_2$-$C_8$ saturated or unsaturated, halogenated or unhalogenated straight chain radicals, $C_3$-$C_8$ saturated or unsaturated, halogenated or unhalogenated branched chain radicals, or $C_3$-$C_8$ cyclic aliphatic radicals;

B) R2 is trifluoromethyl;

C) R3 is selected from the group consisting of:
(1) hydroxyl or thiol;
(2) pharmaceutically acceptable ester and thioester groups

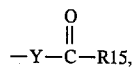

wherein R15 is hydrogen, a $C_1$ halogenated or unhalogenated radical, a $C_2$-$C_{20}$ saturated or unsaturated, halogenated or unhalogenated straight chain radical, a $C_3$-$C_{20}$ saturated or unsaturated, halogenated or unhalogenated branched chain radical, a $C_3$-$C_{10}$ cyclic aliphatic radical, a $C_6$-$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and Y is as previously defined;
(3) pharmaceutically acceptable cleavable esters of natural or synthetic amino acids;
(4) pharmaceutically acceptable acyloxyalkyloxy or acyloxyalkylthio

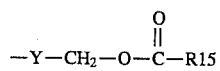

radicals, wherein Y and R15 are as previously defined; and
(5) pharmaceutically acceptable esters or thioesters of the aforementioned hydroxyl or thiol groups with an acid selected from the group consisting of cinnamic, maleic, fumaric, ascorbic, pimelic, succinic, bism-ethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;

D) R7 is selected from the group consisting of
(1) hydrogen or hydroxyl;
(2) halogen atoms;
(3) pharmaceutically acceptable ether and thioether groups —Y—R23, wherein R23 is a $C_1$ halogenated or unhalogenated radical, a $C_2$-$C_4$ saturated or unsaturated, halogenated or unhalogenated straight chain radical, or a $C_3$-$C_4$ saturated or unsaturated, halogenated or unhalogenated branched chain radical, and Y is as previously defined; and
(4) a pharmaceutically acceptable $C_1$ halogenated or unhalogenated radical, $C_2$-$C_4$ saturated or unsaturated, halogenated or unhalogenated straight chain radicals, or $C_3$-$C_4$ saturated or unsaturated, halogenated or unhalogenated branched chain radicals;
except when R8 is hydroxyl, R7 is not hydroxyl; when R8 is hydroxyl or thiol, R7 is not halogen, an ether, or a thioether; and when the bond between carbons C16–C17 in formula I is a double bond, R7 is not present;

E) R8 is selected from the group consisting of:

(1) hydroxyl, thiol, 2-hydroxyethanoyl

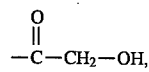

or 1-hydroxyethyl

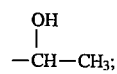

(2) pharmaceutically acceptable ester or thioester groups

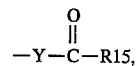

wherein Y and R15 are as previously defined;
(3) pharmaceutically acceptable

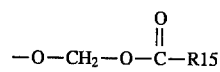

groups wherein R15 is as previously defined;
(4) pharmaceutically acceptable

groups, wherein R15 is as previously defined;
(5) pharmaceutically acceptable

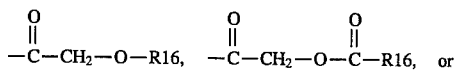

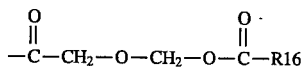

groups wherein R16 is a $C_1$ halogenated or unhalogenated radical, a $C_2$-$C_{10}$ saturated or unsaturated, halogenated or unhalogenated straight chain radical, a $C_3$-$C_{10}$ saturated or unsaturated, halogenated or unhalogenated branched chain radical, a $C_3$-$C_{10}$ cyclic aliphatic radical, a $C_6$-$C_{10}$ aromatic radical, a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, or an amide

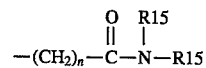

radical where n is 1-10, R15 is as previously defined, and each R15 is independently determined;
(6) pharmaceutically acceptable oxime

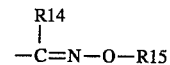

groups, where R14 and R15 are as previously defined;

(7) pharmaceutically acceptable thiazolidine derivatives having the formula:

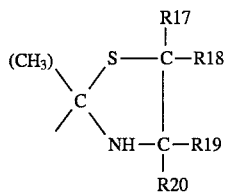

wherein any two of R17, R18, R19 and R20 are individually hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_8$ cyclic aliphatic radical, a $C_6$–$C_8$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and the remaining two of R17, R18, R19 and R20 are individually hydrogen; or one or more of R17, R18, R19, and R20 are individually

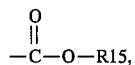

wherein R15 is as previously defined;
(8) pharmaceutically acceptable

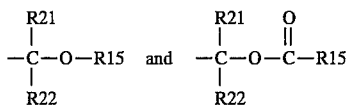

groups wherein one of R21 and R22 is hydrogen or methyl and the other is hydrogen or a $C_1$ halogenated or unhalogenated radical, a $C_2$–$C_{10}$ saturated or unsaturated, halogenated or unhalogenated straight chain radical, a $C_3$–$C_{10}$ saturated or unsaturated, halogenated or unhalogenated branched chain radical, a $C_3$–$C_{10}$ cyclic aliphatic radical, a $C_6$–$C_{10}$ aromatic radical, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms, and R15 is as previously defined;
(9) pharmaceutically acceptable carboxylate

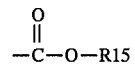

groups wherein R15 is as previously defined;
(10) pharmaceutically acceptable

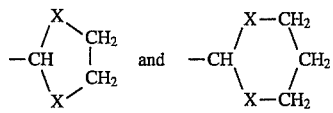

groups wherein each X independently is oxygen, nitrogen, or sulfur;

(11) cyano -C - N; and
(12) pharmaceutically acceptable esters or thioesters of the aforementioned hydroxyl or thiol groups with an acid selected from the group consisting of cinnamic, maleic, fumaric, ascorbic, pimelic, succinic, bismethylene-salicylic, methanesulfonic, ethanesulfonic, oxalic, tartaric, salicylic, acetyl salicylic, citric, gluconic, stearic, palmitic, itaconic, glycolic, p-aminobenzoic, benzenesulfonic, cyclohexyl-sulfamic, α-(2-hydroxyethylamino)-propionic, phosphoric, phosphonic, sulfuric, sulfonic, glucuronic, and 1-methyl-1,4-dihydro nicotinic;
or R7 and R8 combined are =CH—CH₃;
F) R9 is selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl; except if the bond between carbons C9–C11 in formula I is a double bond, then R9 is not present;
G) R10 and R13 are individually selected from the group consisting of
(1) hydrogen; and
(2) $C_1$–$C_6$ alkyl, halo-, dihalo-, and trihaloalkyl, or $C_6$ aryl, halo-, dihalo-, and trihaloaryl; and
H) one of R11 and R12 is hydrogen, and the other is selected from the group consisting of
(1) hydrogen, hydroxyl, or thiol;
(2) $C_1$–$C_{10}$ alkyloxy and alkylthio radicals, $C_6$–$C_{10}$ aryloxy and arylthio radicals, Or amino radicals;
(3) a $C_1$ halogenated or unhalogenated radical, $C_2$–$C_{10}$ saturated or unsaturated, halogenated or unhalogenated straight chain radicals, $C_3$–$C_{10}$ saturated or unsaturated, halogenated or unhalogenated branched chain radicals, $C_3$–$C_{10}$ cyclic aliphatic radicals, $C_6$–$C_{10}$ aromatic radicals, or a 4, 5, or 6 membered C- or N- attached heterocyclic radical containing 1, 2, or 3 heteroatoms selected from the group consisting of oxygen, nitrogen, and sulfur, excluding heterocyclic radicals with two or more adjacent O or S atoms; and
(4) pharmaceutically acceptable

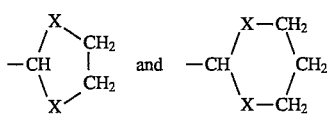

groups wherein each X independently is as previously defined;
or together R11 and R12 make a double bond to oxygen or sulfur to form the ketone or thioketone; except if the bond between carbons C9–C11 or C11–C12 in formula I is a double bond, then R12 is not present.
129. The method of claim 102 wherein the seizures are petit mal epileptic seizures.

* * * * *